(12) United States Patent
Parks et al.

(10) Patent No.: US 10,036,072 B2
(45) Date of Patent: Jul. 31, 2018

(54) MERCURY METHYLATION GENES IN BACTERIA AND ARCHAEA

(71) Applicant: UT-Battelle, LLC, Oak Ridge, TN (US)

(72) Inventors: Jerry M. Parks, Knoxville, TN (US); Alexander Johs, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 933 days.

(21) Appl. No.: 14/132,906

(22) Filed: Dec. 18, 2013

(65) Prior Publication Data

US 2014/0179553 A1 Jun. 26, 2014

Related U.S. Application Data

(60) Provisional application No. 61/739,302, filed on Dec. 19, 2012.

(51) Int. Cl.
| | | |
|---|---|---|
| *C12Q 1/68* | (2006.01) | |
| *C12P 19/34* | (2006.01) | |
| *C12Q 1/689* | (2018.01) | |

(52) U.S. Cl.
CPC ....... *C12Q 1/689* (2013.01); *C12Q 2600/142* (2013.01)

(58) Field of Classification Search
None
See application file for complete search history.

(56) References Cited

PUBLICATIONS

Klein et al. (2002) Proc Natl. Acad. Sci. USA vo. 99 No. 11 pp. 7542-7547.*
Banerjee, R. et al., The Many Faces of Vitamin B12: Catalysis by Cobalamin-Dependent Enzymes, Annu. Rev. Biochem., (2003), vol. 72, pp. 209-247.
Bridou, R. et al., Simultaneous Determination of Mercury Methylation and Demethylation Capacities of Various Sulfate-Reducing Bacteria Using Species-Specific Isotopic Tracers, Environmental Toxicology and Chemistry, (2011), vol. 30, No. 2, pp. 337-344.
Compeau, G.C. et al., Sulfate-Reducing Bacteria: Principal Methylators of Mercury in Anoxic Estuarine Sediment, Applied and Environmental Microbiology, (Aug. 1985), vol. 50, No. 2, pp. 498-502.
Ekstrom, E.B. et al., Mercury Methylation Independent of the Acetyl-Coenzyme A Pathway in Sulfate-Reducing Bacteria, Applied and Environmental Microbiology, (Sep. 2003), vol. 69, No. 9, pp. 5414-5422.
Goetzl, S. et al., Structural Basis for Electron and Methyl-Group Transfer in a Methyltransferase System Operating in the Reductive Acetyl-CoA Pathway, J. Mol. Biol., (2011), vol. 411, pp. 96-109.
Graham, A.M. et al., Kinetics of Hg-Cell Association, Hg Methylation, and MeHg Degradation in *desulfovibrio* Species With and Without the Ability to Methylate Hg, Appl. Environ. Microb., (2012), vol. 78, pp. 7337-7346.
Hill, H. et al., Kinetics of Substitution of Co-ordinated Carbanions in Cobalt(III) Corrinoids, Chemical Communications, (1970), pp. 341.
Keller, K.L. et al., Development of a Markerless Genetic Exchange System for Desulfovibrio vulgaris Hildenborough and Its Use in Generating a Strain with Increased Transformation Efficiency, Applied and Environmental Microbiology, (Dec. 2009), vol. 75, No. 24, pp. 7682-7691.
Keller, K.L. et al., Methods for Engineering Sulfate Reducing Bacteria of the Genus *Desulfovibrio*, Methods in Enzymology, (2011), vol. 497, pp. 503-517.
Kerin, E.J. et al., Mercury Methylation by Dissimilatory Iron-Reducing Bacteria, Applied and Environmental Microbiology, (Dec. 2006), vol. 72, No. 12, pp. 7919-7921.
King, J.K. et al., Sulfate-Reducing Bacteria Methylate Mercury at Variable Rates in Pure Culture and in Marine Sediments, Applied and Environmental Microbiology, (Jun. 2000), vol. 66, No. 6, pp. 2430-2437.
Kung, Y. et al., Visualizing molecular juggling within a B12-dependent methyltransferase complex, Nature, (Apr. 12, 20012), vol. 484, pp. 265-271.
Polson, S.M. et al., The First X-ray Structural Evidence Demonstrating Thiolate Coordination in an Organocobalt B12 Model Complex: Implications for Methionine Synthase, Inorg. Chem., (1997), vol. 36, pp. 307-313.
Ranchou-Peyruse, M. et al., Overview of Mercury Methylation Capacities among Anaerobic Bacteria Including Representatives of the Sulphate-Reducers: Implications for Environmental Studies, Geomicrobiology Journal, (2009), vol. 26, pp. 1-8.
Schrauzer, G.N. et al., Reductive Dealkylation of Alkylcobaloximes, Alkylcobalamins, and Related Compounds: Simulation of Corrin Dependent Reductase and Methyl Group Transfer Reactions, Bioinorganic Chemistry, (1972), vol. 2, pp. 93-124.
Wood, J.M. et al, Synthesis of Methyl-mercury Compounds by Extracts of a Methanogenic Bacterium, Nature, (Oct. 12, 1968), vol. 220, pp. 173-174.
Yu, R.Q. et al., Contribution of Coexisting Sulfate and Iron Reducing Bacteria to Methylmercury Production in Freshwater River Sediments, Environ. Sci. Technol., (Mar. 2012) vol. 46, No. 5, pp. 2684-2691.

(Continued)

*Primary Examiner* — Young J Kim

(74) *Attorney, Agent, or Firm* — Scully Scott Murphy & Presser

(57) ABSTRACT

Two genes required for this mercury methylation have been identified in bacteria and archaea. These genes are the hgcA gene and hgcB, a corrinoid protein that facilitates methyl group transfer to Hg, and a corrinoid protein-associated ferredoxin with two [4Fe-4S] binding motifs involved in generating cob(I)almin, respectively. The invention provides nucleic acid probes and primers for detecting methylmercury and or for assessing mercury methylation potential in environmental, clinical and other samples. The invention also provides antibodies against these proteins, antibodies against these proteins, methods of using the antibodies and methods of biocatalysis.

4 Claims, 14 Drawing Sheets
(12 of 14 Drawing Sheet(s) Filed in Color)

(56) References Cited

PUBLICATIONS

Brown, S.D. et al., Genome Sequence of the Mercury-Methylating Strain Desulfovibrio desulfuricans ND132, Journal of Bacteriology, (Apr. 2011), vol. 193, No. 8, pp. 2078-2079.

Choi, S. et al., Enzymatic Catalysis of Mercury Methylation by Desulfovibrio desulfuricans LS, Applied and Environmental Microbiology, (Apr. 1994), vol. 60, No. 4, pp. 1342-1346.

Choi, S. et al., Metabolic Pathways Leading to Mercury Methylation in Desulfovibrio desulfuricans LS, Applied and Environmental Microbiology, (Nov. 1994), vol. 60, No. 11, pp. 4072-4077.

Gilmour, C.C. et al., Sulfate-Reducing Bacterium Desulfovibrio desulfuricans ND132 as a Model for Understanding Bacterial Mercury Methylation, Applied and Environmental Microbiology, (Jun. 2011), vol. 77, No. 12, pp. 3938-3951.

Ragsdale, S.W. et al., Moussbauer, EPR, and Optical Studies of the Corrinoid/Iron-Sulfur Protein Involved in the Synthesis of Acetyl Coenzyme A by Clostridium thermoaceticum, the Journal of Biological Chemistry, (Oct. 15, 1987), vol. 262, No. 29, pp. 14289-14297.

Ragsdale, S.W. et al., Acetogenesis and the Wood-Ljungdahl pathway $CO_2$ fixation, Biochimica et Biophysica Acta, (2008), vol. 1784, pp. 1873-1898.

Ragsdale, S.W., Catalysis of Methyl Group Transfers Involving Tetrahydrofolate and B12, Vitam Horm, (2008), vol. 79, pp. 293-324.

Svetlitschnaia, T. et al., Structural insights into methyltransfer reactions of a corrinoid iron-sulfur protein involved in acteyl-CoA synthesis, PNAS, (Sep. 26, 2006), vol. 103, No. 39, pp. 14331-14336.

Hurt, R.A. et al., Sequencing Intractable DNA to Close Microbial Genomes, PLoS One, (Jul. 2012), vol. 7, Issue 7, pp. 1-9.

Parks, J.M. et al., The Genetic Basis for Bacterial Mercury Methylation, Science, (Mar. 15, 2013), vol. 339, pp. 1332-1335.

Ekstrom, E.B. et al., Cobalt Limitation of Growth and Mercury Methylation in Sulfate-Reducing Bacteria, Environ. Sci. Technol., (2008), vol. 42, pp. 93-99.

Brown, S.D. et al., Draft Genome Sequences for Three Mercury-Methylating, Sulfate-Reducing Bacteria, Genome Announcements, (Jul./Aug. 2013), vol. 1, Issue 4, pp. 1-2.

Elias, D. et al., A Multipronged Approach Ranging From Pure Cultures to Microbial Communities to Determine the Mechanism of Mercury Methylation, the 10th International Conference on Mercury as a Global Pollutant (ICMGP), (Jul. 27, 2011).

\* cited by examiner

```
GTG GAC GGC TTC GCC AGG ACG GCG GCC GGT CCG GTG CCG CGC GTG CGC ACC TAT CTG CGC  60
 V   D   G   F   A   R   T   A   A   G   P   V   P   R   V   R   T   Y   L   R   20

CGC GAC GAC CGC GTG GGC GAT CTG CGC GCC CGC CTG GGC ACC AAC CGC CAC GAC TTC AAG 120
 R   D   D   R   V   G   D   L   R   A   R   L   G   T   N   R   H   D   F   K   40

GTG GTG CCT GGC CTG TAC TGC GTG GGC GAG CCC GAC CGG ACC TCG CCG GTC CTG GTC ACC 180
 V   V   P   G   L   Y   C   V   G   E   P   D   R   T   S   P   V   L   V   T   60

GCC AAC TAC AAG CTG ACC TTC GAC ACC CTG CGC GAG CGG CTG ACC TCC ATC GAC GCC TGG 240
 A   N   Y   K   L   T   F   D   T   L   R   E   R   L   T   S   I   D   A   W   80

CTG CTG GTG GTG GAT ACG CGC GGC ATC AAC GTC TGG TGC GCG GCG GGC AAG GGG TTG TTC 300
 L   L   V   V   D   T   R   G   I   N   V   W   C   A   A   G   K   G   L   F  100

ACC GCT TCC GAG GTG GCC TTC AGC GTC AAC GCG GTC CGG CTG CAC CAG GTG GTC GAG CAC 360
 T   A   S   E   V   A   F   S   V   N   A   V   R   L   H   Q   V   V   E   H  120

CGC GAA CTG ATC CTG CCC CAG CTG GCC GCC ACG GGC GTG GCC GCC CGC GAG GTG GAG CGC 420
 R   E   L   I   L   P   Q   L   A   A   T   G   V   A   A   R   E   V   E   R  140

ATC TGC GGC TTC AAG GTC CTA TGG GGC CCC ATC CGG GCC AGG GAC CTG CCC GCC TTC CTG 480
 I   C   G   F   K   V   L   W   G   P   I   R   A   R   D   L   P   A   F   L  160

CGC AAC GGC AAC AAG GCG GAC GAG GCC ATG CGC GGC GTG ACC TTC ACC TTA CGC GAA CGG 540
 R   N   G   N   K   A   D   E   A   M   R   G   V   T   F   T   L   R   E   R  180

GCC GCG CTC ATC CCG GTG GAA CTG TAC CAG CTG CGC AAG CCC CTG TTC GCG GCC ATT CCG 600
 A   A   L   I   P   V   E   L   Y   Q   L   R   K   P   L   F   A   A   I   P  200

CTG CTC TTC CTG CTC TCC GCC CTG GGG CCG GAC CTC TTT TCC CCG CCC GCC CTG TGG CAG 660
 L   L   F   L   L   S   A   L   G   P   D   L   F   S   P   P   A   L   W   Q  220

CGG GGC ATC TCG GCC GTC ACG GCC ACC CTG GTC GGC GCG CTG GCG GGC AGC GTG CTG GTC 720
 R   G   I   S   A   V   T   A   T   L   V   G   A   L   A   G   S   V   L   V  240

CCC CTG TTC CTG AAC AGG CTG CCC TGG CGG CAG TTC TGG CCC AAA GGC GCG CTG GTC GGC 780
 P   L   F   L   N   R   L   P   W   R   Q   F   W   P   K   G   A   L   V   G  260

GGG GCC GCC GGG ACC CTG GCG GCA CTG TAC CTG CCC GTG CAC GGC TGG GCC GAC CCC CTG 840
 G   A   A   G   T   L   A   A   L   Y   L   P   V   H   G   W   A   D   P   L  280

GCC CTG ACG CTC TGG GCC ACG GCC GTG GCC TCC TGG CAG GCC ATG AAT TTC ACG GGC TCG 900
 A   L   T   L   W   A   T   A   V   A   S   W   Q   A   M   N   F   T   G   S  300

ACC CCC TAC ACC TCG CCC TCG GGC GTG GAA AAG GAA ATG CGC CGG GGC ATG CCG CTC CAG 960
 T   P   Y   T   S   P   S   G   V   E   K   E   M   R   R   G   M   P   L   Q  320

GCA CTG GCC GCG CTG GCC GCC GCA GGG CTG TGG CTG GCC GGG CCG TTC CTC GGT TGA    1017
 A   L   A   A   L   A   A   A   G   L   W   L   A   G   P   F   L   G   *      338
```

FIG. 5

```
ATG AAG GAT TTC CGC TAT ATC GAC GGC GTG TCC AGC CTG GCG CTC GAC ACG GAC AAG TGC  60
 M   K   D   F   R   Y   I   D   G   V   S   S   L   A   L   D   T   D   K   C   20

GTG GGC TGC GGG TCC TGC GTG GAC GTC TGC CCG CAC CGC ATC CTG GCC GTG CGG GAG CGC 120
 V   G   C   G   S   C   V   D   V   C   P   H   R   I   L   A   V   R   E   R   40

AAG ACG ACC ATC CTC GAC TTC GAC GCC TGC ATG GAG TGC GGG GCC TGC GCC CGC AAC TGC 180
 K   T   T   I   L   D   F   D   A   C   M   E   C   G   A   C   A   R   N   C   60

CCG GTG GAG GCG ATC ACC GTC ACC CCC GGC ACG GGC TGC GCC GCC TAC CTG GTC TCG GTC 240
 P   V   E   A   I   T   V   T   P   G   T   G   C   A   A   Y   L   V   S   V   80

TGG CTG CAC CGG CTG ACC GGG CGC AAG ATC GAC GCC GCC TGC TGC TAG                 288
 W   L   H   R   L   T   G   R   K   I   D   A   A   C   C   *                   95
```

MERCURY METHYLATION GENES IN BACTERIA AND ARCHAEA

CROSS REFERENCE TO RELATED APPLICATIONS

This application claims benefit of U.S. Provisional Application No. 61/739,302, filed on Dec. 19, 2012, which is incorporated herein by reference in its entirety.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on Dec. 13, 2013, is named 28804_SL.txt and is 60,572 bytes in size.

FIELD OF THE INVENTION

Methylmercury is a potent, bioaccumulative neurotoxin produced by microorganisms from inorganic Hg(II). Two genes required for this conversion have been identified in both bacteria and archaea. These genes are the hgcA gene which encodes a corrinoid protein that facilitates methyl group transfer to Hg, and the hgcB gene which encodes a corrinoid protein-associated ferredoxin with two [4Fe-4S] binding motifs and are involved in generating to cob(I) almin. Both genes have been found in methylating strains but not in non-methylating strains (with available genomic sequences). Their deletion abolished mercury methylation activity in *Desulfovibrio desulfuricans* ND132 and *Geobacter sulfurreducens* PCA and complementation restored activity.

BACKGROUND OF THE INVENTION

Mercury is a pervasive global pollutant which bioaccumulates in the food web and is highly toxic to humans and other organisms. Anaerobic microorganisms, such as sulfate-reducing bacteria (SRB), iron-reducing bacteria and methanogens have been implicated as producers of methylmercury (MeHg). However, phylogenetic analyses based on 16S sequences cannot distinguish between methylating and non-methylating microorganisms (Ranchou-Peyruse 2009; Gilmour 2011; Yu et al. 2012).

Biological mercury methylation was shown to be an enzyme-catalyzed process and proposed to be associated with the reductive acetyl-CoA (Wood-Ljungdahl) pathway (Wood 1968; Choi 1994b). A 40 kDa corrinoid-binding protein capable of methylating mercury was identified in cell extracts of the sulfate-reducing bacterium *Desulfovibrio desulfuricans* LS—a methylating SRB strain. Unfortunately, the strain was lost and further characterization of that 40 kD protein is not possible (Gilmour 2011). Although mercury methylation activity was proposed to be associated with the reductive acetyl-CoA (Wood-Ljungdahl) biochemical pathway (Choi et al. 1994a), no consistent relationship was ever established between that pathway and the ability to methylate Hg(II), suggesting the existence of an alternative, but as yet unidentified, pathway or pathways to form MeHg in microorganisms (Ekstrom 2003).

Accordingly, the need remained to understand the genetic and biochemical basis for microbial mercury methylation and to identify specific microorganisms with the potential to methylate mercury. The availability of the complete genome sequences for known mercury methylators and non-methylators aided the discovery, identification and characterization of two genes and their gene products, associated with a mercury methylation pathway common to all known methylating bacteria and archaea sequenced to date. Characterization of these gene products explains mercury methylation in microorganisms whether or not the complete acetyl-CoA pathway is present in those microorganisms. Moreover, the availability of the genes provides a biomarker for microbial mercury methylation that can be used to identify methylators as well as to assess the mercury methylation potential.

SUMMARY OF THE INVENTION

The present invention is directed to isolated nucleic acids for hgcA or hgcB, genes that encode products that catalytically cycle to methylate mercury. In particular, the isolated nucleic acids include, but are not limited to, contiguous nucleotides for hgcA shown in FIG. 5, a nucleotide sequence encoding the amino acid sequence for HgcA shown in FIG. 5, a nucleotide sequence encoding an amino acid sequence for HgcA from any one of the microorganisms listed in Table 1, or a consensus nucleotide sequence that detects hgcA from microorganisms capable of mercury methylation.

The isolated nucleic acids of the invention also include, but are not limited to, contiguous nucleotides for hgcB shown in FIG. 6, a nucleotide sequence encoding the amino acid sequence for HgcB shown in FIG. 6, a nucleotide sequence encoding an amino acid sequence for HgcB from any one of the microorganisms listed in Table 1, or a consensus nucleotide sequence that detects hgcB from microorganisms capable of mercury methylation. The nucleic acids can be PCR primers, sequencing primers, hybridization probes, gene cassettes and the like.

In some embodiments of the invention, the nucleic acids are PCR primers. In such embodiments, the invention provides one or more sets of PCR primers capable of amplifying from at least about 20-25 bp to all of a microbial hgcA gene, including those listed in Table 1, wherein gene, as used herein, includes upstream and downstream regions associated with expression of the hgcA coding sequence. In alternative embodiments, the invention provides one or more sets of PCR primers capable of amplifying from at least about 20-25 bp to all of a microbial hgcB gene, including those listed in Table 1. Again, "gene" includes upstream and downstream regions associated with expression of the hgcB coding sequence.

The invention also relates to isolated recombinant expression vectors which comprise an hgcA coding sequence operably linked to a heterologous promoter, microbial cells containing that expression vector and methods of using the vector to produce HgcA by (a) culturing those cells for a time and under conditions to allow the vector to express HgcA and (b) recovering the HgcA protein. Similar recombinant expression vectors, cells and methods of use are provided for HgcB expression and for domains of HgcA or HgcB. For example, the invention includes recombinant expression vectors for production of the cobalamin-binding domain of HgcA and for mutant cobalamin-binding domains (exemplified, for example, by the C93T mutant cobalamin-binding domain in Example 4).

In further aspects of the invention, the HgcA and HgcB proteins can be used to produce and isolate polyclonal antibodies, monoclonal antibodies or immunospecific fragments thereof. Such antibodies can be used, for example, in a method to detect HgcA protein, HgcB protein or both proteins by assaying a sample for the presence of one or both of those proteins via an immunoblot, an ELISA, immunohistochemical staining and or other immunodetection technique. This method can be used, e.g., with environmental samples or with cultures of microorganisms.

Yet another aspect of the invention relates to a method to detect microorganisms capable of mercury methylation in a sample by (a) preparing nucleic acids from a sample and (b) detecting the presence of an hgcA gene, an hgcB gene, or both. In some embodiments, the sample is hybridized with one or more nucleic acid probes or primers specific for hgcA, hgcB or both and hybridization is detected by any convenient method, including, but not limited to, microarray-based assays, PCR assays, in situ hybridizations, Southern blots, or Northern blots. Any type of PCR assay can be used, including RT-PCR-based assays. The samples can be from the environment or from a clinical, microbiome-containing sample. This method can, optionally, be combined with hybridization-based methods to identify the species of microorganism in the sample.

In another method of the invention, microorganisms capable of mercury methylation can be detected by (a) preparing nucleic acids from an environmental sample and (b) sequencing that nucleic acid, in whole or in part, to detect the presence of an hgcA gene, an hgcB gene or both in the sample. In this method the nucleic acid can optionally be preselected to be specific for particular microorganisms known to methylate mercury (or to have the capacity to methylate mercury) amplified with one or more primers specific for hgcA, or hgcB or both, followed by sequencing to identify the presence of hgcA, hgcB or both in the sample.

In either of the foregoing two methods, the initial amount, or relative initial amount, of nucleic acid in the sample can be quantitatively assayed to determine the mercury methylation potential, or relative mercury methylation potential of the sample.

The present invention also provides kits for the use with any of these methods. In general, kits include probes, primers, antibodies or immunospecific fragments specific for hgcA, hgcB or both, and reagents sufficient to conduct assays to detect (qualitatively or quantitatively) hgcA, hgcB, or both, using the hgcA- or hgcB-specific reagents. For example, in one embodiment, a screening kit for detecting microorganisms capable of methylating mercury comprises (a) one or more hgcA- or hgcB-specific oligonucleotides, or both, that can be used (i) to amplify nucleic acid obtained from an environmental sample, (ii) to identify nucleic acid in the sample, or amplified from the sample, or (iii) to enable sequencing of the nucleic acid in the sample, or amplified from the sample, and reagents for conducting said screening. In some embodiments, the one or more oligonucleotides are adapted for use in a microarray format for identifying hgcA or hgcB, for a PCR assay, or for sequencing all or a portion of hgcA or hgcB-containing nucleic acid.

In yet a further aspect, the invention relates to a method of biocatalysis which comprises (a) preparing a reaction mixture comprising a methyl donor and sufficient HgcA to act as a biocatalyst in a reaction for (enantioselective) synthesis involving methyl transfer to an electrophilic organic or metal acceptor in aqueous solution.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 lists the nucleotide and amino acid sequence of *D. desulfuricans* ND132 hgcA, SEQ ID NOS. 2 and 3, respectively.

FIG. 6 lists the nucleotide and amino acid sequence of *D. desulfuricans* ND132 hgcB, SEQ ID NOS. 4 and 5, respectively.

FIG. 8B is an expanded view of the Proteobacteria shown in the bottom panel of FIG. 8A.

FIG. 8C is an expanded view of the Firmicutes and Euryarcheota shown in the bottom panel of FIG. 8A.

FIG. 9A discloses the sequences in the left column as SEQ ID NOS. 111-156, respectively, in order of appearance, the sequences in the middle column as SEQ ID NOS. 157-202, respectively, in order of appearance and "SCCG" in the right column as SEQ ID NO: 203.

FIG. 9B is an expanded view of the Proteobacteria shown in the bottom panel of FIG. 9A.

DETAILED DESCRIPTION OF THE INVENTION

A. Overview

The characterization of the genes and proteins responsible for mercury methylation, particularly in *D. desulfuricans* ND132 and *G. sulfurreducens* PCA, coupled with the extensive microbial sequence information available, enabled the identification of biomarkers, including quantifiable biomarkers, for assessing microbial mercury methylation potential. These biomarkers allow determination of direct and indirect environmental parameters that influence the degree, rate and extent of microbial methylmercury production in the environment and may inform targeted strategies for mitigating methylmercury production. The biomarkers can also be used to identify the microorganisms capable of mercury methylation, for example, as may occur in the microbiome, clinical samples, or as may be found in other sources. As used herein, "mercury methylation potential" is a measure of the capacity of a sample to produce methyl mercury. As such, it qualitatively reflects whether microorganisms capable of methylating mercury are present in a sample and, when measured quantitatively, can be used to determine how much methyl mercury can be produced in a sample or can be correlated to the number of microorganisms capable of methylating mercury present in a sample.

Figure 1:
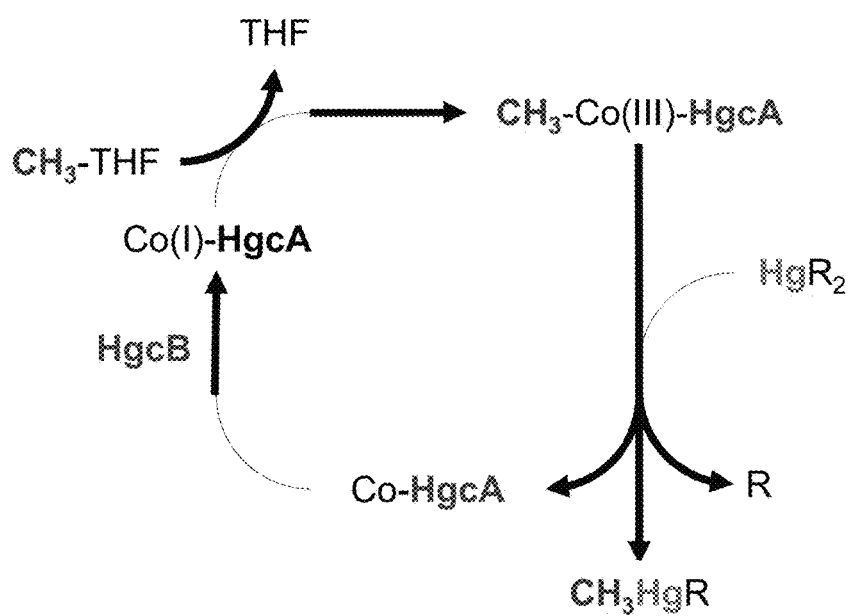
FIG. 1 depicts a mercury methylation cycle for bacteria and archaea. In this scheme, the methyl group originates from $CH_3$-THF and is transferred to cob(I)alamin-HgcA [Co(I)-HgcA] to form $CH_3$Co(III)-HgcA. Attack of a methyl group on $HgR_2$ produces $CH_3HgR$ and cobalamin-HgcA [Co-HgcA]. The turnover cycle completes after HgcB regenerates Co(I)-HgcA. Abbreviations: THF, tetrahydrofolate.
Figure 2:
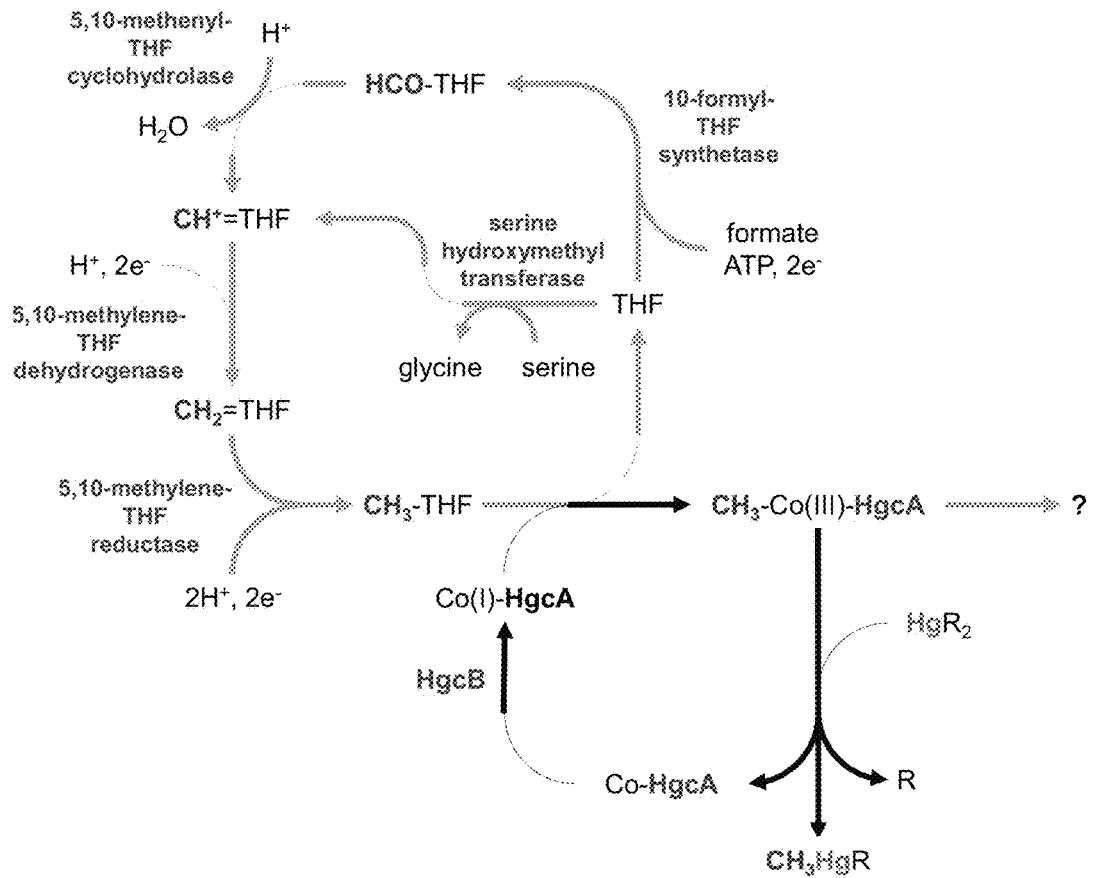
FIG. 2 is an expanded version of the mercury methylation cycle (bold loop) in FIG. 1 showing its relationship to the reductive acetyl-CoA pathway (grey loop) and the potential sources of methyl groups.

Prior to this invention, no specific gene or genes required for methylation of mercury had been identified. With this invention, the inventors identified two genes whose gene products are essential for mercury methylation in bacteria and archaea, facilitating methylation by a corrinoid-dependent protein and associated ferredoxin, regardless of whether or not the microbe also encodes a complete reductive acetyl-coA pathway (FIG. 1). As shown and without being bound to a mechanism, a methyl group originating from $CH_3$-THF (or other source) is transferred to Co(I)-HgcA to form $CH_3Co(III)$-HgcA followed by methyl transfer to a Hg(II) substrate (likely as a carbanion or as methyl radical) to produce methylmercury. The turnover is complete when HgcB catalyzes the reduction of the corrinoid factor to regenerate Co(I)-HgcA. FIG. 2 shows an expanded version of this mercury methylation cycle and its expected relationship to the methyl branch of the reductive acetyl-CoA pathway.

Accordingly, as disclosed herein, the genes involved in microbial mercury methylation are hgcA and hgcB. These genes and their gene products provide biomarkers for assessing environmental mercury methylation potential as well as identifying the microorganisms generating that potential, which in turn can aid in environmental mercury remediation and studies related to human health.

B. Nucleic Acids

The present invention relates to isolated nucleic acids from microbial hgcA and hgcB genes. A list of 46 sequenced microbial strains identified so far having hgcA and hgcB genes is provided in Table 1, along with the locus tag designations for hgcA and hgcB in each strain. The isolated nucleic acids of the invention include hgcA and/or hgcB from each of these strains as well as from any other microbial strains having hgcA and/or hgcB orthologs. For example, such other strains can be identified by sequencing and BLAST analysis of sequence data with any of the known hgcA or hgcB gene sequences, by hybridization of microorganismal DNA (or RNA) with hgcA or hgcB specific probes, or by PCR amplification of microbial DNA (or RNA) with hgcA or hgcB specific primers using techniques known in the art.

The isolated nucleic acids of the invention include but are not limited to, nucleic acids comprising a microbial hgcA gene, a microbial hgcB gene, or both, (which can include none, some or all of the cis-acting, transcription and expression control elements associated with the coding sequences of those genes); nucleic acids comprising the coding sequence of a microbial HgcA protein, a microbial HgcB protein, or both; expression vectors comprising a nucleic acid encoding a microbial HgcA protein, a microbial HgcB protein, or both, with or without a heterologous promoter operably linked thereto; nucleic acids of a size suitable for use as probes to detect one or more microbial hgcA genes, microbial hgcB genes, or both (typically these probes comprise from at least 14-15 nucleotides to about 50 nucleotides of contiguous hgcA or hgcB nucleotides or comprise one or more restriction fragments from a microbial hgcA or hgcB gene); and nucleic acids of a size suitable for use as primers to amplify a nucleotide fragment specifically associated with (such as an upstream or downstream region) or containing all or part of a microbial hgcA coding sequence, hgcB coding sequence, or both. The primers include PCR primers and sequencing primers. PCR primers are typically provided as forward and reverse primers, but can also be provided singly for combination with universal primers. Primer size can be varied and typically have from as few as 8-12 to as many as 20-30 contiguous hgcA- or hgcB-associated nucleotides, the size of which can readily be determined by those of skill in the art based on the purpose of the primer (PCR, sequencing, etc.). The size of fragments targeted for amplification by primers of the invention depends on the purpose for the amplification, and can range from small fragments of 15-100 bp (e.g., to clone particular sequence elements, to create mutations) to large fragments of 0.5 to 2 kb (e.g., to clone full or partial coding sequences, with or without the associated upstream and downstream sequences). Examples of PCR primers and primer sets are listed in Table 6.

Primers and probes, as well as the other nucleic acids of the invention, can be labeled with detectable markers such as enzymes, small molecules (e.g., biotin, fluorophores), and may include other nucleotides to facilitate detection, cloning, sequencing, PCR or other analysis (e.g., a primer can have a restriction site added at one end, or include barcode sequences for next generation sequencing techniques and the like).

In some embodiments, the nucleic acids of the invention comprise contiguous nucleotides from the nucleotide sequence for hgcA shown in FIG. 5 (from *D. desulfuricans* ND 132), a nucleotide sequence encoding the amino acid sequence for hgcA shown in FIG. 5, a nucleotide sequence encoding an amino acid sequence for hgcA from any one of the microorganisms listed in Table 1, or a consensus nucleotide sequence that specifically detects hgcA in microorganisms capable of mercury methylation. In each case, the contiguous nucleotides have a length sufficient to detect hgcA, amplify hgcA, specifically prime sequencing of hgcA and the like, consistent with the purpose or intended use of the nucleic acid as a probe, primer, and the like.

In certain embodiments, the contiguous nucleotides more specifically comprise nucleotides 256-300 shown in FIG. 5 or the equivalent nucleotides from any one of the microorganisms listed in Table 1. In some embodiments, the contiguous nucleotides more specifically comprise the nucleotides that encode amino acids 86-100 shown in FIG. 5 or the equivalent nucleotides from any one of the microorganisms listed in Table 1. In other embodiments, the contiguous nucleotides encode the consensus amino acid sequence N[V/I]WCA[A/G]GK (SEQ ID NO. 6) or TxG[I,V]N[V,I]WCA[A,G]GK[G,D,K,Q]xF, where x is any amino acid and amino acids in brackets represent alternative choices for the given position (SEQ ID NO. 8). Each of these embodiments can be further modified (e.g., to have detectable moieties) or contain additional nucleotides (to simplify detection, for PCR, for sequencing and the like). Among other uses, the nucleic acids comprising consensus sequences are particularly suited to be biomarkers for hgcA. However, any microbial-specific sequence of hgcA can serve as a biomarker for mercury methylation capacity or potential.

For hgcB, the isolated nucleic acids comprise contiguous nucleotides from the nucleotide sequence shown in FIG. 6, a nucleotide sequence encoding the amino acid sequence for hgcB shown in FIG. 6, a nucleotide sequence encoding an amino acid sequence for HgcB from any one of the microorganisms listed in Table 1, or a consensus nucleotide sequence that detects hgcB in microorganisms capable of mercury methylation. In each case, the contiguous nucleotides have a length sufficient to detect hgcB, amplify hgcB, specifically prime sequencing of hgcB and the like, consistent with the purpose of the intended use of the nucleic acid as a probe, primer, and the like.

In certain embodiments, the contiguous nucleotides from hgcB more specifically comprise nucleotides 58-90 or 148-180 shown in FIG. 6 or the equivalent nucleotides from any one of the microorganisms listed in Table 1. In some embodiments, the contiguous nucleotides more specifically comprise the nucleotides that encode amino acids 20-30 or 50-60 shown in FIG. 6 or the equivalent nucleotides from any one of the microorganisms listed in Table 1. These embodiments, as well as any microbial-specific sequence of hgcB are particularly suited to be biomarkers for hgcB and thus serve as a biomarker for mercury methylation capacity or potential.

Nucleic acids include DNA and RNA as well as chemical modifications (e.g., base or sugar modifications) and variants thereof, whether as polynucleotides or oligonucleotides.

The nucleic acids of the invention can be isolated from microorganisms or can be chemically synthesized. Methods for isolating nucleic acids from microorganisms and synthetic methods for making oligonucleotides, including probes, primers, molecular beacons, PNAs, LNAs (locked nucleic acids), etc., are well known to those of skill in the art.

The present invention also includes expression vectors which comprise any of the nucleic acids of the invention, but generally encode the entire protein sequence or a particular domain of the protein. In particular, these embodiments include expression vectors in which the coding sequence for hgcA or hgcB is operably linked to a heterologous promoter, or expression vectors in which the coding sequence for hgcA or hgcB remains operably linked to its native promoter. Expression vectors include plasmids, cosmids, viral vectors, artificial chromosomes and the like. Expression vectors can be extrachromosomal or can be integrated into the genome of an organism.

Methods for making and using isolated nucleic acids and expression vectors are well known in the art, for example, as described in Green & Sambrook (2012) Molecular Cloning: A Laboratory Manual, 4th Ed., Cold Spring Harbor Press, Cold Spring Harbor, N.Y. and its earlier editions. Likewise methods for designing and using nucleic acid probes and primers are also well known to those of skill in the art (see, for example, Innis and Gelfand, eds. (1999) PCR Methods Manual (Academic Press, New York or other texts).

C. Methods of Using Nucleic Acids of the Invention

The nucleic acids, probes, primers and expression vectors of the invention have a variety of uses relating to detecting and expressing hgcA and hgcB genes.

In some embodiments, recombinant expression vectors of the invention are used to transform microbial cells and to express HgcA, HgcB or both (for example, the two genes can be linked under control of a single operon). Accordingly, this invention includes microbial cells which comprise an expression vector of the invention. Such expression vectors include, but are not limited to, those which encode the complete protein HgcA, the complete HgcB protein or a domain thereof such as the corrinoid-binding domain of HgcA (amino acids 1-166 of the HgcA from *D. desulfuricans* ND132 or the analogous coding sequence from any of the strains listed in Table 1).

The microbial cells of the invention can include any strain used for expressing proteins such as *E. coli* and *Salmonella* spp. as well as others such as *D. desulfuricans, G. sulfurreducens*. Further, the microbial cells of the invention may be the same strain as the hgcA or hgcB gene that is being expressed. For example, if the expression vector encodes hgcA from *D. desulfuricans* ND 132, the microbial cell can be *D. desulfuricans* ND 132. Similarly, other constructs and microbial cells can be paired for protein expression.

Accordingly, another aspect of the invention provides a method of producing HgcA protein, HgcB protein, or both, by culturing a microbial cell of the invention for a time and under conditions sufficient for the vector to produce such protein. Methods of gene expression are well known in the art, see, e.g., Green & Sambrook (2012). Expression methods can use either constitutive or inducible promoters. With an inducible promoter, the cells are grown for a length of time, the promoter is induced (often with a small molecule or by a temperature shift) and the cells are cultured for another period of time to allow protein expression. Thereafter, the cells are harvested and the expressed protein (or protein domain) is recovered. The expressed products may or may not exhibit methylation activity. Inactive protein, for example, can be used for raising antibodies. Methods for protein purification and isolation are within the ken of those of skill in the art.

Yet a further aspect of the invention is directed to a method for detecting and identifying microorganisms capable of mercury methylation. In this method, nucleic acid can be extracted from a sample of the microorganism to be tested. In some instances the microorganism is isolated first or may be part of a mixture of microorganisms. The samples analyzed by these methods can be from any source, such as an unknown culture, a mixed microbial culture, a food sample, a clinical sample or an environmental sample.

The nucleic acid can be extracted as RNA or DNA, and if RNA is isolated, it can be converted to cDNA before further analysis. Typically the nucleic acids are extracted as DNA which is then analyzed by a hybridization technique such as Southern blotting (or Northern blotting, if RNA is extracted), in situ hybridization, PCR, sequencing and the like. The nucleic acid can also be analyzed by directed sequencing, where primers specific for hgcA or hgcB nucleic acid are used to capture nucleic acids, which are in turn directly sequenced.

When necessary, the nucleic acids can be amplified before detection. Additional detection methods include RT-PCR such as found in the BAX system (DuPont), deep sequencing, next generation sequencing, arrays and more. Detection methods are well known in the art. One of skill in the art can determine the appropriate primers for amplifying the hgcA/hgcB nucleic acid. A myriad of amplification and sequencing techniques are known and available in the art (see, e.g., focused genotyping, bead chips, and the next generation sequencing provided by Illumina or the 454 pyrosequencing provided by Roche), and any combination can be performed.

In one embodiment, the extracted nucleic acid can be hybridized to a microarray that contains probes specific for hgcA or hgcB, or both, from the sequences of known or suspected methylator strains (such as those listed in Table 1) or from a consensus sequence for one or both of these genes.

Additionally, the microarray can contain probes for the 16S RNA of the companion microorganisms (or other species-specific probe) to confirm identity (or to identify) the microorganism. In other words, if the microarray has a probe for hgcA DNA from *D. desulfuricans* ND132 and *G. sulfurreducens* PCA, then the microarray can also have a probe for the 16S RNA of those same two species. Further, in an embodiment designed to widely identify microorganisms having hgcA and hgcB (so to assess mercury methylation capability), the microarray can have one or more consensus sequence probes for those genes and a multiplicity of 16S RNA probes that can be used to identify the species of microorganism being tested. The multiplicity of 16S probes can number in the hundreds within the capacity of the microarray. For example, the 16S probes can include representative species expected to have mercury methylation capacity (e.g., some or all of those listed in Table 1 and other species once identified) as well as species that may not be capable of mercury methylation (but that might be found in an environmental or clinical sample) or that may serve as controls.

Additionally, some embodiments of this invention relate to detecting the mercury methylation potential in an environmental or clinical sample. The mercury methylation potential can provide a quantitative measure of the enzymatic capacity of microorganisms present in a sample to convert inorganic Hg(II) to $CH_3$—Hg. Hence, the greater the number of microorganisms with hgcA and hgcB genes in a sample, the greater the mercury methylation potential. The mercury methylation potential can be measured by assessing the number of microbial genomes present in a sample (detecting DNA) or by detecting and assessing gene expression activity (detecting mRNA). In either case, the level of the nucleic acid is directly proportional to the mercury methylation potential of the sample.

A variety of sampling strategies are available. For clinical samples, a swab, tissue or bodily fluid (e.g., saliva, blood, urine) sample can be obtained and processed using techniques known in the art, allowing one to assess the microbiome of humans and animals for the presence of methylators or for methylmercury potential. For example, in some instances, it may be advantageous to culture the organisms present in a clinical sample before analysis by the methods of the invention. In other instances, the sample may be used directly (or with minimal processing) in a method of the invention. Similarly, a food sample or lab culture can be obtained for use in methods of the invention.

For environmental samples, methylmercury production is known to occur anaerobically in saturated soils, wetlands, decaying periphyton mats, aquatic bottom sediment and anaerobic bottom waters. Hence, water and sediment samples are collected for qualitative and quantitative determination of the presence of microbes capable of mercury methylation. Any water source can be sampled, including but not limited to, seawater, lake water, pond water, wetlands, river water, streams, standing water and the like. Sediment samples can be obtained from any of the water sources and can be obtained from the surface or at depth. The identity and mercury methylation potential of microorganisms present in surface sedimentations are of particular interest. If necessary, the water and sediment samples can be obtained and maintained anaerobically. Techniques for obtaining water and sediment samples are known in the art. The volume of sample to be collected may vary depending on the analytical technique being used for detection and quantitation of the microbes. Volume samples can be concentrated for convenience.

The samples can be subject to size fractionation, which generally provides for different sets of organisms for analysis. For example, it may be advantageous to remove smaller viral material, or larger protists and zooplankton before analyzing the sample for the presence of microbes. Size fractionation can be achieved by using appropriate filtering techniques. The microbes of interest for identification and analysis generally range from about 0.1 to about 7 µm in size.

Once a working sample is obtained, it can be treated to extract DNA, RNA or protein using any of the myriad of techniques known in the art, including kits therefor. For example, generally, the sample is treated to lyse cells, the debris is removed and the DNA, RNA, or both, is recovered. The RNA can be converted to cDNA before analysis. Similar, if being tested, the protein in the sample can be analyzed. Since hgcA is predicted to encode a transmembrane domain, the cellular membrane fraction can be used for analysis, e.g., in an immunoblot.

Samples are analyzed by the various techniques in accordance with the methods of the invention, including but not limited to, immunological techniques, microarray analysis, molecular finger-printing, PCR, transcriptome analysis, and any of the multitude of DNA sequencing techniques available (including next generation sequencing, deep sequencing) to ascertain the presence and quantity of genes and gene products (protein or RNA) from hgcA, hgcB, or both, in the microorganisms or any nucleic acid present in the sample using the primers, probes and/or antibodies of the invention. The formats of the assays can be configured for high-throughput analysis. The analyses for hgcA/hgcB in an environmental sample can be combined with analyses for other characteristics pertinent to microorganism capable of methylating mercury, such as assessing the sample for the type of microorganisms (e.g., examining the diversity of microorganisms). For example, additional biomarkers any kits or tests of the invention can optionally include components for distinguishing whether the microorganisms are sulfate-reducing bacteria (SRB), iron-reducing bacteria and methanogens (archaea).

D. Antibodies and Protein Detection Methods

As another method for detecting HgcA, HgcB, or both, antibodies can be prepared for these proteins and used in immunodetection techniques to analyze whether samples contain one or more of these proteins. The samples are obtained as described above for nucleic acid detection methods (in Section C).

Hence, HgcA and HgcB proteins can be produced in accordance with the invention, isolated and used to prepare polyclonal antibodies or monoclonal antibodies using techniques known in the art. The genes for such antibodies can also be identified using conventional techniques. With the antibodies, immunospecific fragments thereof can be prepared by enzymatic methods. With the genes, immunogenic fragments can also be prepared by recombinant techniques known in the art.

The antibodies of the invention can be used, for example, in a method to detect HgcA protein, HgcB protein or both proteins by assaying a sample for the presence of one or both of those proteins via an immunoblot, an ELISA, immunohistochemical staining and or other immunodetection technique. Such techniques are well known in the art and such methods can be used with, e.g., environmental samples, clinical samples, food samples, cultures of microorganisms and the like.

E. Kits

A further aspect of the invention is directed screening kits for mercury methylators and for detecting mercury methylation potential in accordance with the methods of the invention. Such kits can take many forms, for example, one type of kit is designed for sequencing nucleic acid obtained from an environmental sample and/or a clinical sample. Such a kit can contain hgcA- or hgcB-specific primers (or both) to amplify the nucleic acid (either RNA or DNA) and further primers to sequence the RNA or DNA depending on the sequence technique to be used. Sequencing techniques are well known in the art, and include Sanger sequencing, 454 deep sequencing, next-generation sequencing and more. In another embodiment, the screening kit can be in a microarray format designed for detection of hgcA or hgcB DNA or RNA. In another embodiment, the screening kit can be in an ELISA format for detection of HgcA or HgcB protein (or both). Any of these kits can be combined with detection of other biomarkers or other microbial identifiers (such as 16S RNA markers).

F. Biocatalysis

The invention is further directed to a method of biocatalysis which comprises preparing an aqueous reaction mixture comprising a methyl donor, an electrophilic organic or metal acceptor, and sufficient HgcA to act as a biocatalyst for (enantioselective) synthesis, and allowing said reaction to proceed. Suitable methyl donors include but are not limited to, $CH_3$-THF, methyl iodide, low-potential electron donors such as a redox mediator combined with an electrode poised to provide a low potential or, in another embodiment, with photoreduction of a natural or synthetic dyes, e.g. flavins. Unlike conventional substitution reactions, which require an aprotic organic solvent, this biocatalysis can be performed in aqueous solution under anaerobic conditions.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications or other documents cited are herein incorporated by reference in their entirety.

EXAMPLE 1

Identification of Hg Methylation Genes

The corrinoid iron-sulfur protein (CFeSP) from *Moorella thermoacetica* (Ragsdale 1987, Kung 2012) and *Carboxydothermus hydrogenoformans* (Svetlitchnaia 2006, Goetzl 2011) transfers a methyl group to its substrate acetyl-CoA synthase as a carbocation ($CH_3^+$) (Banerjee 2003), suggesting that a similar corrinoid protein might stabilize the Co(III) state, enabling transfer of a methyl group to a Hg(II) substrate to yield methylmercury.

A BLAST search was performed according to Altschul (1997) using the 445 amino acid sequence of the large subunit of CFeSP from *C. hydrogenoformans* Z-2901 (CsfA; locus tag CHY_1223) (see also, UniProtKB: Q3ACS3; GenBank: ABB14598.1) against the translated genome sequence of the confirmed methylator *D. desulfuricans* ND132. The search yielded a partial match in a single gene with a sequence identity of 28% (51% similarity) for the C-terminal residues 306-441 of CFeSP (FIG. 3) with the gene in *D. desulfuricans* ND132 corresponding to record EGB14269.1, locus tag DND132_1056. Of note, the DND132_1056 encoded protein lacks both the TIM barrel domain and the C-terminal [4Fe-4S] binding motif of CfsA. The C-terminal region showed no detectable similarity to any proteins of known structure, but exhibited features characteristic of a transmembrane domain.

The DND132_1056 gene encodes a 338 amino acid protein with a calculated molecular weight, when combined with a cobalamin cofactor, of approximately 38 kDa, similar to the lost 40 kDa corrinoid protein (Choi 1994b). This gene and its orthologs are designated as hgcA.

Further BLAST searches using the ND132 hgcA gene against all available non-redundant CDS translations accessible through NCBI and EMBL-EBI revealed a total of 46 unique genes covering more than 50% of the query sequence with sequence identities in the range of 40-79% and E-values from $2 \cdot 10^{-36}$ to $4 \cdot 10^{-147}$ (as of September 2012). These strains, with their corresponding locus tags, are listed in Table 1.

Figure 4:
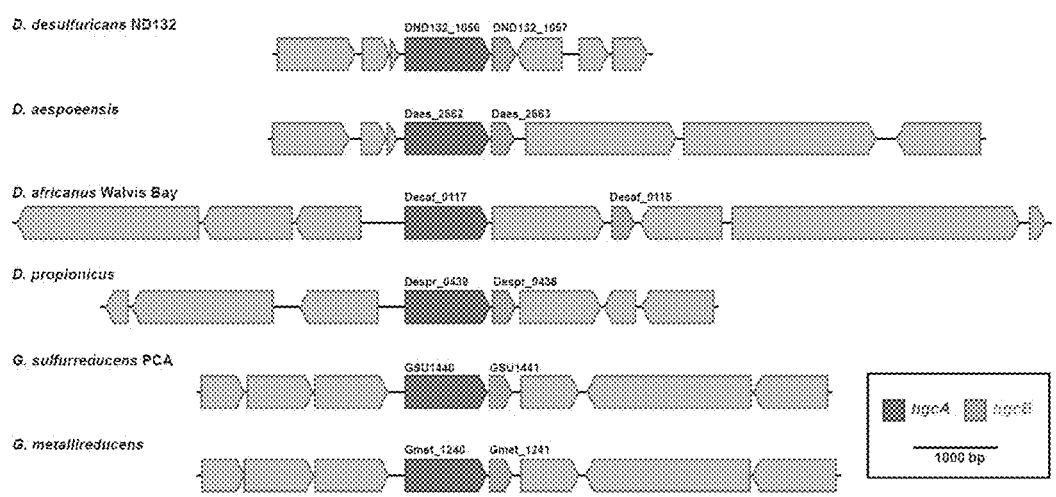
FIG. 4 depicts the mercury methylation gene cluster encoding hgcA and hgcB and surrounding genome from six confirmed mercury methylators with sequenced genomes.

Additional sequence analysis revealed that hgcA is part of a two-gene cluster found in *D. desulfuricans* ND132 and *G. sulfurreducens* PCA as well as other confirmed methylators (FIG. 4; Table 2). This second gene is designated hgcB and appears to be an [4Fe-4S] ferredoxin that works in tandem with hgcA to achieve mercury methylation.

The hgcA-hgcB gene cluster is present in 46 strains, including six confirmed methylators with fully sequenced genomes (Tables 1 and 2). The remaining strains listed in Table 1 can be tested for mercury methylation activity in accordance with the present invention. Further, the gene pair is absent in the eight confirmed non-methylating bacteria with sequenced genomes (Table 3).

The nucleotide and amino acid sequences for hgcA and hgcB from *Desulfovibrio desulfuricans* ND132 are shown in FIGS. 5 and 6, respectively. Underlined sequences are highly conserved. These genes are designated by NCBI Reference Sequence NC_016803.1. The nucleotide sequence and corresponding protein sequence for hgcA is provided as SEQ ID NO. 2 and SEQ ID NO. 3, respectively.

The nucleotide sequence and corresponding protein sequence for hgcB is provided as SEQ ID NO. 4 and SEQ ID NO. 5, respectively.

Based on the data from 46 strains listed in Table 1, the consensus sequence for the cobalamin-binding domain in HgcA is TxG[I,V]N[V,I]WCA[A,G]GK[G,D,K,Q][T,L,S,A]F, where any one of the amino acids given in the brackets appears at the bracketed position, and x is any amino acid (SEQ ID NO. 204).

The genes for the cobalamin-binding protein and its associated ferredoxin-like protein are sporadically distributed among closely related organisms in two phyla of bacteria (Proteobacteria and Firmicutes) as well as in a dissimilar phylum of archaea (Euryarchaeota). At the class taxonomic level, organisms possessing the two-gene mercury methylation cluster, hgcAB, include 23 strains of Deltaproteobacteria (both SRB and FeRB), 13 Clostridia, one Negativicutes, and nine Methanomicrobia.

TABLE 1

Microbial Strains with hgcA and hgcB Genes

| Strain | Phylum | Class | Locus tags (hgcA, hgcB) |
|---|---|---|---|
| *Desulfovibrio desulfuricans* ND132 | Proteobacteria | Deltaproteobacteria | DND132_1056, DND132_1057 |
| *Desulfovibrio aespoeensis* Aspo-2 | Proteobacteria | Deltaproteobacteria | Daes_2662, Daes_2663 |
| *Desulfovibrio africanus* str. Walvis Bay ATCC 19997 | Proteobacteria | Deltaproteobacteria | Desaf_0117, Desaf_0115 |
| *Desulfomicrobium baculatum* X DSM 4028 | Proteobacteria | Deltaproteobacteria | Dbac_0376, Dbac_0375 |
| *Desulfonatronospira thiodismutans* ASO3-1 | Proteobacteria | Deltaproteobacteria | Dthio_PD1043, Dthio_PD1042 |
| *Desulfonatronum lacustre* Z-7951 DSM 10312 | Proteobacteria | Deltaproteobacteria | DeslaDRAFT_0127, DeslaDRAFT_0126 |
| *Desulfovibrio oxyclinae* DSM 11498 | Proteobacteria | Deltaproteobacteria | B149DRAFT_02526, B149DRAFT_02527 |
| *Desulfobulbus propionicus* 1pr3 DSM 2032 | Proteobacteria | Deltaproteobacteria | Despr_0439, Despr_0438 |
| uncultured *Desulfobacterium* sp. | Proteobacteria | Deltaproteobacteria | N47_A07900, N47_A07910 |
| *Geobacter sulfurreducens* PCA DSM 12127 | Proteobacteria | Deltaproteobacteria | GSU1440, GSU1441 |
| *Geobacter metallireducens* GS-15 | Proteobacteria | Deltaproteobacteria | Gmet_1240, Gmet_1241 |
| *Geobacter sulfurreducens* DL-1/KN400 | Proteobacteria | Deltaproteobacteria | KN400_1466, KN400_1468 |
| *Geobacter metallireducens* RCH3 | Proteobacteria | Deltaproteobacteria | GeomeDRAFT_0749, GeomeDRAFT_0748 |
| *Geobacter daltonii* FRC-32 | Proteobacteria | Deltaproteobacteria | Geob_2483, Geob_2482 |
| *Geobacter* sp. M18 | Proteobacteria | Deltaproteobacteria | GM18_1031, GM18_1032 |
| *Geobacter* sp. M21 | Proteobacteria | Deltaproteobacteria | GM21_3091, GM21_3090 |
| *Geobacter uraniireducens* Rf4 | Proteobacteria | Deltaproteobacteria | Gura_0480, Gura_0481 |
| *Geobacter bemidjiensis* Bem | Proteobacteria | Deltaproteobacteria | Gbem_1183, Gbem_1184 |
| *Syntrophorhabdus aromaticivorans* UI | Proteobacteria | Deltaproteobacteria | SynarDRAFT_0655, SynarDRAFT_0656 |
| *Desulfomonile tiedjei* DCB-1 DSM 6799 | Proteobacteria | Deltaproteobacteria | Desti_1022, Desti_1023 |
| *Syntrophus aciditrophicus* SB | Proteobacteria | Deltaproteobacteria | SYN_00351, SYN_00352 |
| delta proteobacterium MLMS-1 | Proteobacteria | Deltaproteobacteria | MldDRAFT_0620, MldDRAFT_0621; MldDRAFT_2280, MldDRAFT_2279 |
| delta proteobacterium NaphS2 | Proteobacteria | Deltaproteobacteria | NPH_5533, NPH_5534 |
| *Acetivibrio cellulolyticus* CD2 | Firmicutes | Clostridia | AcelC_020100000280, AcelC_020100000285 |
| *Dehalobacter restrictus* DSM 9455 | Firmicutes | Clostridia | Dehre_1982, Dehre_1981 |
| *Desulfitobacterium dehalogenans* ATCC 51507 DSM 9161 | Firmicutes | Clostridia | Desde_2772, Desde_2771 |
| *Desulfitobacterium dichloroeliminans* LMG P-21439 | Firmicutes | Clostridia | Desdi_0780, Desdi_0781 |
| *Desulfitobacterium metallireducens* DSM 15288 | Firmicutes | Clostridia | Desme_1742, Desme_1741 |
| *Desulfitobacterium* PCE1 DSM 10344 | Firmicutes | Clostridia | DesPCE1DRAFT_2748, DesPCE1DRAFT_2747 |
| *Desulfosporosinus acidiphilus* SJ4 DSM 22704 | Firmicutes | Clostridia | Desaci_1621, Desaci_1622 |
| *Desulfosporosinus orientis* DSM 765 | Firmicutes | Clostridia | Desor_2652, Desor_2653 |
| *Desulfosporosinus* sp. OT | Firmicutes | Clostridia | DOT_5808, DOT_5807 |
| *Desulfosporosinus youngiae* DSM 17734 | Firmicutes | Clostridia | DesyoDRAFT_4238, DesyoDRAFT_4237 |
| *Ethanoligenens harbinense* YUAN-3 | Firmicutes | Clostridia | Ethha_0975, Ethha_0976 |

TABLE 1-continued

Microbial Strains with hgcA and hgcB Genes

| Strain | Phylum | Class | Locus tags (hgcA, hgcB) |
| --- | --- | --- | --- |
| *Syntrophobotulus glycolicus* FlGlyR DSM 8271 | Firmicutes | Clostridia | Sgly_2352, Sgly_2351 |
| *Dethiobacter alkaliphilus* AHT 1 | Firmicutes | Clostridia | DealDRAFT_3158, DealDRAFT_3157 |
| *Acetonema longum* APO-1 DSM 6540 | Firmicutes | Negativicutes | ALO_18015, ALO_18010 |
| *Methanofollis liminatans* GKZPZ DSM 4140 | Euryarchaeota | Methanomicrobia | Metli_1685, Metli_1684 |
| *Methanoregula boonei* 6A8 | Euryarchaeota | Methanomicrobia | Mboo_0422, Mboo_0421 |
| *Methanoregula formicicum* SMSP | Euryarchaeota | Methanomicrobia | Metfor_0951, Metfor_0952 |
| *Methanosphaerula palustris* E1-9c DSM 19958 | Euryarchaeota | Methanomicrobia | Mpal_1034, Mpal_1035 |
| *Methanospirillum hungatei* JF-1 DSM 864 | Euryarchaeota | Methanomicrobia | Mhun_0876, Mhun_0875 |
| *Methanolobus tindarius* DSM 2278 | Euryarchaeota | Methanomicrobia | MettiDRAFT_2866, MettiDRAFT_2865 |
| *Methanomethylovorans hollandica* DSM 15978 | Euryarchaeota | Methanomicrobia | Metho_0631, Metho_0630 |
| *Methanocella arvoryzae* MRE50 (RC-1) | Euryarchaeota | Methanomicrobia | RCIX2342, RCIX2341 |
| *Methanocella paludicola* SANAE | Euryarchaeota | Methanomicrobia | MCP_0718, MCP_0717 |

TABLE 2

Confirmed Hg Methylating Strains with Sequenced Genomes

| Organism name | Goldstamp ID[1] | Culture collections | Reference |
| --- | --- | --- | --- |
| *Desulfovibrio desulfurican.* ND132 | Gi03061 | — | Gilmour 2011 |
| *Desulfovibrio aespoeensis* | Gc01651 | DSM 10631 | Graham 2012 |
| *Desulfovibrio africanus* Walvis Bay | Gi03062 | ATCC 19997, NCIB 8397 | Brown 2011 |
| *Desulfobulbus propionicus* 1pr3 | Gc01599 | DSM 2032, ATCC 33891 | King 2000 |
| *Geobacter sulfurreducens* PCA | Gc00166 | DSM 12127, ATCC 51573 | Kerin 2006 |
| *Geobacter metallireducens* GS-15 | Gc00314 | DSM 7210, ATCC 53774 | Kerin 2006 |

[1]Goldstamp ID: Genomes OnLine Database - GOLD (Pagani 2012).

TABLE 3

Confirmed Non-methylating Strains with Sequenced Genomes

| Organism name | Goldstamp ID[1] | Culture collections | Reference |
| --- | --- | --- | --- |
| *Desulfovibrio desulfuricans* MB | Gc00931 | DSM 6949, ATCC 27774 | Ranchou-Peyruse 2009; Gilmour 2011 |
| *Desulfovibrio vulgaris* Hildenborough | Gc00184 | DSM 644, ATCC 29579 | Ranchou-Peyruse 2009; Gilmour 2011 |
| *Desulfovibrio alaskensis* G20 | Gc00315 | DSM 16109 | Gilmour 2011 |
| *Desulfovibrio salexigens* | Gc01109 | DSM 2638, ATCC 14822 | Gilmour 2011 |
| *Desulfotomaculum acetoxidans* | Gc01106 | DSM 771, ATCC 49208 | Bridou 2010 |
| *Desulfotomaculum nigrificans* | Gi03933 | DSM 574, ATCC 19998 | Bridou 2010 |
| *Syntrophobacter fumaroxidans* MPOB | Gc00453 | DSM 10017 | Ranchou-Peyruse 2009 |
| *Desulfovibrio piger* | Gi01734 | ATCC 29098, DSM 749 | Graham 2012 |

[1]Genomes OnLine Database - GOLD (Pagani 2012)

EXAMPLE 2

Structural Analysis of HgcA and HgcB Genes

Figure 3:
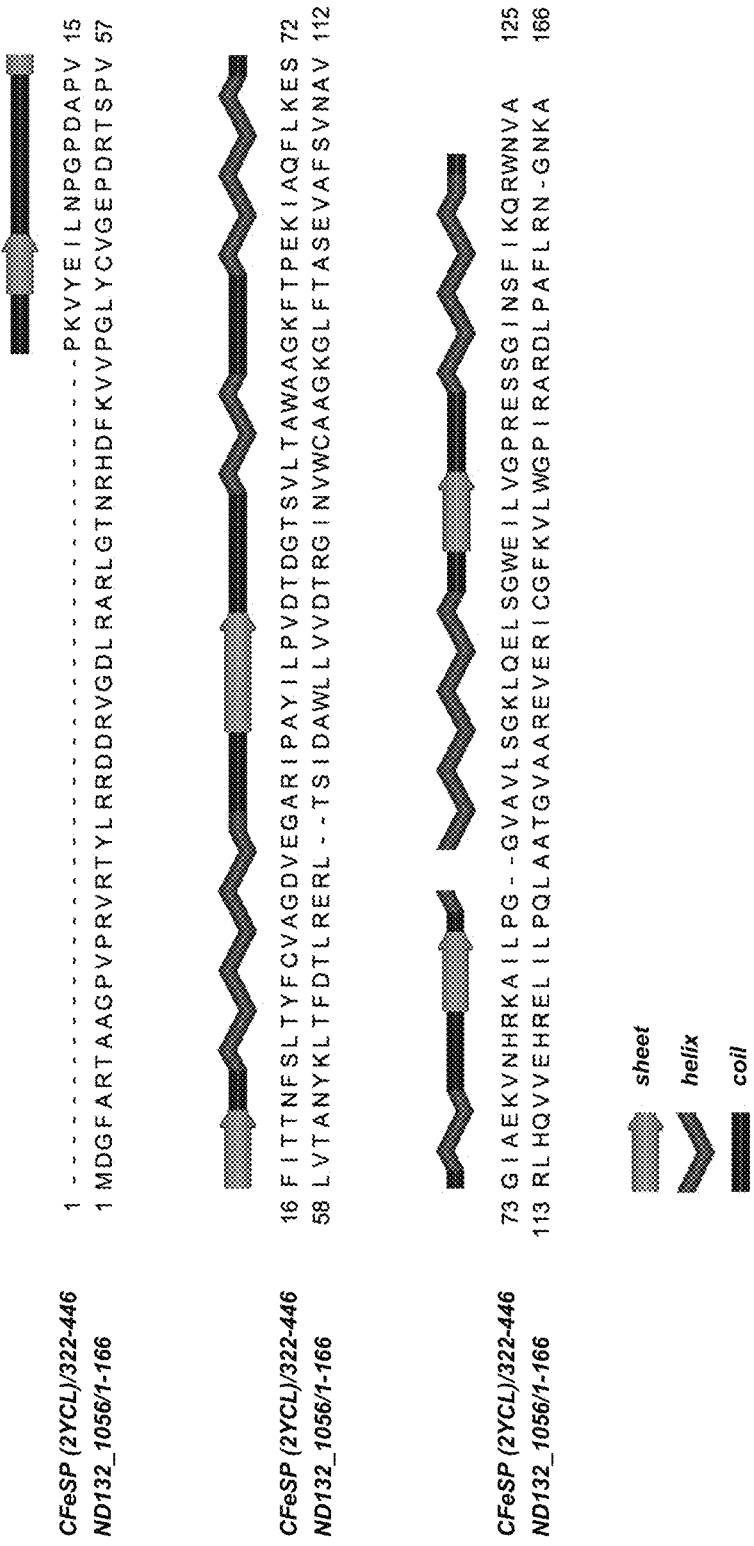
FIG. 3 provides a structure-based amino acid sequence alignment for the cobalamin-binding domain of the corrinoid iron-sulfur protein (CFeSP) from *Carboxydothermus hydrogenoformans* (SEQ ID NO. 1) with HgcA from *D. desulfuricans* ND132 (SEQ. ID NO. 205). Only the regions producing significant sequence similarity are shown. The secondary structure diagram was derived from the crystal structure of the CfsA subunit of CFeSP (PDB: 2YCL).
Figure 7:
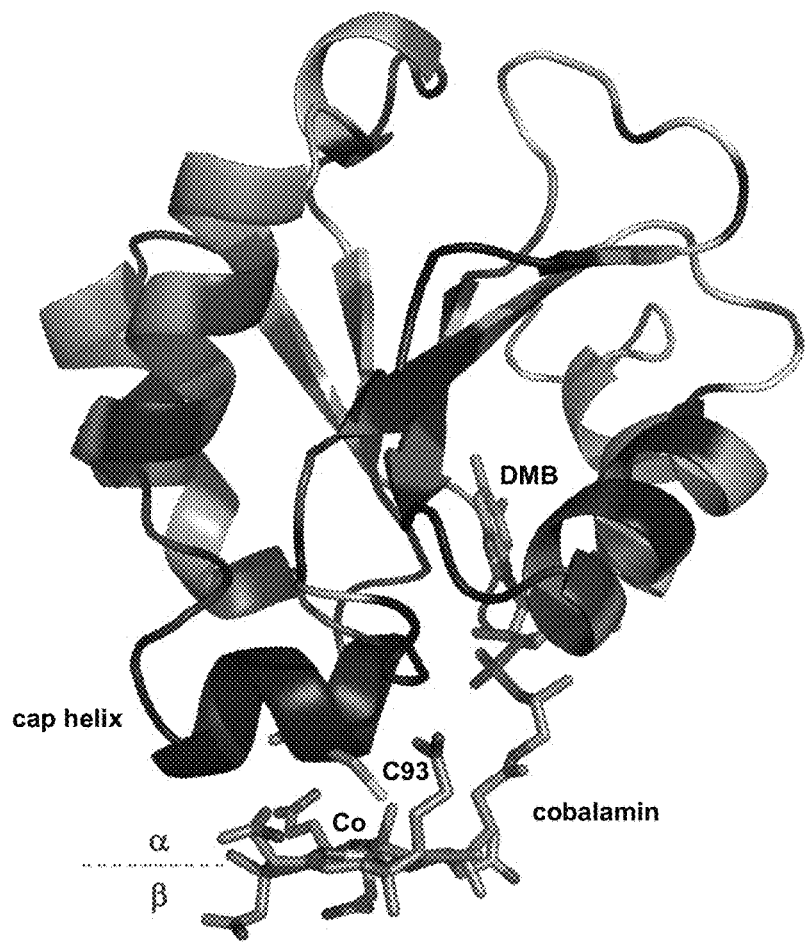
FIG. 7 shows a homology model for residues 43-166 of the cobalamin-binding domain of HgcA from *D. desulfuricans* ND132 constructed with the structure of CFeSP from *C. hydrogenoformans* as a template. Color shading indicates the degree of conservation among orthologous HgcA proteins (white/grey: low; blue/dark: high). The proximity of Cys93 to the Co center of the cobalamin cofactor suggests "Cys-on" coordination of Co in HgcA.
Figure 8A:
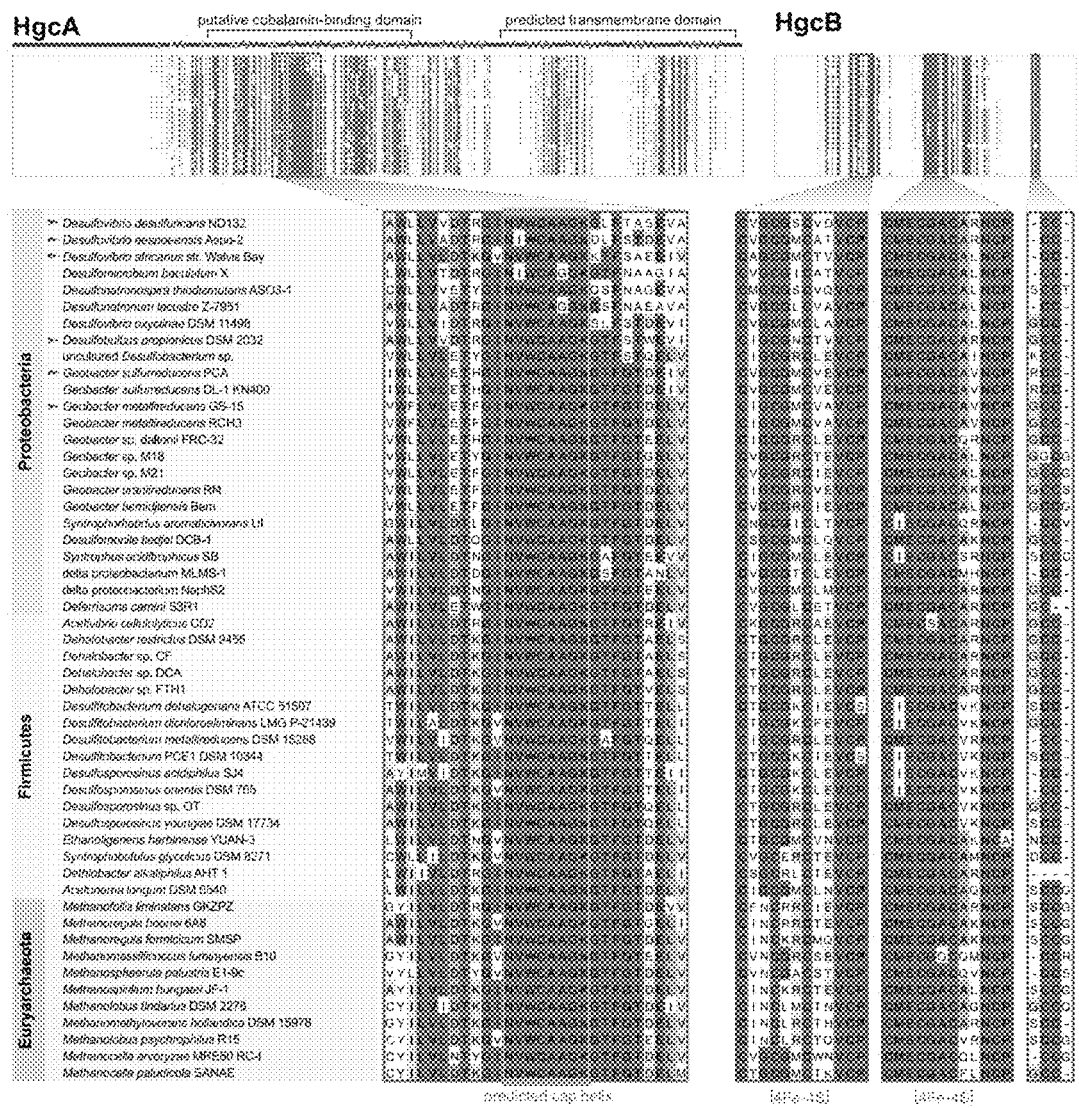
FIG. 8A, top, shows a sequence conservation heat map for the sequence alignments for HgcA and its orthologs in the 46 bacterial and archaeal strains listed in Table 1. The bottom panel provides the sequences for the highly conserved region from the cobalamin-binding domain, including the putative cap helix (SEQ ID NOS. 65-110, respectively, in order of appearance). The inner consensus sequence is N[V/I]WCA[A/G]GK (SEQ ID NO. 6). Residues in brackets are alternatives for the given amino acid position.
Figure 8B:
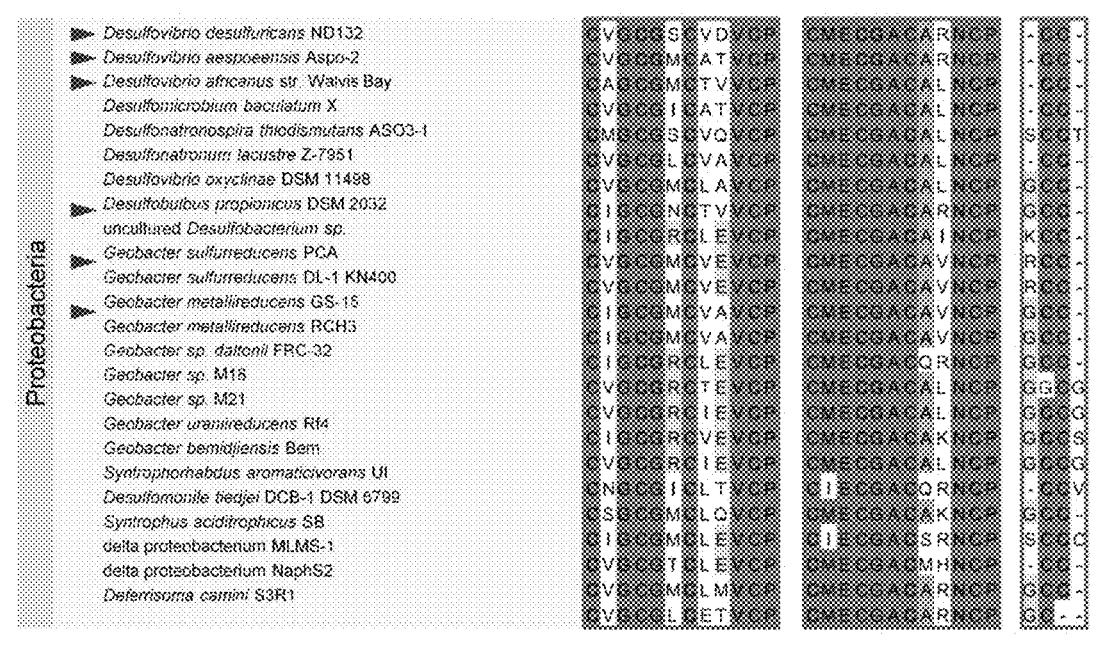
Figure 8C:
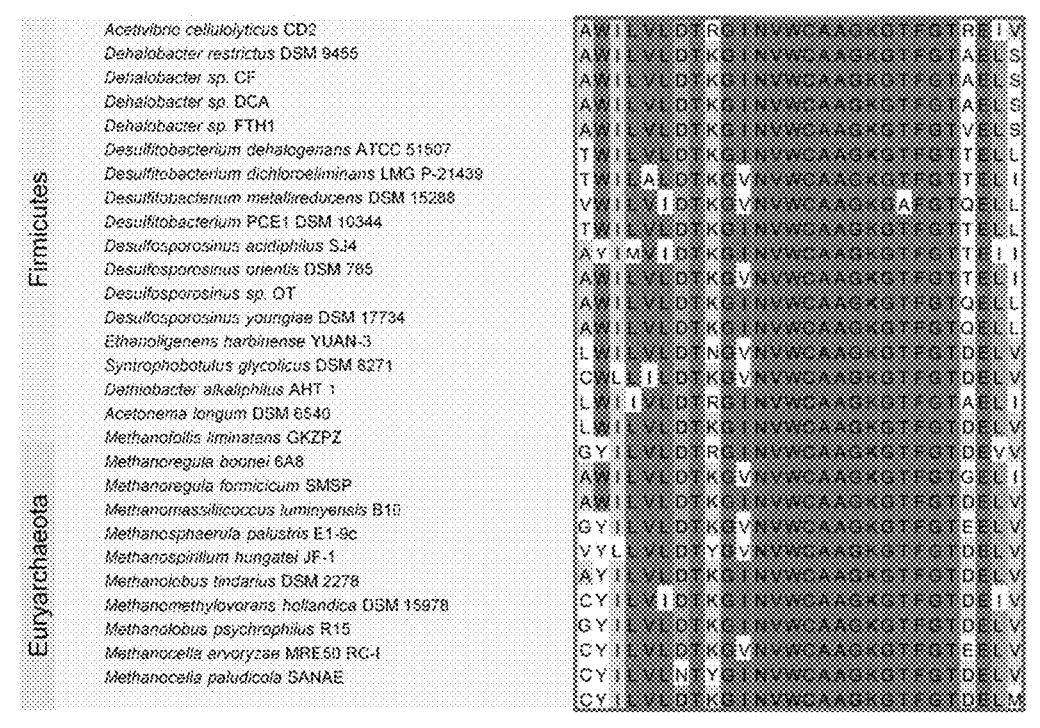

The N-terminal domain of HgcA is similar to the cobalamin-binding domain of CFeSP (PDB 2YCL; FIG. 3). Protein sequence alignment and modeling of the three-dimensional structure of the putative cobalamin-binding domain of HgcA indicated that it likely binds a corrinoid cofactor in a "5,6-dimethylbenzimidazole-off (DMB-off), histidine-off (His-off)" configuration (Ragsdale 2008a) similar to CFeSP (FIG. 7). Furthermore, alignment of the cobalamin-binding domain sequences shows a highly conserved motif, with a consensus sequence of N[V,I]WCA[A,G]GK (SEQ ID NO. 6), within the region of highest similarity to the CfsA subunit of CFeSP (FIG. 8) which is embraced within a slightly longer consensus sequence of TxG[I,V]N [V,I]WCA[A,G]GK[G,D,K,Q][T,L,S,A]F (SEQ ID NO. 204) as described in Example 1.

The lower-axial cobalt ligand in corrinoid proteins plays a role in the chemistry of Co—C bond cleavage (Banerjee, 2003). The HgcA region of highest sequence similarity to CFeSP corresponds to the cap helix, which is located near the lower-axial face of the corrin ring (Svetlitchnaia 2006). In CFeSP, the side chain of Thr374 is located within ~3 Å of the cobalt. However, in all orthologs, a strictly conserved Cys residue (Cys93 in *D. desulfuricans* ND132) occupies the position corresponding to that of Thr374 in CFeSP. Although Thr374 is not considered a ligand for cobalt (Ragsdale 1987, Svetlitchnaia 2006), a Cys thiolate could be expected to coordinate strongly to Co(III) (Polson, 1997). By analogy, it appears that a lower-axial coordination of $CH_3$-cob(III)alamin by Cys, i.e., a "Cys-on" coordination, stabilizing the Co(III) state and enable transfer of a methyl group to Hg(II) substrates.

Figure 9A:
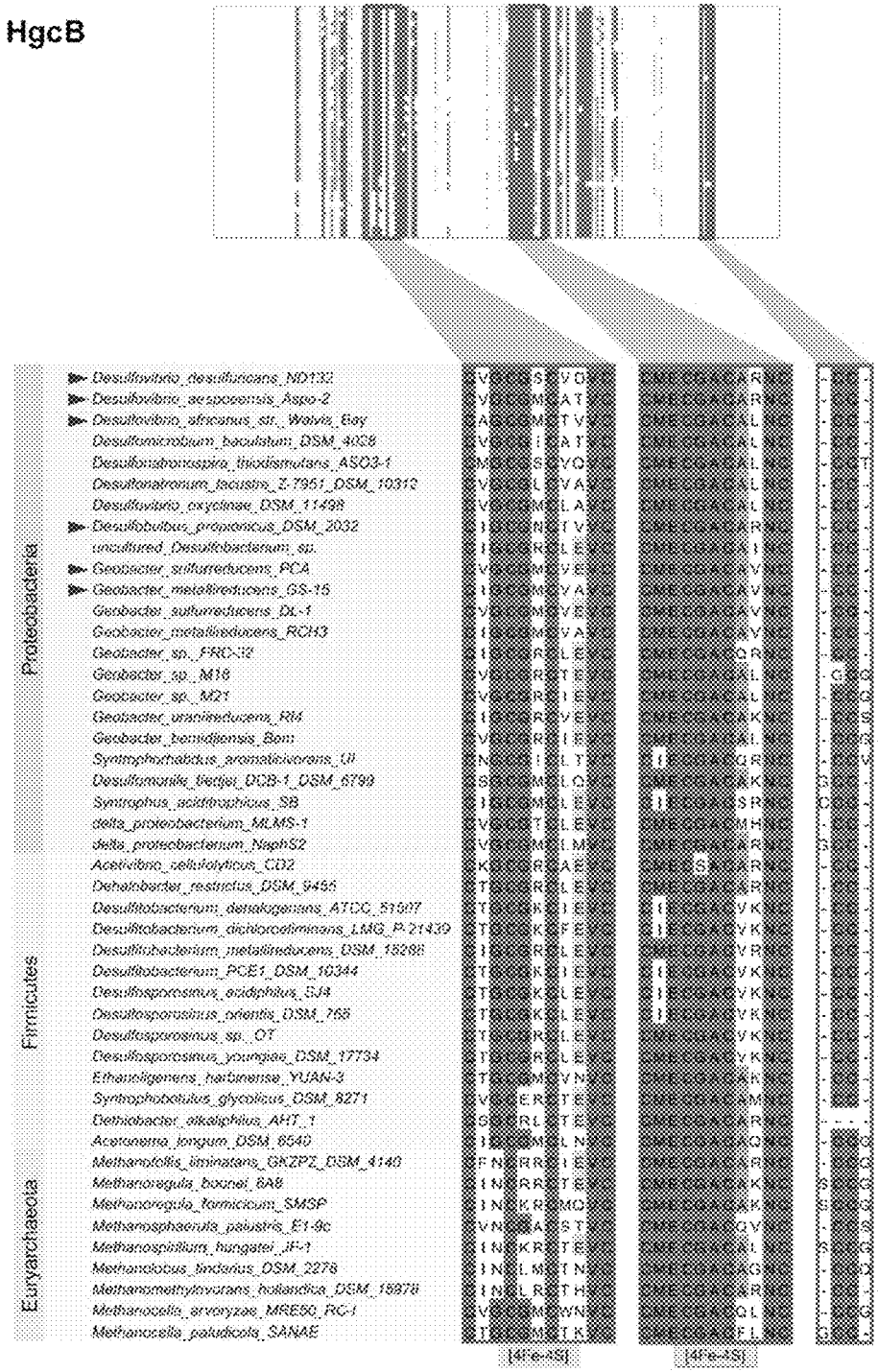
FIG. 9A, top shows a sequence conservation heat map for the sequence alignments for HgcB and its orthologs in the 46 bacterial and archaeal strains listed in Table 1. The bottom panel provides the sequences for the three highly conserved regions: the two $CX_2CX_2CX_3C$ (SEQ ID NO. 7) motifs characteristic of [4Fe-4S] clusters and the highly conserved vicinal pair of cysteines at the C-terminus.
Figure 9B:
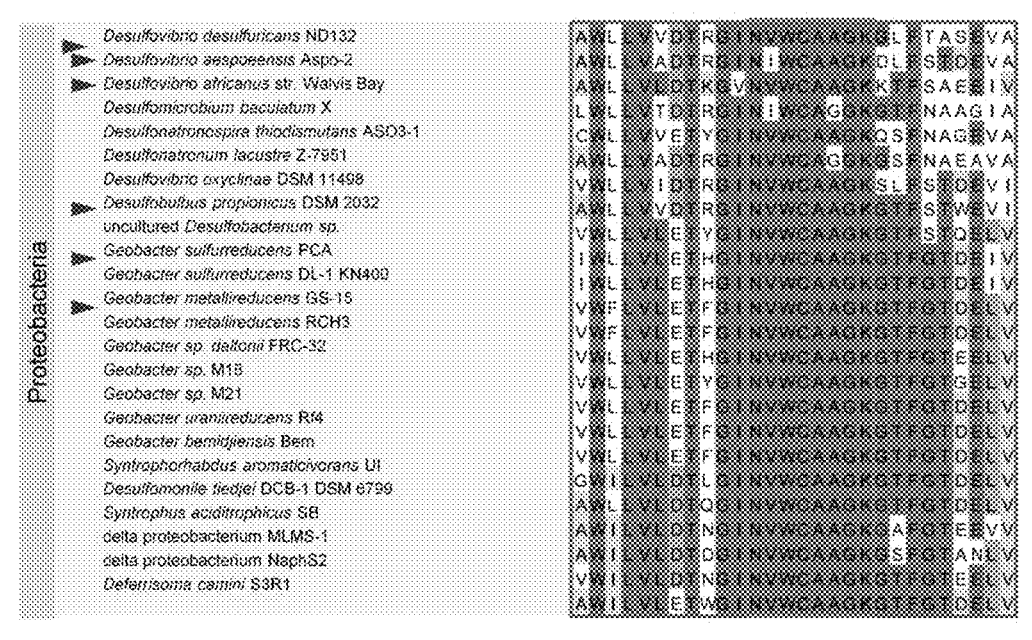
Figure 9C:
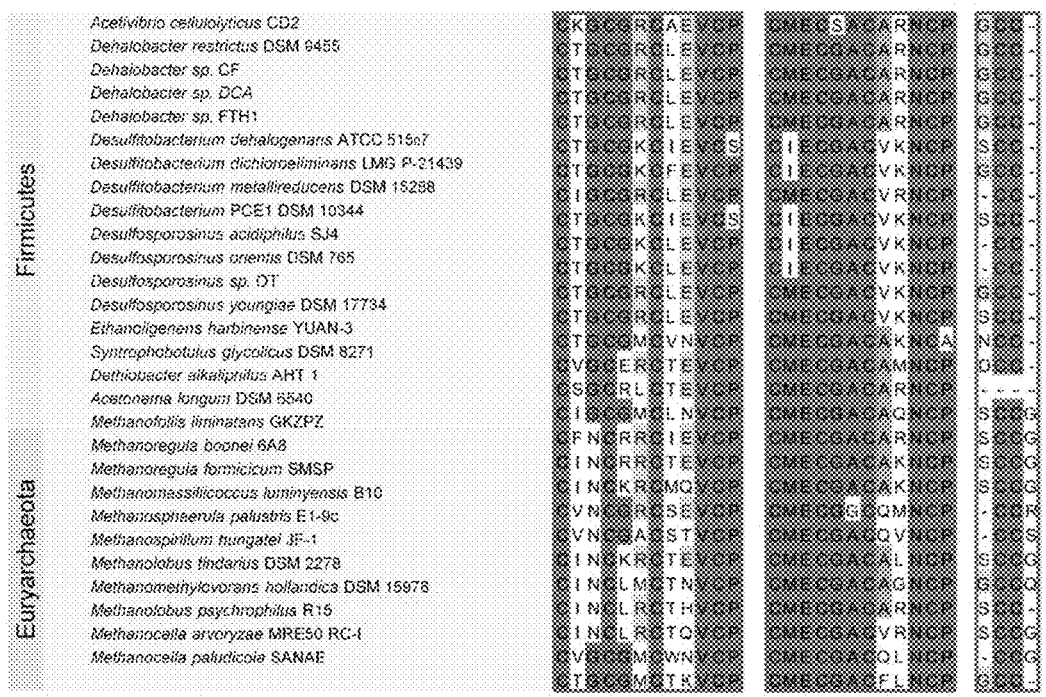
FIG. 9C is an expanded view of the Firmicutes and Euryarcheota shown in the bottom panel of FIG. 9A.

Identification of HgcA as a potential methyl donor to Hg(II) suggested a function for HgcB. Initial transfer of a methyl group to HgcA presumably originates from 5-methyltetrahydrofolate ($CH_3$-THF) (Choi, 1994b) as a $CH_3^+$ group, catalyzed by a methyltransferase such as the $CH_3$-THF:CFeSP methyltransferase (MeTr) (Ragsdale 2008b) or an MeTr-like enzyme. Subsequent transfer of the methyl group to a Hg(II) substrate would require a source of electrons to enable turnover. Protein sequence analysis of the ferredoxin-like HgcB and its orthologs revealed two strictly conserved [4Fe-4S] binding motifs with the sequence $CX_2CX_2CX_3C$ (SEQ ID NO. 7)(FIG. 9). Presence of this motif is consistent with this protein acting as the electron source. Thus, the chemistry required for Hg(II) methylation by a corrinoid protein, the presence of two [4Fe-4S] binding motifs in HgcB, and the genetic context of HgcA and HgcB and (and all pairs of respective orthologs in other known methylators), are consistent with HgcB carrying out the reduction of the corrinoid cofactor to poise HgcA to accept a $CH_3^+$ group.

EXAMPLE 3

Functional Analysis of the hgcA and hgcB Genes and Gene Products

Figure 10:
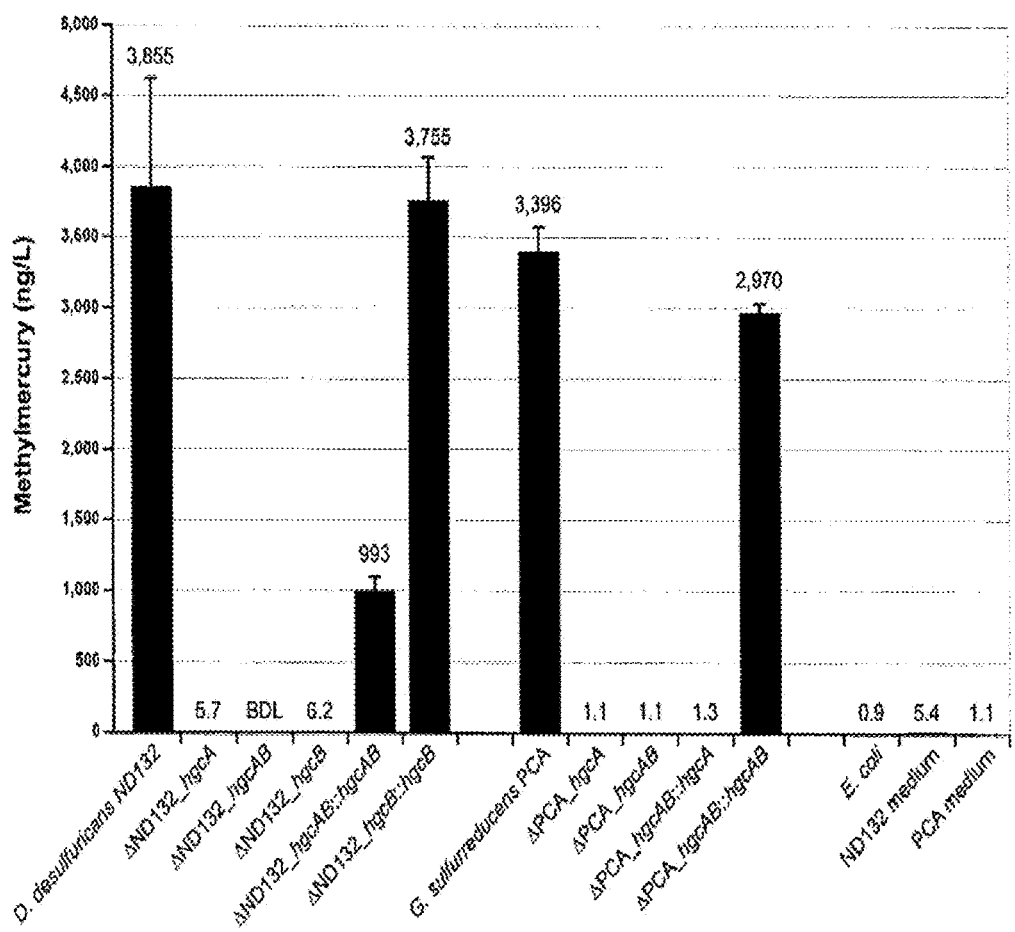
FIG. 10 provides a bar graph illustrating production of methylmercury in various *D. desulfuricans* ND132 (ND132) and *G. sulfurreducens* PCA (GSU) wild-type strains, deletion strains, complementation strains and controls. It should be noted that $\Delta hgcAB_{PCA}$ complemented with $hgcA^{+}_{PCA}$ is still deleted for $hgcB_{PCA}$. Bars show methylmercury concentrations (ng/L) after overnight incubation as determined by inductively-coupled plasma mass spectrometry (ICP-MS). The "$\Delta$" prefix indicates a gene deletion and "::" indicates complementation. Values are presented as the average of triplicate assays with standard deviation. BDL is "Below Detection Limit."

Deletion and Complementation Studies:

Overall Results: To establish the role of HgcA and HgcB in mercury methylation, these genes were deleted, either individually or as a pair from *D. desulfuricans* ND132. Additionally, the pair or hgcA alone was deleted from *G. sulfurreducens* PCA. Methylation activity was verified by two independent methylation assays. In each case, deletion of one or both genes resulted in abolition of mercury methylation activity by greater than 99% relative to the wild-type level. Complementation of the two-gene cluster restored 26% and 87% of wild-type activity in *D. desulfuricans* ND132 and *G. sulfurreducens* PCA, respectively, when measured by ICP-MS (FIG. 10). Deletion and subsequent complementation of hgcB alone in *D. desulfuricans* ND132 yielded <1% and 102% of wild-type methylation activity, respectively. Independent assays of the same strains by atomic fluorescence spectroscopy showed that complementation of the two-gene deletion in *D. desulfuricans* ND132 and *G. sulfurreducens* PCA restored 90% and 79% of wild-type activity; whereas, complementation of *D. desulfuricans* ND132 ΔhgcB yielded 84% of wild-type activity. Reasons for the discrepancies between the two assay methods for *D. desulfuricans* ND132 constructs are unclear. Complementation of either gene alone into the double deletion mutant did not restore detectable methylmercury activity. Restoration of *D. desulfuricans* ND132 ΔhgcA alone was not performed. Comparative growth curves with the deletion mutants showed no impairment in rate or extent of growth. Thus, under the conditions tested the construction of the deletions did not cause major growth aberrations that might interfere with the detection of methylation activity.

General: All chemicals were of analytical grade and were commercially available from Fisher Scientific (Pittsburgh, Pa.) or Sigma-Aldrich (St. Louis, Mo.). Biological reagents were from the same sources unless indicated otherwise. The bacterial strains, plasmids and primers are listed Tables 4, 5 and 6, respectively.

Culture Conditions: *D. desulfuricans* and *G. sulfurreducens* strains were cultured at 34° C. under anaerobic conditions in an anaerobic chamber (85:10:5, $N_2$:$CO_2$:$H_2$; Coy Laboratory Products, Inc., Grass Lake, Mich.) in MOY medium unless otherwise indicated. The MOY basal medium contained the following per liter: $MgCl_2.6H_2O$ (1M), 8.0 ml; $NH_4Cl$ (4M), 5 ml; $CaCl_2$ (1M), 0.6 ml; $K_2HPO_4$—$NaH_2PO_4$ (1M), 2.0 ml; Trace elements (Postgate, 1984), 6 ml; $FeCl_2$ (0.125M)/EDTA (250 mM), 50 μl; Tris-HCl (2M) pH 7.4, 15 ml; Thauer's Vitamins 10× (Brandis 1981), 1.0 ml. The yeast extract content was increased to 2.0 g per liter. In addition, titanium citrate or thioglycolate (0.38 mM or 1.2 mM final concentration, respectively) was added after sterilization to poise the redox potential of the media. The pH values of the final media were adjusted to 7.2.

*D. desulfuricans* ND132 was grown in MOYLS4 medium containing 30 mM sulfate and 60 mM lactate (Zane 2011) for genetic experiments. MOYLS4 medium also contained yeast extract up to 0.2% (w/v) and additionally was poised with sodium thioglycolate (1.2 mM) post-sterilization. *D. desulfuricans* ND132 was sensitive to kanamycin and spectinomycin at 400 μg·ml$^{-1}$ and 200 μg·ml$^{-1}$, respectively.

*G. sulfurreducens* PCA was grown in NBFA medium with 40 mM fumarate and 15 mM acetate (Galushko 2000; Coppi 2001).

To screen for loss of Hg-methylation, cells were grown in MOYPF medium (Gilmour 2011) containing 40 mM fumarate, 40 mM pyruvate and 1 mM cysteine (as the sole sulfur source) to limit sulfide-Hg(II) complexes (Bridou 2011).

Bacterial Plating and Growth: For plating, the top agar technique was used. Plates contained 1.5% (w/v) agar and, after pouring, were degased overnight in a hood and stored in an anaerobic jar (Mitsubishi AnaeroPack®, Thermo Scientific, USA) until use. The anaerobic top agar solution contained 0.75% (w/v) agar) and was maintained molten at 55° C. until pouring. Antibiotic used for selection/screening and reductant solutions were added to the molten agar prior to pouring plates.

Bacterial growth was monitored by measuring the optical density at 600 nm ($OD_{600}$) with a Genesys 20 spectrophotometer (Thermo Fisher, USA) or protein concentration by the Bradford method using bovine serum albumin (Sigma, St. Louis, Mo.) as standard (Bradford 1976). Spectinomycin resistant mutant *D. desulfuricans* ND132 (this study) containing pMO9075 (Keller 2011), was used as a positive growth control during plate selection and screening.

Molecular Biological Techniques: Molecular cloning in *E. coli* was conducted as described (Zane 2011) with growth aerobically in in LC medium or SOC medium, and when used, with kanamycin added at 100 μg/ml and spectinomycin at 100 μg/ml. Plasmid DNA from *E. coli* was prepared using a GeneJET Plasmid Miniprep Kit (Fermentas, Thermo Scientific, Glen Burnie, Md.).

PCR Techniques: PCR was performed with Herculase II polymerase (Stratagene, La Jolla, Calif.) and the primers listed in Table 6 (IDT, Coralville, Iowa). PCR products (50 μL) were treated with 20 U of DpnI and incubated at 37° C. for 1 hour. Amplified DpnI-treated DNA fragments were purified using a Wizard® SV Gel and PCR Clean-up System (Promega, USA). Agarose gel electrophoresis was conducted as described (Zane 2011).

Sequencing: Nucleotide sequences were determined using Big Dye Terminator cycle sequencing chemistry (Applied Biosystems) with a 3730×l 96-capillary DNA Analyzer. After PCR amplification, the sequences of the amplified fragment were verified against reference sequences for *D. desulfuricans* ND132 (GenBank accession no. NC_016803.1) and *G. sulfurreducens* PCA (GenBank accession no. AE017180.1).

Desulfovibrio and Geobacter Cloning and Transformation: Chromosomal DNA was purified from cultured *Desulfovibrio* and *Geobacter* strains as described (Zane 2011) except that DNA was purified with Wizard® Genomic DNA Purification Kit (Promega, USA) and eluted in sterile 18 $\Omega M \cdot cm^{-1}$ water (Quantum® EX, Millipore, Mass., USA).

Desulfovibrio and Geobacter strains were transformed as described for *D. vulgaris* Hildenborough (Keller 2011) by electroporation under anaerobic conditions with 100 μl of prepared cells and 500 μg of plasmid at 1500 V, 250Ω and 25 mF. Typical voltage and time constants of 1420 V and >1 ms were obtained for each electroporation. To increase cell recovery following electroporation, the transformed cells were resuspended in 1 ml of anaerobic MOYLS4 medium, transferred to Eppendorf tubes and incubated for 48 hours inside an anaerobic chamber with frequent inversion of the culture to re-suspend cells.

Various aliquots of the recovered cells were plated in MOYLS4 medium with kanamycin to generate $\Delta hgcA_{ND132}$, $\Delta hgcB_{ND132}$ or $\Delta hgcAB_{ND132}$ mutants. The plates were incubated for 4 to 7 days at 34° C. for $\Delta hgcA_{ND132}$, $\Delta hgcB_{ND132}$ or $\Delta hgcAB_{ND132}$ mutants, or 20 days for $\Delta hgcA_{PCA}$ and $\Delta hgcAB_{PCA}$ deletions.

Generation of Deletion Constructs: The plasmids used for the deletion of hgcA alone, hgcB alone, and the hgcA/hgcB gene cluster in *D. desulfuricans* ND132 and *G. sulfurreducens* PCA strains were constructed by SLIC sub-cloning with T4 DNA polymerase treated inserts (Li 2007) or by Gibson Assembly (Mew England BioLabs, Beverly, Mass.; Gibson 2009). Deletion of individual genes and the two-gene cluster was accomplished by amplification and assembly of four independent regions.

First, the spectinomycin resistance determinant and the pUC ori of pMO719 (Zane 2011; Keller 2011) were amplified. Second, the kanamycin resistance cassette (with its promoter) from pMO746 was generated. Note that the upp gene was also conserved in the latter cassette but was not used in these studies. Finally, the third and fourth regions were the DNA regions upstream and downstream of the targeted gene (see Tables 5 and 6).

Generation of Complementation Plasmids: Complementation of $\Delta(hgcB_{ND132})$ and $\Delta(hgcAB_{ND132})$ *D. desulfuricans* ND132 mutants and the $\Delta(hgcAB_{PCA})$ mutant of *G. sulfurreducens* was achieved, respectively, by chromosomal "knock-in" of $hgcB_{ND132}$ or $hgcAB_{ND132}$ and $hgcA_{PCA}$ or $hgcAB_{PCA}$ along with a spectinomycin resistance marker that replaced the kanamycin resistance marker in the deletion mutants (Table 6). In all cases, a ~1680 bp fragment containing the origin of replication and a partial bla gene ($Ap^R$) was amplified from pCR4/TOPO (pMO4659 and pMO4661) or pUC19 (pORNL1000 and pORNL1001) to serve as a backbone for maintenance and selection in *E. coli* (Table 6).

To complete the preparation of *D. desulfuricans* ND132 complementation constructs pMO4659 and pMO4661, a 1339 bp fragment comprised of 20 bp upstream of $hgcA_{ND132}$ and the two genes ($hgcA_{ND132}$ and $hgcB_{ND132}$), and a 2050 bp fragment containing a 731 bp upstream DNA along with both $hgcAB_{ND132}$ was amplified from *D. desulfuricans* ND132, respectively. In all cases, a 789 bp region downstream from $hgcB_{ND132}$ was amplified to flank the downstream spectinomycin resistance cassette from pMO719. The four amplicons were assembled according to the SLIC procedure (Li 2007).

In the case of *G. sulfurreducens* PCA, a 2103 bp fragment containing the upstream DNA along with both $hgcA_{PCA}$ and $hgcB_{PCA}$, or a 1797 bp fragment comprised of 762 bp upstream of the two genes along with $hgcA_{PCA}$ was amplified from *G. sulfurreducens* PCA to support preparation of complementation constructs pORNL1000 and pORNL1001 respectively. The four amplicons were assembled with a Gibson Assembly Master Mix (Gibson 2009). The resulting plasmids were transformed into chemically competent *E. coli* DH5-α cells (BioLine), screened with PCR, sequenced, and used for transformation of the deleted mutants.

Southern Blot Analysis: Gene deletions were verified and confirmed by Southern blots (FIG. 11) as previously described (Bender 2007), using the PCR amplicon primers for the upstream region used for the deletion of the hgcA gene.

Mercury Methylation Assay: A. Measurement of Methylmercury by Ethylation Purge and Trap Gas Chromatography Atomic Fluorescence Spectroscopy (EPT-GC-AFS.)

The deletion or complementation transformants were sub-cultured in MOYPF medium (1% v/v) and grown to an $OD_{600}$ of ~0.5. These cultures were diluted to a cell density of $OD_{600}$ ~0.150 in fresh MOYPF. A 400 μL aliquot was removed into a 2 mL microcentrifuge tube, $HgCl_2$ was added (final concentration 10 ng/mL) and the sample was incubated in the dark for 2 hours at 34° C. After incubation, the sample was immediately acidified to a final concentration of 3N $HNO_3$ as described (Bridou 2011). The samples were left at room temperature for 24 hours to allow acid digestion of the cellular components followed by EPT-GC-AFS analysis as described in the following paragraph. Wild-type *D. desulfuricans* ND132 or *G. sulfurreducens* PCA was used as a positive, Hg-methylating control. Negative, Hg-non-methylating controls were heat-killed *D. desulfuricans* ND132, viable *Desulfovibrio alaskensis* G20, heat-killed *D. alaskensis* G20 and MOYPF as an abiotic control. Mutants were also tested as heat-killed cultures. None of the non-methylating controls methylated Hg(II) above the detection limits.

Methylmercury production was determined by EPT-GC-AFS according to EPA method 1630 (USEPA 2001). For the analysis, an 80 μl aliquot of the acidified sample was added to 40 ml Na-acetate buffer (pH 3.9). The Hg species were then ethylated with $NaBEt_4$ and extracted from the solution into an automated purge and trap system (MERX, Brooks Rand LLC, Seattle, Wash.) followed by gas chromatography separation and quantification by AFS with a MERX Hg speciation GC and Pyrolysis Module coupled to a Model III Cold Vapor Atomic Fluorescence Spectrophotometer (MERX, Brooks Rand LLC, Seattle, Wash.). Mercury chloride ($HgCl_2$) and methylmercury chloride ($CH_3HgCl$) used for Hg-methylation assays and external calibration, respectively, were purchased from MERX and greater than 95% pure. The analytical detection limits determined over the analysis were ≤0.52±0.1 pg/mL. Details of the analytical treatment and calculations used to determine methylmercury concentrations are provided in EPA method 1630 (USEPA 2001).

Mercury Methylation Assay: B. Measurement of Methylmercury Generation Using Stable Isotopes and ICP-MS Mercury methylation production was also determined with enriched stable isotopes (Hintelmann 1997; Heyes 2006). At the mid-log phase of growth 10 ng/ml inorganic $^{201}Hg^{2+}$ was added to 10 ml aliquots of cell culture in $N_2$-purged, anaerobic, sterile Balch tubes and incubated overnight. The conversion of $^{201}Hg^{2+}$ to $CH_3$-$^{201}Hg$ (1 h) was used to quantify the amount of $Hg^{2+}$ methylated. Cultures were then preserved by adding 500 μL of 9 M $H_2SO_4$ and stored at 4° C. until analysis. Sample pH was verified to be <2.0 to ensure that culture buffering capacities were overcome. For total Hg quantification, samples were diluted and acidified (2% HCl with 7.5% bromine monochloride) to digest organic and cellular material.

Total Hg and $CH_3Hg$ were measured using an automated purge and trap system (MERX, Brooks Rand LLC, Seattle, Wash.) followed by detection on an inductively-coupled plasma mass spectrometer (ICP-MS, Elan-DRCe, PerkinElmer Inc., Shelton, Conn.) using adapted EPA Methods 1630 and 1631 (USEPA 2001; USEPA 2002). Modifications to the EPA methods included the use of isotope dilution with enriched stable isotopes to determine the total Hg and $CH_3Hg$ concentrations and detection of the Hg using ICP-MS to separate the various Hg isotopes (Hintelmann2002). For total Hg analyses, the enriched isotope ($^{200}Hg$) was added just prior to the reduction of the Hg with stannous chloride. Enriched $CH_3$-$^{200}Hg$, synthesized from $Hg^{2+}$ using methylcobalamin (Hintelmann 2002), was added to the sample prior to distillation as an internal standard. Enriched Hg isotopes (purchased from Oak Ridge National Laboratory), were all greater than 95% pure and the small abundance of other isotopes was taken into account during data processing (Sturup 2005).

TABLE 4

Bacterial Strains

| Strain | Genotype | Source or Reference |
|---|---|---|
| *Escherichia coli* | | |
| α-Select (Bronze efficiency) | F-deoR endA1 recA1 relA1 gyrA96 hsdR17($r_k^-$, $m_k^+$) supE44 thi-1 phoA Δ(lacZYA-argF)U169 Φ80lacZΔM15 λ- | Bioline |
| α-Select (Silver efficiency) | F− deoR endA1 recA1 relA1 gyrA96 hsdR17($r_k^-$, $m_k^+$) supE44 thi-1 phoA Δ(lacZYA-argF)U169 Φ80lacZΔM15 λ− | Bioline |
| *Desulfovibrio desulfuricans* | | |
| ND132 | Wild type | Gilmour 2011 |
| JWN1000 | ND132, ΔhgcA1::(npt $upp^4$); $Km^r$ | This study |
| JWN1001 | ND132, Δ(hgcAB)1::(npt upp); $Km^r$ | This study |
| JWN1002 | ND132, ΔhgcB1::(npt upp); $Km^r$ | This study |
| JWN1003 | JWN1001 $hgcAB^+$ $aadA^B$; $Km^s$, $Sp^r$ | This study |
| JWN1004 | JWN1002 $hgcB^+$ aadA; $Km^s$, $Sp^r$ | This study |
| JWN1010 | ND132 hgcA2(C93T)$hgcB^+$ aadA; $Sp^r$ | This study |
| *Geobacte. sulfurreducens* | | |
| PCA | ATCC 51573 | ATCC |
| DEGS 1000 | PCA ΔhgcA1::(npt upp); $Km^r$ | This study |
| DEGS 1001 | PCA Δ(hgcAB)1::(npt upp); $Km^r$ | This study |
| DEGS 1002 | DEGS1001 $hgcA^+$ ΔhgcB aadA; $Sp^r$ | This study |
| DEGS 1003 | DEGS1001$(hgcAB)^+$ aadA; $Sp^r$ | This study |
| DEGS 1004 | DEGS1001 $hgcB^+$ aadA; $Sp^r$ | This study |

TABLE 5

Plasmids

| Plasmid | Characteristics | Source or Reference |
|---|---|---|
| pCR ® 4-TOPO | TOPO cloning vector; $AP^r$, $Km^r$ | Invitrogen |
| pUC19 | Cloning vector, $AP^{r, pMB1ori}$ | Invitrogen/ GenBank L09137 |
| pCR8/GW/TOPO | TOPO cloning vector; $Sp^r$ | Invitrogen |
| pMO9071 | pCR8/GW/TOPO containing SRB replicon (pBG1) with npt; $Km^r$, $Sp^r$ | Zane 2011 |
| pMO746 | upp in an artificial operon with npt from pMO9071 and $Ap^r$-pUC ori from pCR4/TOPO, $P_{npt}$-npt-upp;, $Km^r$ | This study |

TABLE 5-continued

Plasmids

| Plasmid | Characteristics | Source or Reference |
|---|---|---|
| pMO719 | pCR8/GW/TOPO containing SRB replicon (pBG1); $Sp^r$ | Keller 2009 |
| pMO9075 | pMO719 containing $P_{npt}$ for gene expression from the plasmid in *Desulfovibrio* strains, $Sp^r$ | Keller 2011 |
| pMO4650 | $Sp^r$ and pUC ori from pMO719 plus upstream and downstream DNA regions from $hgcA_{ND132}$ flanking the artificial operon of $P_{npt}$-npt-upp from pMO746; for marker exchange deletion mutagenesis; $Sp^r$ and $Km^r$ | This study |
| pMO4651 | $Sp^r$ and pUC ori from pMO719 plus upstream DNA region from $hgcA_{ND132}$, the artifical operon of $P_{npt}$-npt-upp from pMO746 and a region from downstream $hgcB_{ND132}$; for marker exchange deletion mutagenesis; $Sp^r$ and $Km^r$ | This study |
| pMO4652 | $Sp^r$ and pUC ori from pMO719 plus upstream and downstream DNA regions from $hgcB_{ND132}$ flanking the artificial operon of $P_{npt}$-npt-upp from pMO746; for marker exchange deletion mutagenesis; $Sp^r$ and $Km^r$ | This study |
| pMO4600 | pMO9075 containing $P_{npt}$-$hgcA_{ND132}$, $Sp^r$ | This study |
| pMO4601 | pMO9075 containing $P_{npt}$-$hgcB_{ND132}$, $Sp^r$ | This study |
| pMO4602 | pMO9075 containing $P_{npt}$-$hgcAB_{ND132}$, $Sp^r$ | This study |
| pMO4659 | $Ap^r$-pUC ori from pCR4/TOPO with $hgcA_{ND132}$ and $hgcB_{ND132}$ including a 20 bp region upstream from $hgcA_{ND132}$, and a 789 bp region downstream from $hgcB_{ND132}$ flanking the $Sp^r$ cassette from pMO719; $Sp^r$, $Ap^r$ | This study |
| pMO4661 | $Ap^r$-pUC ori from pCR4/TOPO with $hgcA_{ND132}$ and $hgcB_{ND132}$ including a 731 bp region upstream from $hgcA_{ND132}$, and a 789 bp region downstream from $hgcB_{ND132}$ flanking the $Sp^r$ cassette from pMO719; $Sp^r$, $Ap^r$ | This study |
| pORNL1000 | Partial bla and pMB1 ori from pUC19 with $hgcA_{PCA}$ including a 762 bp upstream region, and a 995 bp region downstream from $hgcB_{PCA}$ flanking the $Sp^r$ cassette from pMO719; $Sp^r$, $Ap^r$ | This study |
| pORNL1001 | $Sp^r$ and pUC ori from pMO719 plus upstream DNA region from with $hgcA_{PCA}$, the artificial operon of $P_{npt}$-npt-upp from pMO746 and a region from downstream $hgcB_{PCA}$; for marker exchange deletion mutagenesis; $Sp^r$, $Km^r$ | This study |
| pORNL1002 | $Sp^r$ and pUC ori from pMO719 plus upstream DNA region from $hgcA_{PCA}$, the artifical operon of $_{pnpt}$-npt-upp from pMO746 and a region from downstream $hgcB_{PCA}$; for marker exchange deletion mutagenesis; $Sp^r$ and $Km^r$ | This study |
| pORNL1003 | Partial bla and pMB1 ori from pUC19 with $hgcA_{PCA}$ including a 762 bp region upstream from $hgcA_{PCA}$, the $Sp^r$ cassette from pMO719, and a 995 bp region downstream from $hgcB_{PCA}$; for marker exchange insertion of $hgcA_{PCA}$; $Sp^r$ | This study |
| pORNL1004 | Partial bla and pMB1 ori from pUC19 with $hgcA_{PCA}$ and hgcBPCA including a 762 bp region upstream from $hgcA_{PCA}$, the $Sp^r$ cassette from pMO719, and a 995 bp region downstream from $hgcB_{PCA}$; for marker exchange insertional complementation of $hgcAB_{PCA}$; $Sp^r$ | This study |

TABLE 5-continued

Plasmids

| Plasmid | Characteristics | Source or Reference |
|---|---|---|
| pORNL1005 | Partial bla and pMB1 ori from pUC19 with hgcB$_{PCA}$ including a 762 bp region upstream from hgcA$_{PCA}$, the Sp$^r$ cassette from pMO719, and a 995 bp region downstream from hgcB$_{PCA}$; for marker exchange insertion of hgcB$_{PCA}$; Sp$^r$ | This study |

[A] The neomycin phosphotransferase II (nptII) gene was used in selection of transformed bacteria. It was initially isolated from the transposon Tn5 that was present in E. coli K12. The nptII gene codes for the aminoglycoside 3'-phosphotransferase (denoted aph(3')-II or NPTII) enzyme. Transcription is from the P$_{nptII}$ that also drives the transcription of upp from Desulfovibrio vulgaris Hildenborough encoding uracil phosphoribosyltransferase. This artificial operon was used in marker exchange deletion strains, although the upp was not used in these studies.
[B] aadA encodes aminoglycoside 3'-adenyltransferase that confers spectinomycin resistance.

TABLE 6

Primers and Probes

| Primer name | Primer ID | Primer Sequence (5'->3') | Application |
|---|---|---|---|
| | | Primers used in the deletion strategies | |
| D132-1056-upF | P1$_{ND132}$ | GCCTTTTGCTGGCCTT TTGCTCACATGTCTAC AGGGAGCCGTTCACC (SEQ ID NO. 9) | For amplification of hgcA upstream region from ND132 gDNA with D132-1056-upR3 to obtain pMO4650 and pMO4651. Underlined portion used as overhang for SLIC with Sp$^R$, pUCori fragment (Spec$^R$pUC-R). Amplification of Southern probe for confirmation of hgcA, hgcAB cluster and hgcB deletions, forward |
| GSU-1440-upF | P1$_{GSU}$ | GCCTTTTGCTGGCCTT TTGCTCACATCTGCGT CAAGGGAATGCTCCG (SEQ ID NO. 10) | For amplification of hgcA upstream region from G. sulfurreducens (PCA) gDNA with GSU-1440-upR3 to obtain pORNL1001 and pORNL1002 (also referred to herein as pMO4653 and pMO4654). Underlined portion used as overhang for SLIC with Spec$^R$, pUCori fragment (SpecRpUC-R). Used as forward primer for PCR and sequence based confirmation of the GSUΔ1440 and GSUΔ144-1441 deletions |
| D132-1056-upR3 | P2$_{ND132}$ | CGACAAGATATTCGGC ACCAAGTAAGCAAAG GGTTCCACGGCGTAGC (SEQ ID NO. 11) | For amplification of hgcA upstream region from ND132 gDNA with D132-1056-upF from ND132 gDNA to obtain pMO4650 and pMO4651. Underlined portion used as overhang for SLIC with Km$^R$, upp fragment (Kan-Upp-Cterm-R). Amplification of Southern probe for confirmation of hgcA, hgcAB cluster and hgcB deletions. reverse |
| GSU-1440-upR | P2$_{GSU}$ | TCGCCTTCTTGACGAG TTCTTCTGAGGTATCG AGCCAACGAAGAAAA CCC (SEQ ID NO. 12) | For amplification of hgcA upstream region from PCA gDNA with GSU-1440-upF to obtain pORNL1001 and pORNL1002. Underlined portion complements 5' region of Tn5 Kan$^r$ expression cassette for SLIC assembly |
| D132-1056-dwF | P5$_{ND132}$ | CCCAGCTGGCAATTCC GGCCGGGAGACTGAT GATGAAGGATTTCC | For amplification of hgcA downstream region from ND132 gDNA with D132-1057-dwR |

TABLE 6-continued

Primers and Probes

| Primer name | Primer ID | Primer Sequence (5'->3') | Application |
|---|---|---|---|
| | | (SEQ ID NO. 13) | from ND132 gDNA to obtain pMO4650. Underlined portion used as overhang for SLIC with $Km^R$, upp fragment (Kan-Tx-F), forward |
| GSU-1440-dnF | $P5_{GSU}$ | CCCAGCTGGCAATTCC GGCCGGGAGGTAGCA TGATCGG (SEQ ID NO. 14) | For amplification of hgcA downstream region from PCA gDNA with GSU1441-dnR to obtain pORNL1001. Underlined portion complements $Km^R$ expression cassette for SLIC assembly |
| D132-1057-dwF | $P3_{ND132}$ | CCCAGCTGGCAATTCC GGTGCTGCTAGTCCGC GAGCA (SEQ ID NO. 15) | For amplification of hgcB downstream region from ND132 gDNA with D132-1057-dwR from ND132 gDNA to obtain pMO4651. Underlined portion used as overhang for SLIC with $Km^R$, upp fragment (Kan-Tx-F), forward |
| GSU-1441-dnF | $P3_{GSU}$ | CCCAGCTGGCAATTCC GGTGATCCATCTTGGG TGGAATTTCGTGA (SEQ ID NO. 16) | For amplification of hgcB downstream region from PCA gDNA with GSU-1441-dnR to obtain pORNL1002. Underlined portion used as overhang for SLIC with $Km^R$, upp fragment (Kan-Tx-F), forward |
| D132-1057-dwR | $P4_{ND132}$ | CGAGGCATTTCTGTCC TGGCTGGCCAGACGAC GCACAGGGAAT (SEQ ID NO. 17) | For amplification of hgcA downstream region from ND132 gDNA with either D132-1056-dwF or D132-1057-dwF to obtain pMO4650 and pMO4651, respectively. Underlined portion used as overhang for SLIC with $Sp^R$, pUC ori fragment (SpecRpUC-F), reverse |
| GSU-1441-dnR | $P4_{GSU}$ | CGAGGCATTTCTGTCC TGGCTGGGAGATTAGC ATCGGTAGCGGCC (SEQ ID NO. 18) | For amplification of hgcAB downstream region from PCA gDNA with either GSU-1440dnF or GSU-1441-dnF to obtain pORNL1001 and pORNL1002, respectively. Underlined portion used as overhang for SLIC with $Sp^R$, pUC ori fragment (SpecRpUC-F), reverse |
| D132-1057-upF | $P6_{ND132}$ | GCCTTTTGCTGGCCTT TTGCTCACATGCTACG CCGTGGAACCCTTTG (SEQ ID NO. 19) | For amplification of hgcB upstream region from ND132 gDNA with D132-1057-upR to obtain pMO4652. Underlined portion used as overhang for SLIC with $Sp^R$, pUCori fragment (SpecRpUC-R), forward |
| D132-1057-upR | $P7_{GSU}$ | CGACAAGATATTCGGC ACCAAGTAAGGGAAA TCCTTCATCATCAGTC TCCCGG (SEQ ID NO. 20) | For amplification of hgcB upstream region from ND132 gDNA with D132-1057-upF from ND132 gDNA to obtain pMO4652. Underlined portion used as overhang for SLIC with $Km^R$, upp fragment (Kan-Upp-Cterm-R), reverse |
| Probe_Up1440-F | | ACCTGCGTCAAGGGA ATGCT (SEQ ID NO. 21) | For amplification of hgcA upstream region from G. sulfurreducens (PCA) gDNA with Probe_Up1440-R to obtain 783 bp upstream region of hgcA as |

TABLE 6-continued

Primers and Probes

| Primer name | Primer ID | Primer Sequence (5'->3') | Application |
|---|---|---|---|
| | | | Southern probe for confirmation of hgcA$_{PCA}$, hgcA$_{PCA}$/hgcB$_{PCA}$ cluster restoration. |
| Probe_Up1440-R | | GCGTGGAGATGACCG GCA (SEQ ID NO. 22) | For amplification of hgcA upstream region from *G. sulfurreducens* (PCA) gDNA with Probe_Up1440-F to obtain 783 bp upstream region of hgcA as Southern probe for confirmation of hgcA$_{PCA}$, hgcA$_{PCA}$/hgcB$_{PCA}$ cluster restoration. |
| SpecRpUC-F | | CCAGCCAGGACAGAA ATGCCTCG (SEQ ID NO. 23) | For amplification of Sp$^R$ and pUC ori from pMO9075 to obtain pMO4650, pMO4651 and pMO4652. Used as overhang for SLIC, forward |
| SpecRpUC-R | | ATGTGAGCAAAAGGC CAGCAAAAGGC (SEQ ID NO. 24) | For amplification of Spec$^R$ and pUCori from pMO9075 to obtain pMO4650, pMO4651 and pMO4652. Used as overhang for SLIC, reverse |
| SpecRpUC-up | | GGGAAACGCCTGGTAT CTTTATAGTCCT (SEQ ID NO. 25) | For amplification of Sp$^R$ and pUC ori from pMO719 to obtain pMO4653 and pMO4654. Used as overhang for SLIC, forward |
| Kan-Tx-F | | CCGGAATTGCCAGCTG GG (SEQ ID NO. 26) | For amplification of Km$^R$ from pMO719 to obtain pMO4650, pMO4651, pMO4652, pORNL1001 and pORNL1002. Used as overhang for SLIC, forward. Used in PCR confirmation of GSU1440 and GSU1440-1441 deletions |
| Kan-Upp-Cterm-R | | CTTACTTGGTGCCGAA TATCTTGTCG (SEQ ID NO. 27) | For amplification of Km$^R$ from pMO719 to obtain pMO4650, pMO4651 and pMO4652. Used as overhang for SLIC, reverse |
| Kan-R | | TCAGAAGAACTCGTCA AGAAGGCGA (SEQ ID NO. 28) | For amplification of Km$^R$ from pMO719 to obtain pORNL1001 and pORNL1002. Complements GSU1440-upR for SLIC assembly. Used in PCR confirmation of GSU1440 and GSU1440-1441 deletions |
| pUC ori-out | | GGGAAACGCCTGGTAT CTTTATAGT (SEQ ID NO. 29) | For sequencing of the downstream regions of the deletion cassette of plasmids pMO4650, pMO4651 and pMO4652, forward |
| pUC ori-F | | GGCCTTTTGCTGGCCT TTTGCTCACA (SEQ ID NO. 30) | For colony PCR, screen of pMO4650, pMO4651 and pMO4652 deletion cassette, reverse |
| Kan-int-Fwd-rev-comp | | CTCATCCTGTCTCTTG ATCAGATCT (SEQ ID NO. 31) | For sequencing of the downstream regions of the deletion cassette of pMO4650, pMO4651 and pMO4652, reverse |
| DvH-Upp gene Cterm-out | | GCTGAAGCGCATCGTG GACAA (SEQ ID NO. 32) | For sequencing of the upstream regions of the deletion cassette of pMO4650, pMO4651 and pMO4652, forward |

TABLE 6-continued

Primers and Probes

| Primer name | Primer ID | Primer Sequence (5'->3') | Application |
|---|---|---|---|
| pMO719 XbaI-Dwn | | TGGGTTCGTGCCTTCA TCCG (SEQ ID NO. 33) | For colony PCR screen of pMO4650, pMO4651, pMO4652, pMO4653, and pMO4654 and sequencing of the upstream regions of the deletion cassette of plasmids pMO4650, pMO4651, pMO4652, reverse |

Primers used in the complementation strategies

| Primer name | Primer ID | Primer Sequence (5'->3') | Application |
|---|---|---|---|
| Upstr 1056 w/ pUC ovhg-F | $P8_{ND132}$ | GCCTTTTGCTGGCCTT TTGCTCACATGTCTAC AGGGAGCCGTTCACC (SEQ ID NO. 34) | For amplification of hgcA upstream region and $hgcAB_{ND132}$ with 1057-Up-Spec ovhg-R to prepare restorative constructs pMO4661 and pMO4662. Underlined portion used as overhang for SLIC assembly with Amp-pUC-F/pUC-Amp-R product. |
| pUC ovhg_1057-Up-F | $P9_{ND132}$ | GCCTTTTGCTGGCCTT TTGCTCACATGCTACG CCGTGGAACCCTTTG (SEQ ID NO. 35) | For amplification of 20 bp hgcA upstream region and $hgcAB_{ND132}$ with 1057-Up-Spec ovhg-R to prepare restorative constructs pMO4659. Underlined portion used as overhang for SLIC assembly with Amp-pUC-F/ pUC-Amp-R product. |
| GSU1440-upF2 | $P8_{GSU}$ | CAGCGTTTCTGGGTGA GCCTGCGTCAAGGGA ATGCTCCG (SEQ ID NO. 36) | For amplification of hgcA upstream region and GSU1440 or both GSU1440 and GSU1441 from G. sulfurreducens (PCA) gDNA with GSU-1440-R2 or GSU1441-R2 to prepare restorative constructs pORNL1003 and pORNL1004, respectively (also referred to herein as pHg::1440 and pHg::1440-1441). Underlined portion used as overhang for Gibson assembly with pUC19oriF/pUC19AmpR product. |
| 1057-Up-Spec ovhg-R | $P10_{ND132}$ | AGTTGCGTGAGCGCAT ACGCTACTTGCATCTA GCAGCAGGCGGCGTC GATCTTGC (SEQ ID NO. 37) | For amplification of hgcA upstream region and $hgcAB_{ND132}$ with Upstr 1056 w/pUC ovhg-F or GSU1441-R2 to prepare restorative constructs pMO4659, pMO4661 and pMO4662. Underlined portion used as overhang for SLIC assembly with Spec-F/Spec-R product. |
| GSU1440-R2 | $P9_{GSU}$ | CGAGGCATTTCTGTCC TGGCTGGTCACCGATC ATGCTACCTCCCGGT (SEQ ID NO. 38) | For amplification of hgcA with GSU1440-upF2 to prepare pORNL1003. The overhang region complements an upstream segment of the $Sp^R$ cassette. |
| GSU1441-R2 | $P10_{GSU}$ | CGAGGCATTTCTGTCC TGGCTGGTCTCACGAA ATTCCACCCAAGATGG ATCA (SEQ ID NO. 39) | For amplification of hgcA and hgcB with GSU1440-upF2 to prepare complementation construct pORNL1004. The overhang region complements an upstream segment of the $Sp^R$ cassette. |
| Spec ovhg_1056-Dw-F | $P11_{ND132}$ | CGAGATCACCAAGGT AGTCGGCAAATAATGC TGCTAGTCCGCGAGCA GG (SEQ ID NO. 40) | For amplification of 789 bp hgcB downstream region with 1056-Dw-Amp ovhg-R to prepare restorative constructs pMO4659, pMO4661, pMO4662 and as |

TABLE 6-continued

Primers and Probes

| Primer name | Primer ID | Primer Sequence (5'->3') | Application |
|---|---|---|---|
| | | | Southern probe for confirmation of hgcB$_{ND132}$, hgcAB$_{ND132}$ restoration. Underlined portion used as overhang for SLIC assembly with Spec-F/Spec-R product |
| GSU1441-dnF2 | P11$_{GSU}$ | GTAGTCGGCAAATAAC CCTCGAGCTGATCCAT CTTGGGTGGAATTTCG TGA (SEQ ID NO. 41) | Used with GSU1441-dnR2 to amplify a 995 bp segment of the *G. sulfurreducens* PCA genome located immediately downstream of hgAB to support recombination. Underlined portion used as overhang for Gibson assembly with the downstream terminal nucleotides of the Sp$^R$ cassette in pORNL1003, pORNL1004 and pORNL1005. |
| 1056-Dw-Amp ovhg-R | P12$_{ND132}$ | TATATACTTTAGATTG ATTTAAAACTTCCCAG ACGACGCACAGGGAA T (SEQ ID NO. 42) | For amplification of 789 bp hgcB downstream region with 1056-Dw-Amp ovhg-R to prepare restorative constructs pMO4659, pMO4661, pMO4662 and as Southern probe for confirmation of hgcB$_{ND132}$, hgcAB$_{ND132}$ restoration. Underlined portion used as overhang for SLIC assembly with Amp-pUC-F/ pUC-Amp-R product. |
| GSU1441-dnR2 | P12$_{GSU}$ | GTGAGCTGATACCGCT CGCGAGATTAGCATCG GTAGCGGCC (SEQ ID NO. 43) | Used with GSU1441-dnF2 to amplify a 995 bp segment of the *G. sulfurreducens* PCA genome located immediately downstream of hgcAB to support recombination. Underlined portion used as overhang for Gibson assembly with the pUC19 backbone segment. |
| Amp-pUC-F | | GAAGTTTTAAATCAAT CTAAAGTATATATGAG TAAACTTGGTCTGA (SEQ ID NO. 44) | For amplification of a 1681 bp fragment of pUC ori and a part of the bla gene (Ap$^r$) to serve as a backbone segment of pMO4659, pMO4661 and pMO4662, forward |
| pUC19oriF | | GCGAGCGGTATCAGCT CAC (SEQ ID NO. 45) | Used with pUC19-Amp-R for amplification of a 1685 bp fragment of pUC19 containing the ori sequence and a part of the bla gene to serve as a backbone segment of pORNL1003, pORNL1004 and pORNL1005. |
| pUC-Amp-R | | ATGTGAGCAAAAGGC CAGCAAAAGG (SEQ ID NO. 46) | For amplification of a 1681 bp fragment containing pUC ori sequence and a part of the bla gene (Ap$^r$) to serve as a backbone segment of pMO4659, pMO4661 and pMO4662, reverse |
| pUC19AmpR | | GCTCACCCAGAAACGC TG (SEQ ID NO. 47) | Used with pUC19oriF for amplification of a 1685 bp fragment of pUC19 containing the ori sequence and a part of the bla gene to serve as a backbone segment of pORNL1003, pORNL1004 and pORNL1005. |
| Spec-F | | ATGCAAGTAGCGTATG CGCTCAC (SEQ ID NO. 48) | For amplification of Sp$^R$ marker from pMO719 to obtain pMO4659, pMO4661 and |

TABLE 6-continued

Primers and Probes

| Primer name | Primer ID | Primer Sequence (5'->3') | Application |
|---|---|---|---|
| | | | pMO4662. Used as overhang for SLIC, forward |
| SpecRpUC-F | | CCAGCCAGGACAGAA ATGCCTCG (SEQ ID NO. 49) | Used with primer ext specRrev for amplification of a Sp$^R$ marker from pMO719 used in preparation of complementation constructs pORNL1003, pORNL1004 and pORNL1005. |
| Spec-R | | TTATTTGCCGACTACC TTGGTGATCTCG (SEQ ID NO. 50) | For amplification of Sp$^R$ marker from pMO719 to obtain pMO4659, pMO4661 and pMO4662. Used as overhang for SLIC, reverse |
| ext specR rev | | GCTCGAGGGTTATTTG CCGACTAC (SEQ ID NO. 51) | Used with primer SpecRpUC-F for amplification of a Sp$^R$ marker from pMO719 used in preparation of complementation constructs pORNL1003, pORNL1004 and pORNL1005. |
| Spec-out-R3 | | TAACGCGCTTGCTGCT TGGA (SEQ ID NO. 52) | External reverse sequencing primer for the determination of the hgcA upstream homologous recombination region and hgcAB genes of the complementation constructs pMO4659, pMO4661 and pMO4662. |
| Spec-out-F | | AGCCCGTCATACTTGA AGCTAGACA (SEQ ID NO. 53) | External forward sequencing primer for the determination of the hgcB downstream homologous recombination region of the complementation constructs pMO4659, pMO4661 and pMO4662. |
| Amp-out-R2 | | ATGGTAAGCCCTCCCG TATCGT (SEQ ID NO. 54) | External reverse sequencing primer for the determination of the hgcB downstream homologous recombination region of the complementation constructs pMO4659, pMO4661 and pMO4662. |
| DND1056 Cys-Thr F | | CAACGTCTGGACCGCG GCGGGCAA (SEQ ID NO. 55) | Internal forward sequencing primer for the determination of the hgcA gene of the complementation constructs pMO4659, pMO4661 and pMO4662. |
| 1056 R interior Seq primer | | CCTCGTCCGCCTTGTT GCCGTTG (SEQ ID NO. 56) | Internal reverse sequencing primer for the determination of the hgcA gene of the complementation constructs pMO4659, pMO4661 and pMO4662. |
| pMO719 Xba dwn | | TGGGTTCGTGCCTTCA TCCG (SEQ ID NO. 57) | Sequencing primer to confirm inserts into pMO9075 |
| GSU1440-upF | | CTGCGTCAAGGGAATG CTCCG (SEQ ID NO. 58) | External forward sequencing primer for complementation constructs pORNL1003, and pORNL1004. |
| hgcA456F | | CATGATCGCGACGTCT GC (SEQ ID NO. 59) | Internal forward sequencing primer for complementation constructs pORNL1003, and pORNL1004. |

TABLE 6-continued

Primers and Probes

| Primer name | Primer ID | Primer Sequence (5'->3') | Application |
|---|---|---|---|
| hgcA473R | | GCAGACGTCCGCATCA TG (SEQ ID NO. 60) | Internal reverse sequencing primer for complementation constructs pORNL1003, and pORNL1004. |
| GSU1441-dnR | | GAGATTAGCATCGGTA GCGGCG (SEQ ID NO. 61) | External reverse sequencing primer for complementation constructs pORNL1003, and pORNL1004. |
| GSU1440R | | CCGATCATGCTACCTC CCGGTC (SEQ ID NO. 62) | External and internal reverse sequencing primer for complementation constructs pORNL1003, and pORNL1004 respectively. |
| Probe_Dw-1441-F | | GGCATGAAGAACAGA AGT TCCATGGT (SEQ ID NO. 63) | For amplification of hgcB downstream region from G. sulfurreducens (PCA) gDNA with Probe_Up1441-R to obtain 570 bp upstream region of hgcA as Southern probe for confirmation of $hgcA_{PCA}$, $hgcA_{PCA}/hgcB_{PCA}$ cluster restoration. |
| Probe_Dw-1441-R | | GAGATTAGCATCGGTA GCGGCC (SEQ ID NO. 64) | For amplification of hgcB upstream region from G. sulfurreducens (PCA) gDNA with Probe_Up1441-F to obtain 570 bp upstream region of hgcA as Southern probe for confirmation of $hgcA_{PCA}$, $hgcA_{PCA}/hgcB_{PCA}$ cluster restoration. |

The underlined primer's sequences correspond to the DNA overhang's regions used in the PCR fragments for SLIC or Gibson assemblages.

EXAMPLE 4

Expression and Purification of the HgcA Wild-Type and C93T Mutant Cobalamin-Binding Domains Expression: The coding sequence for the HgcA wild-type and a C93T mutant cobalamin-binding domain (residues 1-166) of ND 132 were codon-optimized for E. coli and inserted into a pJexpress401 expression plasmid containing the T5 promoter and the kanamycin resistance gene (DNA 2.0, Inc., USA). The pJexpress401 plasmid constructs encoding the wild-type and C93T mutant cobalamin-binding domains were each transformed into E. coli BL21 cells (Novagen, USA). Cell cultures were grown in 1 L of LB broth supplemented with 0.2 M D-sorbitol and 5.0 mM betaine containing 30 μg/ml kanamycin. Cultures were grown at 37° C. to an $OD_{600}$ of 0.6 and protein expression was induced with 1 mM isopropyl β-D-1-thiogalactopyranoside (IPTG) for 3 hours with shaking at 225 rpm. The cultures were harvested by centrifugation (8,000×g, 4° C., 10 min), the bacterial cell pellets were resuspended in lysis buffer containing 50 mM Na HEPES pH 7.5, 5 mM EDTA, and 5 mM DTT (10 ml/g wet cell pellet) and stored at −80° C. The frozen cell suspensions were thawed at room temperature with stirring in the presence of 1× Halt Protease Inhibitor Cocktail (Thermo Scientific, USA) and lysed by two passes in a French Press (Thermo Spectronic, USA) at 13,000 lb/in² at 4° C. The cell debris was removed by centrifugation (20,000×g, 4° C., 45 min) and the resulting supernatant was decanted and filtered through a 0.45 μm syringe filter (Millipore, USA).

Purification: The protein purification steps were performed at room temperature using an ÄKTA Purifier system (GE Healthcare, USA) and were essentially identical for the purification of both the wild-type and C93T mutant cobalamin-binding domain of HgcA. The filtered supernatant was diluted with buffer A (25 mM Na HEPES pH 7.5, 3 mM DTT) and loaded onto a 20 ml HiLoad SP Sepharose HP column (GE Healthcare, USA) pre-quilibrated with buffer A. The protein was eluted at ~500 mM NaCl using a linear gradient of buffer B (buffer A+1 M NaCl). The fractions containing wild-type or C93T mutant cobalamin-binding domain were pooled and loaded (6 ml injections) onto a HiPrep 26/60 Sephacryl S-100 HR gel filtration column (GE Healthcare, USA) pre-equilibrated with buffer C (25 mM Na HEPES pH 7.5, 200 mM NaCl). The gel filtration fractions corresponding to the major absorbance peak at 280 nm were pooled and homogeneity of the purified protein was confirmed by SDS-PAGE. The purified protein was concentrated using 10 kDa MWCO Amicon Ultra-15 Centrifugal Filter Units (Millipore, USA). Protein concentrations were determined by the Bradford assay using bovine serum albumin as standard.

UV/VIS Spectroscopy: To characterize the Co coordination environment in HgcA, the UV/Vis spectra were obtained for the wild-type cobalamin-binding domain of HgcA and the C93T mutant domain purified as above, in each case, with a bound aquacob(III)alamin cofactor.

Hydroxocobalamin hydrochloride was obtained from MP Biomedicals, LLC, Solon, Ohio, U.S.A. The wild-type and C93T mutant corrinoid-binding domain of HgcA$_{ND132}$ were incubated with a five-fold molar excess of aquacobalamin in a buffer of 25 mM Na HEPES, pH 7.5 at room temperature overnight. Excess aquacobalamin was removed by ultrafiltration using 10 kDa MWCO Amicon Ultra-15 Centrifugal Filter Units (Millipore, Billerica, Mass., U.S.A.). Absorption spectra were recorded at a protein concentration of 0.42 mg/ml each for wild-type HgcA$_{ND132}$-CBD and C93T HgcA$_{ND132}$-CBD using an Agilent Cary 60 UV/Vis spectrophotometer (Agilent Technologies, Inc., Santa Clara, Calif., U.S.A.).

The C93T mutant exhibits significant shifts in the energy bands and absorption intensities relative to the wildtype, suggesting that the single-residue mutation results in a significant change in the Co coordination environment. The UV-Vis spectra are consistent with "Cys-on" coordination of the corrinoid cofactor in HgcA.

REFERENCES

Altschul S F, Madden T L, Schaffer A A, Zhang J, Zhang Z, Miller W, Lipman D J (1997) Gapped BLAST and PSI-BLAST: A new generation of protein database search programs. Nucleic Acids Res 25:3389-3402.

Banerjee R, Ragsdale S W (2003) The many faces of vitamin B12: catalysis by cobalamin-dependent enzymes. Annu Rev Biochem 72:209-247.

Bender K S, Yen H C, Hemme C L, Yang Z, He Z, He Q, Zhou J, Huang K H, Alm E J, Hazen T C, Arkin A P, Wall J D (2007) Analysis of a ferric uptake regulator (Fur) mutant of *Desulfovibrio vulgaris* Hildenborough. Appl Environ Microbiol 73:5389-5400.

Bradford M M (1976) A rapid and sensitive method for the quantitation of microgram quantities of protein utilizing the principle of protein-dye binding. Anal Biochem 72:248-254.

Brandis, A. and Thauer, R. K. (1981) Growth of *Desulfovibrio* Species on Hydrogen and Sulfate as Sole Energy-Source. J Gen Microbiol. 126, 249-252

Bridou R, Monperrus M, Gonzalez P R, Guyoneaud R, Amouroux D (2011) Simultaneous determination of mercury methylation and demethylation capacities of various sulfate-reducing bacteria using species-specific isotopic tracers. Environ Toxicol Chem 30:337-344.

Brown S D, Gilmour C C, Kucken A M, Wall J D, Elias D A, Brandt C C, Podar M, Chertkov O, Held B, Bruce D C, Detter J C, Tapia R, Han C S, Goodwin L A, Cheng J F, Pitluck S, Woyke T, Mikhailova N, Ivanova N N, Han J, Lucas S, Lapidus A L, Land M L, Hauser U, Palumbo A V (2011) Genome sequence of the mercury-methylating strain *Desulfovibrio desulfuricans* ND132. J Bacteriol 193:2078-2079.

Choi S C, Chase T, Bartha R (1994a) Metabolic Pathways Leading to Mercury Methylation in *Desulfovibrio desulfuricans* LS. Appl Environ Microbiol 60:4072-4077.

Choi S C, Chase T, Jr., Bartha R (1994b) Enzymatic catalysis of mercury methylation by *Desulfovibrio desulfuricans* LS. Appl Environ Microbiol 60:1342-1346.

Compeau G C, Bartha R (1985) Sulfate-Reducing Bacteria: Principal Methylators of Mercury in Anoxic Estuarine Sediment. Appl Environ Microbiol 50:498-502.

Coppi, M V, Leang, C, Sandler, S J, Lovley D R (2001) Development of a genetic system for *Geobacter sulfurreducens*. Appl. Environ. Microbiol. 67:3180.

Ekstrom E B, Morel F M, Benoit J M (2003) Mercury methylation independent of the acetyl-coenzyme A pathway in sulfate-reducing bacteria. Appl Environ Microbiol 69:5414-5422.

Galushko A S, Schink B (2000) Oxidation of acetate through reactions of the citric acid cycle by *Geobacter sulfurreducens* in pure culture and in syntrophic coculture. Arch Microbiol 174:314-321.

Gibson D G et al. (2009) Enzymatic assembly of DNA molecules up to several hundred kilobases. Nat. Methods 6:343.

Gilmour C C, Elias D A, Kucken A M, Brown S D, Palumbo A V, Schadt C W, Wall J D (2011) Sulfate-reducing bacterium *Desulfovibrio desulfuricans* ND132 as a model for understanding bacterial mercury methylation. Appl Environ Microbiol 77:3938-3951.

Goetzl S, Jeoung J H, Hennig S E, Dobbek H (2011) Structural basis for electron and methyl-group transfer in a methyltransferase system operating in the reductive acetyl-CoA pathway. J Mol Biol 411:96-109.

Graham, A. M., Bullock, A. L., Maizel, A. C., Elias, D. A. and Gilmour, C. C. (2012) Detailed Assessment of the Kinetics of Hg-Cell Association, Hg Methylation, and Methylmercury Degradation in Several *Desulfovibrio* Species. Appl Environ Microb. 78, 7337-7346

Heyes A, Mason R P, Kim E-H, Sunderland E (2006) Mercury methylation in estuaries: Insights from using measuring rates using stable mercury isotopes. Mar Chem 102:134-147.

Hill H A O, Pratt J M, Ridsdale S, Williams F R (1970) Kinetics of Substitution of Co-Ordinated Carbanions in Cobalt (Iii) Corrinoids. J Chem Soc Chem Comm 341.

Hintelmann H, Evans R D (1997) Application of stable isotopes in environmental tracer studies—Measurement of monomethylmercury (CH3Hg+) by isotope dilution ICP-MS and detection of species transformation. J Anal Chem 358:378-385.

Hintelmann H, Ogrinc N (2003) Determination of stable mercury isotopes by ICP/MS and their application in environmental studies. In: Biogeochemistry of Environmentally Important Trace Elements, ACS Sym. Ser. 835: 321-338.

Keller K L, Bender K S, Wall J D (2009) Development of a markerless genetic exchange system for *Desulfovibrio vulgaris* Hildenborough and its use in generating a strain with increased transformation efficiency. Appl Environ Microbiol. 75, 7682-7691.

Keller K L, Wall J D, Chhabra S (2011) Methods for engineering sulfate reducing bacteria of the genus *Desulfovibrio*. Methods Enzymol 497:503-517.

Kerin E J, Gilmour C C, Roden E, Suzuki M T, Coates J D, Mason R P (2006) Mercury methylation by dissimilatory iron-reducing bacteria. Appl Environ Microbiol 72:7919-7921.

King, J. K., Kostka, J. E., Frischer, M. E. and Saunders, F. M. (2000) Sulfate-reducing bacteria methylate mercury at variable rates in pure culture and in marine sediments. Appl Environ Microbiol. 66, 2430-2437

Kung Y, Ando N, Doukov T I, Blasiak L C, Bender G, Seravalli J, Ragsdale S W, Drennan C L (2012) Visualizing molecular juggling within a B 12-dependent methyltransferase complex. Nature 484:265-269.

Li M Z, S. J. Elledge S J (2007) Harnessing homologous recombination in vitro to generate recombinant DNA via SLIC. Nat. Methods 4:251.

Pagani I, Liolios K, Jansson J, Chen I M, Smirnova T, Nosrat B, Markowitz V M, Kyrpides N C (2012) The Genomes OnLine Database (GOLD) v.4: status of genomic and metagenomic projects and their associated metadata. Nucleic Acids Res 40:D571-579.

Polson, S. M., Hansen, L. and Marzilli, L. G. (1997) The first X-ray structural evidence demonstrating thiolate coordination in an organocobalt B-12 model complex: Implications for methionine synthase. Inorganic Chemistry. 36, 307-313

Ragsdale S W (2008a) Catalysis of methyl group transfers involving tetrahydrofolate and B(12). Vitam Horm 79:293-324.

Ragsdale S W, Lindahl P A, Munck E (1987) Mossbauer, E P R, and optical studies of the corrinoid/iron-sulfur protein involved in the synthesis of acetyl coenzyme A by *Clostridium thermoaceticum*. J Biol Chem 262:14289-14297.

Ragsdale S W, Pierce E (2008b) Acetogenesis and the Wood-Ljungdahl pathway of CO(2) fixation. Biochim Biophys Acta 1784:1873-1898.

Ranchou-Peyruse M, Monperrus M, Bridou R, Duran R, Amouroux D, Salvado J C, Guyoneaud R (2009) Overview of Mercury Methylation Capacities Among Anaerobic Bacteria Including Representatives of the Sulphate-Reducers: Implications for Environmental Studies. Geomicrobiol J 26:1-8.

Sali A, Blundell T L (1993) Comparative protein modelling by satisfaction of spatial restraints. J. Mol. Biol. 234:779-815.

Schrauzer G N, Seck J A, Holland R J, Beckham T M, Rubin E M, Sibert J W (1973) Reductive dealkylation of alkylcobaloximes, alkylcobalamins, and related compounds: Simulation of corrin dependent reductase and methyl group transfer reactions. Bioinorganic Chemistry 2:93-124.

Shen M Y, Sali A (2006) Statistical potential for assessment and prediction of protein structures. Protein Sci 15:2507-2524.

Sigrist C J, Cerutti L, Hulo N, Gattiker A, Falquet L, Pagni M, Bairoch A, Bucher P (2002) PROSITE: a documented database using patterns and profiles as motif descriptors. Brief Bioinform 3:265-24.

Sturup S, Chen C, Jukosky J, Folt C (2005) Isotope dilution quantification of $^{200}Hg^{2+}$ and $CH_3^{201}Hg^+$ enriched species-specific tracers in aquatic systems by cold vapor ICPMS and algebraic de-convoluting. Int J Mass Spec 242:225-231.

Svetlitchnaia T, Svetlitchnyi V, Meyer O, Dobbek H (2006) Structural insights into methyltransfer reactions of a corrinoid iron-sulfur protein involved in acetyl-CoA synthesis. Proc Natl Acad Sci USA 103:14331-14336.

USEPA (2001) Method 1630: Methyl mercury in water by distillation, aqueous ethylation, purge and trap, and CVAFS.

USEPA (2002) Method 1631, Revision E: Mercury in Water by Oxidation, Purge and Trap, and Cold Vapor Atomic Fluorescence Spectrometry.

Wood J M (1974) Biological cycles for toxic elements in the environment. Science 183:1049-1052.

Wood J M, Kennedy F S, Rosen C G (1968) Synthesis of methyl-mercury compounds by extracts of a methanogenic bacterium. Nature 220:173-174.

Yu R-Q, Flanders J R, Mack E E, Turner R, Mirza M B, Barkay T (2012) Contribution of Coexisting Sulfate and Iron Reducing Bacteria to Methylmercury Production in Freshwater River Sediments. Environ Sci Technol. 46:2684.

Zane G M, Yen H C, Wall J D (2011) Effect of the deletion of qmoABC and the promoter-distal gene encoding a hypothetical protein on sulfate reduction in *Desulfovibrio vulgaris* Hildenborough. Appl Environ Microbiol 76:5500-5509.

---

We claim:

1. A method which comprises
   (a) preparing nucleic acids from a sample; and
   (b) detecting the presence of an hgcA gene, an hgcB gene or both in said sample by hybridization with at least one nucleic acid probe specific for hgcA, at least one nucleic acid probe specific for hgcB, or both, wherein the at least one nucleic acid probe specific for hgcA hybridizes to a region of a nucleic acid wherein said region consists of contiguous nucleotides 256-300 of SEQ ID NO: 2, and the at least one nucleic acid probe specific for hgcB hybridizes to a region of a nucleic acid wherein said region consists of contiguous nucleotides 58-90 or 148-180 of SEQ ID NO: 4.

2. The method of claim 1, wherein said detection is by a microarray-based assay, PCR, in situ hybridization, southern blot, or northern blot.

3. The method of claim 1, wherein the at least one nucleic acid probe specific for hgcA and the at least one nucleic acid probe specific for hgcB are selected from the group consisting of
   (a) an isolated nucleic acid which comprises a fragment of contiguous hgcA or hgcB nucleotides wherein the contiguous hgcA nucleotides hybridize to a region of a nucleic acid wherein said region consists of contiguous nucleotides 256-300 of SEQ ID NO: 2, and the contiguous hgcB nucleotides hybridize to a region of a nucleic acid wherein said region consists of contiguous nucleotides 58-90 or 148-180 of SEQ ID NO: 4;
   (b) contiguous nucleotides selected from the group consisting of a nucleotide sequence for hgcA shown in FIG. 5 (SEQ ID NO. 2), a nucleotide sequence encoding the amino acid sequence for HgcA shown in FIG. 5 (SEQ ID. NO. 3), a nucleotide sequence encoding an amino acid sequence for HgcA from any one of the microorganisms listed in Table 1, and a consensus nucleotide sequence that detects hgcA from microorganisms capable of mercury methylation, wherein the contiguous nucleotides hybridize to a region of a nucleic acid wherein said region consists of contiguous nucleotides 256-300 of SEQ ID NO: 2;
   (c) contiguous nucleotides selected from the group consisting of contiguous nucleotides 256-300 shown in FIG. 5 (SEQ ID NO. 2) or the equivalent nucleotides from any one of the microorganisms listed in Table 1, the nucleotides which encode amino acids 86-100 shown in FIG. 5 (SEQ ID NO. 3) or the equivalent nucleotides from any one of the microorganisms listed in Table 1, and the nucleotides which encode the consensus amino acid sequence TxG[I,V]N[V,I]WCA[A,G]GK[G,D,K,Q]xF or the consensus amino acid sequence TxG[I,V]N[V,I]WCA[A,G]GK[G,D,K,Q][T,L,S,A]F (SEQ ID NOS. 8 or 204, respectively) where x is any amino acid and amino acids in brackets represent alternative choices for the given position, wherein the contiguous nucleotides hybridize to a region of a nucleic acid wherein said region consists of contiguous nucleotides 256-300 of SEQ ID NO: 2;

(d) contiguous nucleotides selected from the group consisting of a nucleotide sequence for hgcB shown in FIG. 6 (SEQ ID NO. 4), a nucleotide sequence encoding the amino acid sequence for HgcB shown in FIG. 6 (SEQ ID NO. 5), a nucleotide sequence encoding an amino acid sequence for HgcB from any one of the microorganisms listed in Table 1, and a consensus nucleotide sequence that detects hgcB from microorganisms capable of mercury methylation, wherein the contiguous nucleotides hybridize to a region of a nucleic acid wherein said region consists of contiguous nucleotides 58-90 or 148-180 of SEQ ID NO: 4;

(e) contiguous nucleotides selected from the group consisting of contiguous nucleotides 58-90 or 148-180 shown in FIG. 6 (SEQ ID NO. 4) or the equivalent nucleotides from any one of the microorganisms listed in Table 1, the nucleotides encode amino acids 20-30 or 50-60 shown in FIG. 6 (SEQ ID NO. 5) or the equivalent nucleotides from any one of the microorganisms listed in Table 1, and the equivalent nucleotides from an hgcB gene from any of the microbes in Table 1, wherein the contiguous nucleotides hybridize to a region of a nucleic acid wherein said region consists of contiguous nucleotides 58-90 or 148-180 of SEQ ID NO: 4;

(f) a set of PCR primers capable of amplifying all or at least 25 bp fragment of a microbial hgcA gene, said gene including upstream and downstream regions associated with expression of the hgcA coding sequence, wherein said microbial hgcA gene is from a microorganism listed in Table 1, wherein the PCR primers hybridize to a region of a nucleic acid wherein said region consists of contiguous nucleotides 256-300 of SEQ ID NO: 2; and (g) a set of PCR primers capable of amplifying all or at least 25 bp fragment of a microbial hgcB gene, said gene including upstream and downstream regions associated with expression of the hgcB coding sequence, wherein said microbial hgcB gene is from a microorganism listed in Table 1, wherein the PCR primers hybridize to a region of a nucleic acid wherein said region consists of contiguous nucleotides 58-90 or 148-180 of SEQ ID NO: 4.

4. The method of claim 1, wherein nucleic acid in said sample is assayed to identify the species of microorganism by performing sequencing analysis of the nucleic acid, or performing hybridization using species-specific nucleic acid probes.

* * * * *

SEQUENCE LISTING

```
<160> NUMBER OF SEQ ID NOS: 205

<210> SEQ ID NO 1
<211> LENGTH: 125
<212> TYPE: PRT
<213> ORGANISM: Carboxydothermus hydrogenoformus

<400> SEQUENCE: 1

Pro Lys Val Tyr Glu Ile Leu Asn Pro Gly Pro Asp Ala Pro Val Phe
1               5                   10                  15

Ile Thr Thr Asn Phe Ser Leu Thr Tyr Phe Cys Val Ala Gly Asp Val
                20                  25                  30

Glu Gly Ala Arg Ile Pro Ala Tyr Ile Leu Pro Val Asp Thr Asp Gly
            35                  40                  45

Thr Ser Val Leu Thr Ala Trp Ala Ala Gly Lys Phe Thr Pro Glu Lys
        50                  55                  60

Ile Ala Gln Phe Leu Lys Glu Ser Gly Ile Ala Glu Lys Val Asn His
65                  70                  75                  80

Arg Lys Ala Ile Leu Pro Gly Gly Val Ala Val Leu Ser Gly Lys Leu
                85                  90                  95

Gln Glu Leu Ser Gly Trp Glu Ile Leu Val Gly Pro Arg Glu Ser Ser
            100                 105                 110

Gly Ile Asn Ser Phe Ile Lys Gln Arg Trp Asn Val Ala
        115                 120                 125
```

```
<210> SEQ ID NO 2
<211> LENGTH: 1017
<212> TYPE: DNA
<213> ORGANISM: Desulfovibrio desulfuricans
<220> FEATURE:
<221> NAME/KEY: CDS
<222> LOCATION: (1)..(1014)

<400> SEQUENCE: 2
```

| | | | | | | | | | | | | | | | | |
|---|---|---|---|---|---|---|---|---|---|---|---|---|---|---|---|---|
| gtg | gac | ggc | ttc | gcc | agg | acg | gcg | gcc | ggt | ccg | gtg | ccg | cgc | gtg | cgc | 48 |
| Val | Asp | Gly | Phe | Ala | Arg | Thr | Ala | Ala | Gly | Pro | Val | Pro | Arg | Val | Arg | |
| 1 | | | | 5 | | | | | 10 | | | | | 15 | | |
| acc | tat | ctg | cgc | cgc | gac | gac | cgc | gtg | ggc | gat | ctg | cgc | gcc | cgc | ctg | 96 |
| Thr | Tyr | Leu | Arg | Arg | Asp | Asp | Arg | Val | Gly | Asp | Leu | Arg | Ala | Arg | Leu | |
| | | | 20 | | | | | 25 | | | | | 30 | | | |
| ggc | acc | aac | cgc | cac | gac | ttc | aag | gtg | gtg | cct | ggc | ctg | tac | tgc | gtg | 144 |
| Gly | Thr | Asn | Arg | His | Asp | Phe | Lys | Val | Val | Pro | Gly | Leu | Tyr | Cys | Val | |
| | | 35 | | | | | 40 | | | | | 45 | | | | |
| ggc | gag | ccc | gac | cgg | acc | tcg | ccg | gtc | ctg | gtc | acc | gcc | aac | tac | aag | 192 |
| Gly | Glu | Pro | Asp | Arg | Thr | Ser | Pro | Val | Leu | Val | Thr | Ala | Asn | Tyr | Lys | |
| 50 | | | | | 55 | | | | | 60 | | | | | | |
| ctg | acc | ttc | gac | acc | ctg | cgc | gag | cgg | ctg | acc | tcc | atc | gac | gcc | tgg | 240 |
| Leu | Thr | Phe | Asp | Thr | Leu | Arg | Glu | Arg | Leu | Thr | Ser | Ile | Asp | Ala | Trp | |
| 65 | | | | | 70 | | | | | 75 | | | | | 80 | |
| ctg | ctg | gtg | gtg | gat | acg | cgc | ggc | atc | aac | gtc | tgg | tgc | gcg | gcg | ggc | 288 |
| Leu | Leu | Val | Val | Asp | Thr | Arg | Gly | Ile | Asn | Val | Trp | Cys | Ala | Ala | Gly | |
| | | | | 85 | | | | | 90 | | | | | 95 | | |
| aag | ggg | ttg | ttc | acc | gct | tcc | gag | gtg | gcc | ttc | agc | gtc | aac | gcg | gtc | 336 |
| Lys | Gly | Leu | Phe | Thr | Ala | Ser | Glu | Val | Ala | Phe | Ser | Val | Asn | Ala | Val | |
| | | | | 100 | | | | | 105 | | | | | 110 | | |
| cgg | ctg | cac | cag | gtg | gtc | gag | cac | cgc | gaa | ctg | atc | ctg | ccc | cag | ctg | 384 |
| Arg | Leu | His | Gln | Val | Val | Glu | His | Arg | Glu | Leu | Ile | Leu | Pro | Gln | Leu | |
| | | 115 | | | | | 120 | | | | | 125 | | | | |
| gcc | gcc | acg | ggc | gtg | gcc | gcc | cgc | gag | gtg | gag | cgc | atc | tgc | ggc | ttc | 432 |
| Ala | Ala | Thr | Gly | Val | Ala | Ala | Arg | Glu | Val | Glu | Arg | Ile | Cys | Gly | Phe | |
| | 130 | | | | | 135 | | | | | 140 | | | | | |
| aag | gtc | cta | tgg | ggc | ccc | atc | cgg | gcc | agg | gac | ctg | ccc | gcc | ttc | ctg | 480 |
| Lys | Val | Leu | Trp | Gly | Pro | Ile | Arg | Ala | Arg | Asp | Leu | Pro | Ala | Phe | Leu | |
| 145 | | | | | 150 | | | | | 155 | | | | | 160 | |
| cgc | aac | ggc | aac | aag | gcg | gac | gag | gcc | atg | cgc | ggc | gtg | acc | ttc | acc | 528 |
| Arg | Asn | Gly | Asn | Lys | Ala | Asp | Glu | Ala | Met | Arg | Gly | Val | Thr | Phe | Thr | |
| | | | | 165 | | | | | 170 | | | | | 175 | | |
| tta | cgc | gaa | cgg | gcc | gcg | ctc | atc | ccg | gtg | gaa | ctg | tac | cag | ctg | cgc | 576 |
| Leu | Arg | Glu | Arg | Ala | Ala | Leu | Ile | Pro | Val | Glu | Leu | Tyr | Gln | Leu | Arg | |
| | | | 180 | | | | | 185 | | | | | 190 | | | |
| aag | ccc | ctg | ttc | gcg | gcc | att | ccg | ctg | ctc | ttc | ctg | ctc | tcc | gcc | ctg | 624 |
| Lys | Pro | Leu | Phe | Ala | Ala | Ile | Pro | Leu | Leu | Phe | Leu | Leu | Ser | Ala | Leu | |
| | | 195 | | | | | 200 | | | | | 205 | | | | |
| ggg | ccg | gac | ctc | ttt | tcc | ccg | ccc | gcc | ctg | tgg | cag | cgg | ggc | atc | tcg | 672 |
| Gly | Pro | Asp | Leu | Phe | Ser | Pro | Pro | Ala | Leu | Trp | Gln | Arg | Gly | Ile | Ser | |
| | 210 | | | | | 215 | | | | | 220 | | | | | |
| gcc | gtc | acg | gcc | acc | ctg | gtc | ggc | gcg | ctg | gcg | ggc | agc | gtg | ctg | gtc | 720 |
| Ala | Val | Thr | Ala | Thr | Leu | Val | Gly | Ala | Leu | Ala | Gly | Ser | Val | Leu | Val | |
| 225 | | | | | 230 | | | | | 235 | | | | | 240 | |
| ccc | ctg | ttc | ctg | aac | agg | ctg | ccc | tgg | cgg | cag | ttc | tgg | ccc | aaa | ggc | 768 |
| Pro | Leu | Phe | Leu | Asn | Arg | Leu | Pro | Trp | Arg | Gln | Phe | Trp | Pro | Lys | Gly | |
| | | | | 245 | | | | | 250 | | | | | 255 | | |
| gcg | ctg | gtc | ggc | ggg | gcc | gcc | ggg | acc | ctg | gcg | gca | ctg | tac | ctg | ccc | 816 |
| Ala | Leu | Val | Gly | Gly | Ala | Ala | Gly | Thr | Leu | Ala | Ala | Leu | Tyr | Leu | Pro | |
| | | | | 260 | | | | | 265 | | | | | 270 | | |

```
gtg cac ggc tgg gcc gac ccc ctg gcc ctg acg ctc tgg gcc acg gcc    864
Val His Gly Trp Ala Asp Pro Leu Ala Leu Thr Leu Trp Ala Thr Ala
        275                 280                 285 gtg gcc tcc tgg cag gcc atg aat ttc acg ggc tcg acc ccc tac acc    912
Val Ala Ser Trp Gln Ala Met Asn Phe Thr Gly Ser Thr Pro Tyr Thr
290                 295                 300 tcg ccc tcg ggc gtg gaa aag gaa atg cgc cgg ggc atg ccg ctc cag    960
Ser Pro Ser Gly Val Glu Lys Glu Met Arg Arg Gly Met Pro Leu Gln
305                 310                 315                 320 gca ctg gcc gcg ctg gcc gcc gca ggg ctg tgg ctg gcc ggg ccg ttc   1008
Ala Leu Ala Ala Leu Ala Ala Ala Gly Leu Trp Leu Ala Gly Pro Phe
                325                 330                 335 ctc ggt tga                                                        1017
Leu Gly
```

<210> SEQ ID NO 3
<211> LENGTH: 338
<212> TYPE: PRT
<213> ORGANISM: Desulfovibrio desulfuricans

<400> SEQUENCE: 3

```
Val Asp Gly Phe Ala Arg Thr Ala Ala Gly Pro Val Pro Arg Val Arg
1               5                   10                  15

Thr Tyr Leu Arg Arg Asp Asp Arg Val Gly Asp Leu Arg Ala Arg Leu
            20                  25                  30

Gly Thr Asn Arg His Asp Phe Lys Val Val Pro Gly Leu Tyr Cys Val
        35                  40                  45

Gly Glu Pro Asp Arg Thr Ser Pro Val Leu Val Thr Ala Asn Tyr Lys
50                  55                  60

Leu Thr Phe Asp Thr Leu Arg Glu Arg Leu Thr Ser Ile Asp Ala Trp
65                  70                  75                  80

Leu Leu Val Val Asp Thr Arg Gly Ile Asn Val Trp Cys Ala Ala Gly
                85                  90                  95

Lys Gly Leu Phe Thr Ala Ser Glu Val Ala Phe Ser Val Asn Ala Val
            100                 105                 110

Arg Leu His Gln Val Val Glu His Arg Glu Leu Ile Leu Pro Gln Leu
        115                 120                 125

Ala Ala Thr Gly Val Ala Arg Glu Val Glu Arg Ile Cys Gly Phe
    130                 135                 140

Lys Val Leu Trp Gly Pro Ile Arg Ala Arg Asp Leu Pro Ala Phe Leu
145                 150                 155                 160

Arg Asn Gly Asn Lys Ala Asp Glu Ala Met Arg Gly Val Thr Phe Thr
                165                 170                 175

Leu Arg Glu Arg Ala Ala Leu Ile Pro Val Glu Leu Tyr Gln Leu Arg
            180                 185                 190

Lys Pro Leu Phe Ala Ala Ile Pro Leu Leu Phe Leu Leu Ser Ala Leu
        195                 200                 205

Gly Pro Asp Leu Phe Ser Pro Pro Ala Leu Trp Gln Arg Gly Ile Ser
    210                 215                 220

Ala Val Thr Ala Thr Leu Val Gly Ala Leu Ala Gly Ser Val Leu Val
225                 230                 235                 240

Pro Leu Phe Leu Asn Arg Leu Pro Trp Arg Gln Phe Trp Pro Lys Gly
                245                 250                 255

Ala Leu Val Gly Gly Ala Ala Gly Thr Leu Ala Ala Leu Tyr Leu Pro
            260                 265                 270

Val His Gly Trp Ala Asp Pro Leu Ala Leu Thr Leu Trp Ala Thr Ala
```

```
                275                 280                 285
Val Ala Ser Trp Gln Ala Met Asn Phe Thr Gly Ser Thr Pro Tyr Thr
    290                 295                 300

Ser Pro Ser Gly Val Glu Lys Glu Met Arg Arg Gly Met Pro Leu Gln
305                 310                 315                 320

Ala Leu Ala Ala Leu Ala Ala Gly Leu Trp Leu Ala Gly Pro Phe
                325                 330                 335

Leu Gly

<210> SEQ ID NO 4
<211> LENGTH: 288
<212> TYPE: DNA
<213> ORGANISM: Desulfovibrio desulfuricans
<220> FEATURE:
<221> NAME/KEY: CDS
<222> LOCATION: (1)..(285)

<400> SEQUENCE: 4 atg aag gat ttc cgc tat atc gac ggc gtg tcc agc ctg gcg ctc gac      48
Met Lys Asp Phe Arg Tyr Ile Asp Gly Val Ser Ser Leu Ala Leu Asp
1               5                  10                  15 acg gac aag tgc gtg ggc tgc ggg tcc tgc gtg gac gtc tgc ccg cac      96
Thr Asp Lys Cys Val Gly Cys Gly Ser Cys Val Asp Val Cys Pro His
            20                  25                  30 cgc atc ctg gcc gtg cgg gag cgc aag acg acc atc ctc gac ttc gac     144
Arg Ile Leu Ala Val Arg Glu Arg Lys Thr Thr Ile Leu Asp Phe Asp
        35                  40                  45 gcc tgc atg gag tgc ggg gcc tgc gcc cgc aac tgc ccg gtg gag gcg     192
Ala Cys Met Glu Cys Gly Ala Cys Ala Arg Asn Cys Pro Val Glu Ala
    50                  55                  60 atc acc gtc acc ccc ggc acg ggc tgc gcc gcc tac ctg gtc tcg gtc     240
Ile Thr Val Thr Pro Gly Thr Gly Cys Ala Ala Tyr Leu Val Ser Val
65                  70                  75                  80 tgg ctg cac cgg ctg acc ggg cgc aag atc gac gcc gcc tgc tgc tag     288
Trp Leu His Arg Leu Thr Gly Arg Lys Ile Asp Ala Ala Cys Cys
                85                  90                  95

<210> SEQ ID NO 5
<211> LENGTH: 95
<212> TYPE: PRT
<213> ORGANISM: Desulfovibrio desulfuricans

<400> SEQUENCE: 5

Met Lys Asp Phe Arg Tyr Ile Asp Gly Val Ser Ser Leu Ala Leu Asp
1               5                  10                  15

Thr Asp Lys Cys Val Gly Cys Gly Ser Cys Val Asp Val Cys Pro His
            20                  25                  30

Arg Ile Leu Ala Val Arg Glu Arg Lys Thr Thr Ile Leu Asp Phe Asp
        35                  40                  45

Ala Cys Met Glu Cys Gly Ala Cys Ala Arg Asn Cys Pro Val Glu Ala
    50                  55                  60

Ile Thr Val Thr Pro Gly Thr Gly Cys Ala Ala Tyr Leu Val Ser Val
65                  70                  75                  80

Trp Leu His Arg Leu Thr Gly Arg Lys Ile Asp Ala Ala Cys Cys
                85                  90                  95

<210> SEQ ID NO 6
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      consensus sequence for hgcA cobalamin-binding
      domain
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (6)..(6)
<223> OTHER INFORMATION: Ala or Gly

<400> SEQUENCE: 6

Asn Xaa Trp Cys Ala Xaa Gly Lys
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus sequence for hgcB [4Fe-4S] clusters
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid

<400> SEQUENCE: 7

Cys Xaa Xaa Cys Xaa Xaa Cys Xaa Xaa Xaa Cys
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence for hgcA cobalamin-binding
      domain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Ile or Val
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (10)..(10)
<223> OTHER INFORMATION: Ala or Gly
<220> FEATURE:
<221> NAME/KEY: MOD_RES
<222> LOCATION: (13)..(13)
<223> OTHER INFORMATION: Gly, Asp, Lys or Gln
<220> FEATURE:
<221> NAME/KEY: MOD_RES
<222> LOCATION: (14)..(14)
<223> OTHER INFORMATION: Any amino acid

<400> SEQUENCE: 8
```

```
Thr Xaa Gly Xaa Asn Xaa Trp Cys Ala Xaa Gly Lys Xaa Xaa Phe
1               5                   10                  15
```

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      ND132 hgcA upstream forward primer

<400> SEQUENCE: 9 gcctttgct ggccttttgc tcacatgtct acagggagcc gttcacc         47

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence: Synthetic
      GSU hgcA upstream forward primer

<400> SEQUENCE: 10 gcctttgct ggccttttgc tcacatctgc gtcaagggaa tgctccg         47

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      ND132 hgcA upstream reverse primer

<400> SEQUENCE: 11
cgacaagata ttcggcacca agtaagcaaa gggttccacg gcgtagc         47

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      GSU hgcA upstream reverse primer

<400> SEQUENCE: 12
tcgccttctt gacgagttct tctgaggtat cgagccaacg aagaaaaccc         50

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      ND132 hgcA downstream forward primer

<400> SEQUENCE: 13
cccagctggc aattccggcc gggagactga tgatgaagga tttcc         45

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      GSU hgcA downstream forward primer

<400> SEQUENCE: 14

```
cccagctggc aattccggcc gggaggtagc atgatcgg                              38
```

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      ND132 hgcB downstream forward primer

<400> SEQUENCE: 15

```
cccagctggc aattccggtg ctgctagtcc gcgagca                               37
```

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      GSU hgcB downstream forward primer

<400> SEQUENCE: 16

```
cccagctggc aattccggtg atccatcttg ggtggaattt cgtga                      45
```

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      ND132 hgcA downstream reverse primer

<400> SEQUENCE: 17

```
cgaggcattt ctgtcctggc tggccagacg acgcacaggg aat                        43
```

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      GSU hgcA/hgcB downstream reverse primer

<400> SEQUENCE: 18

```
cgaggcattt ctgtcctggc tgggagatta gcatcggtag cggcc                      45
```

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: Synthetic
      ND132 hgcB upstream forward primer

<400> SEQUENCE: 19

```
gcctttrgct ggccttttgc tcacatgcta cgccgtggaa ccctttg                    47
```

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: Synthetic
      ND132 hgcB upstream reverse primer

<400> SEQUENCE: 20
cgacaagata ttcggcacca agtaagggaa atccttcatc atcagtctcc cgg         53

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      GSU hgcA upstream forward probe

<400> SEQUENCE: 21
acctgcgtca agggaatgct                                              20

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      GSU hgcA upstream reverse probe

<400> SEQUENCE: 22
gcgtggagat gaccggca                                                18

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      SpecR forward primer

<400> SEQUENCE: 23
ccagccagga cagaaatgcc tcg                                          23

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      SpecR reverse primer

<400> SEQUENCE: 24
atgtgagcaa aaggccagca aaaggc                                       26

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      SpecR forward primer

<400> SEQUENCE: 25
gggaaacgcc tggtatcttt atagtcct                                     28

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      KanR forward primer

<400> SEQUENCE: 26
ccggaattgc cagctggg                                                18

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      KanR reverse primer

<400> SEQUENCE: 27
cttacttggt gccgaatatc ttgtcg                                    26

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      KanR primer

<400> SEQUENCE: 28
tcagaagaac tcgtcaagaa ggcga                                     25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      pUC sequencing primer

<400> SEQUENCE: 29
gggaaacgcc tggtatcttt atagt                                     25

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      pUC colony reverse primer

<400> SEQUENCE: 30
ggccttttgc tggccttttg ctcaca                                    26

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      Kan reverse sequencing primer

<400> SEQUENCE: 31
ctcatcctgt ctcttgatca gatct                                     25

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      DvH forward sequencing primer

<400> SEQUENCE: 32
gctgaagcgc atcgtggaca a                                         21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      pMO719 colony reverse primer

<400> SEQUENCE: 33
tgggttcgtg ccttcatccg                                                 20

<210> SEQ ID NO 34
<211> LENGTH: 47
<212> TYPE: DNA
<213> ORGANISM: Artificial Sequence
<220> FEATURE:
<223> OTHER INFORMATION: Description of Artificial Sequence: Synthetic
      ND132 hgcA/hgcAB upstream primer

<400> SEQUENCE: 34 gcctttgct ggccttttgc tcacatgtct acagggagcc gttcacc                    47

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic
      ND132 hgcA/hgcAB upstream primer

<400> SEQUENCE: 35 gcctttgct ggccttttgc tcacatgcta cgccgtggaa ccctttg                    47

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic
      GSU hgcA/hgcAB upstream primer

<400> SEQUENCE: 36
cagcgtttct gggtgagcct gcgtcaaggg aatgctccg                            39

<210> SEQ ID NO 37
<211> LENGTH: 55
<212> TYPE: DNA
<213> ORGANISM: Artificial Sequence
<220> FEATURE:
<223> OTHER INFORMATION: Description of Artificial Sequence: Synthetic
      ND132 hgcA/hgcAB upstream primer

<400> SEQUENCE: 37
agttgcgtga gcgcatacgc tacttgcatc tagcagcagg cggcgtcgat cttgc          55

<210> SEQ ID NO 38
<211> LENGTH: 47
<212> TYPE: DNA
<213> ORGANISM: Artificial Sequence
<220> FEATURE:
<223> OTHER INFORMATION: Description of Artificial Sequence: Synthetic
      GSU hgcA primer

<400> SEQUENCE: 38
cgaggcattt ctgtcctggc tggtcaccga tcatgctacc tcccggt                   47

```
<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      GSU hgcA/hgcB primer

<400> SEQUENCE: 39
cgaggcattt ctgtcctggc tggtctcacg aaattccacc caagatggat ca        52

<210> SEQ ID NO 40
<211> LENGTH: 49
<212> TYPE: DNA
<213> ORGANISM: Artificial Sequence
<220> FEATURE:
<223> OTHER INFORMATION: Description of Artificial Sequence: Synthetic
      ND132 hgcB downstream primer

<400> SEQUENCE: 40
cgagatcacc aaggtagtcg gcaaataatg ctgctagtcc gcgagcagg             49

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      GSU hgcAB downstream primer

<400> SEQUENCE: 41
gtagtcggca ataaccctc gagctgatcc atcttgggtg gaatttcgtg a           51

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: Synthetic
      ND132 hgcB downstream primer

<400> SEQUENCE: 42
tatatacttt agattgattt aaaacttccc agacgacgca cagggaat              48

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Synthetic
      GSU hgcAB downstream primer

<400> SEQUENCE: 43
gtgagctgat accgctcgcg agattagcat cggtagcggc c                     41

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence: Synthetic
      pUC19 ori forward primer

<400> SEQUENCE: 44
gaagttttaa atcaatctaa agtatatatg agtaaacttg gtctga                46

<210> SEQ ID NO 45
```

```
<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      pUC19 ori primer

<400> SEQUENCE: 45
gcgagcggta tcagctcac                                                      19

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      pUC ori reverse primer

<400> SEQUENCE: 46
atgtgagcaa aaggccagca aaagg                                               25

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      pUC ori primer

<400> SEQUENCE: 47
gctcacccag aaacgctg                                                       18

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      SpecR forward primer

<400> SEQUENCE: 48
atgcaagtag cgtatgcgct cac                                                 23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      SpecR primer

<400> SEQUENCE: 49
ccagccagga cagaaatgcc tcg                                                 23

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      SpecR reverse primer

<400> SEQUENCE: 50
ttatttgccg actaccttgg tgatctcg                                            28

<210> SEQ ID NO 51
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      SpecR primer

<400> SEQUENCE: 51
gctcgagggt tatttgccga ctac                                            24

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Spec out reverse sequencing primer

<400> SEQUENCE: 52
taacgcgctt gctgcttgga                                                 20

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      Spec out forward sequencing primer

<400> SEQUENCE: 53
agcccgtcat acttgaagct agaca                                           25

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      Amp out reverse sequencing primer

<400> SEQUENCE: 54
atggtaagcc ctcccgtatc gt                                              22

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      internal forward sequencing primer

<400> SEQUENCE: 55
caacgtctgg accgcggcgg gcaa                                            24

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      internal reverse sequencing primer

<400> SEQUENCE: 56
cctcgtccgc cttgttgccg ttg                                             23

<210> SEQ ID NO 57
<211> LENGTH: 20
<212> TYPE: DNA
```

<213> ORGANISM: Artificial Sequence
<220> FEATURE:
<223> OTHER INFORMATION: Description of Artificial Sequence: Synthetic
     pMO719 sequencing primer

<400> SEQUENCE: 57
tgggttcgtg ccttcatccg                                        20

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
     GSU external forward sequencing primer

<400> SEQUENCE: 58
ctgcgtcaag ggaatgctcc g                                      21

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
     GSU internal forward sequencing primer

<400> SEQUENCE: 59
catgatcgcg acgtctgc                                          18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
     GSU internal reverse sequencing primer

<400> SEQUENCE: 60
gcagacgtcc gcatcatg                                          18

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
     GSU external reverse sequencing primer

<400> SEQUENCE: 61
gagattagca tcggtagcgg cg                                     22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
     GSU external/internal reverse sequencing primer

<400> SEQUENCE: 62
ccgatcatgc tacctcccgg tc                                     22

<210> SEQ ID NO 63
<211> LENGTH: 26
<212> TYPE: DNA
<213> ORGANISM: Artificial Sequence

```
<220> FEATURE:
<223> OTHER INFORMATION: Description of Artificial Sequence: Synthetic
      GSU hgcB downstream probe

<400> SEQUENCE: 63
ggcatgaaga acagaagttc catggt                                          26

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      GSU hgcB upstream probe

<400> SEQUENCE: 64
gagattagca tcggtagcgg cc                                              22

<210> SEQ ID NO 65
<211> LENGTH: 28
<212> TYPE: PRT
<213> ORGANISM: Desulfovibrio desulfuricans

<400> SEQUENCE: 65

Ala Trp Leu Leu Val Asp Thr Arg Gly Ile Asn Val Trp Cys Ala
1               5                   10                  15
Ala Gly Lys Gly Leu Phe Thr Ala Ser Glu Val Ala
            20                  25

<210> SEQ ID NO 66
<211> LENGTH: 28
<212> TYPE: PRT
<213> ORGANISM: Desulfovibrio aespoeensis

<400> SEQUENCE: 66

Ala Trp Leu Leu Val Ala Asp Thr Arg Gly Ile Asn Ile Trp Cys Ala
1               5                   10                  15
Ala Gly Lys Asp Leu Phe Ser Thr Asp Glu Val Ala
            20                  25

<210> SEQ ID NO 67
<211> LENGTH: 28
<212> TYPE: PRT
<213> ORGANISM: Desulfovibrio africanus

<400> SEQUENCE: 67

Ala Trp Leu Leu Val Leu Asp Thr Lys Gly Val Asn Val Trp Cys Ala
1               5                   10                  15
Ala Gly Lys Lys Thr Phe Ser Ala Glu Glu Ile Val
            20                  25

<210> SEQ ID NO 68
<211> LENGTH: 28
<212> TYPE: PRT
<213> ORGANISM: Desulfomicrobium baculatum

<400> SEQUENCE: 68

Leu Trp Leu Leu Val Thr Asp Thr Arg Gly Ile Asn Ile Trp Cys Ala
1               5                   10                  15
Gly Gly Lys Gly Thr Phe Asn Ala Ala Gly Ile Ala
            20                  25

<210> SEQ ID NO 69
```

```
<210> SEQ ID NO 69
<211> LENGTH: 28
<212> TYPE: PRT
<213> ORGANISM: Desulfonatronospira thiodismutans

<400> SEQUENCE: 69

Cys Trp Leu Leu Val Val Glu Thr Tyr Gly Ile Asn Val Trp Cys Ala
1               5                   10                  15

Ala Gly Lys Gln Ser Phe Asn Ala Gly Glu Val Ala
            20                  25

<210> SEQ ID NO 70
<211> LENGTH: 28
<212> TYPE: PRT
<213> ORGANISM: Desulfonatronum lacustre

<400> SEQUENCE: 70

Ala Trp Leu Leu Val Ala Asp Thr Arg Gly Ile Asn Val Trp Cys Ala
1               5                   10                  15

Gly Gly Lys Gly Ser Phe Asn Ala Glu Ala Val Ala
            20                  25

<210> SEQ ID NO 71
<211> LENGTH: 28
<212> TYPE: PRT
<213> ORGANISM: Desulfovibrio oxyclinae

<400> SEQUENCE: 71

Val Trp Leu Leu Val Ile Asp Thr Arg Gly Ile Asn Val Trp Cys Ala
1               5                   10                  15

Ala Gly Lys Ser Leu Phe Ser Thr Asp Glu Val Ile
            20                  25

<210> SEQ ID NO 72
<211> LENGTH: 28
<212> TYPE: PRT
<213> ORGANISM: Desulfobulbus propionicus

<400> SEQUENCE: 72

Ala Trp Leu Leu Val Val Asp Thr Arg Gly Ile Asn Val Trp Cys Ala
1               5                   10                  15

Ala Gly Lys Gly Thr Phe Ser Thr Trp Glu Val Ile
            20                  25

<210> SEQ ID NO 73
<211> LENGTH: 29
<212> TYPE: PRT
<213> ORGANISM: Desulfobacterium sp.

<400> SEQUENCE: 73

Val Trp Leu Leu Val Leu Glu Thr Tyr Gly Ile Asn Val Trp Cys Ala
1               5                   10                  15

Ala Gly Lys Gly Thr Phe Ser Thr Gln Glu Leu Val Leu
            20                  25

<210> SEQ ID NO 74
<211> LENGTH: 28
<212> TYPE: PRT
<213> ORGANISM: Geobacter sulfurreducens

<400> SEQUENCE: 74

Ile Trp Leu Leu Val Leu Glu Thr His Gly Ile Asn Val Trp Cys Ala
1               5                   10                  15
```

Ala Gly Lys Gly Thr Phe Gly Thr Asp Glu Ile Val
            20                  25

<210> SEQ ID NO 75
<211> LENGTH: 28
<212> TYPE: PRT
<213> ORGANISM: Geobacter metallireducens

<400> SEQUENCE: 75

Val Trp Phe Leu Val Leu Glu Thr Phe Gly Ile Asn Val Trp Cys Ala
1               5                   10                  15

Ala Gly Lys Gly Thr Phe Gly Thr Asp Glu Leu Val
            20                  25

<210> SEQ ID NO 76
<211> LENGTH: 28
<212> TYPE: PRT
<213> ORGANISM: Geobacter sulfurreducens

<400> SEQUENCE: 76

Ile Trp Leu Leu Val Leu Glu Thr His Gly Ile Asn Val Trp Cys Ala
1               5                   10                  15

Ala Gly Lys Gly Thr Phe Gly Thr Asp Glu Ile Val
            20                  25

<210> SEQ ID NO 77
<211> LENGTH: 28
<212> TYPE: PRT
<213> ORGANISM: Geobacter metallireducens

<400> SEQUENCE: 77

Val Trp Phe Leu Val Leu Glu Thr Phe Gly Ile Asn Val Trp Cys Ala
1               5                   10                  15

Ala Gly Lys Gly Thr Phe Gly Thr Asp Glu Leu Val
            20                  25

<210> SEQ ID NO 78
<211> LENGTH: 28
<212> TYPE: PRT
<213> ORGANISM: Geobacter sp.

<400> SEQUENCE: 78

Val Trp Leu Leu Val Leu Glu Thr His Gly Ile Asn Val Trp Cys Ala
1               5                   10                  15

Ala Gly Lys Gly Thr Phe Gly Thr Glu Glu Leu Val
            20                  25

<210> SEQ ID NO 79
<211> LENGTH: 28
<212> TYPE: PRT
<213> ORGANISM: Geobacter sp.

<400> SEQUENCE: 79

Val Trp Leu Leu Val Leu Glu Thr Tyr Gly Ile Asn Val Trp Cys Ala
1               5                   10                  15

Ala Gly Lys Gly Thr Phe Gly Thr Gly Glu Leu Val
            20                  25

<210> SEQ ID NO 80
<211> LENGTH: 28
<212> TYPE: PRT
<213> ORGANISM: Geobacter sp.

```
<400> SEQUENCE: 80

Val Trp Leu Leu Val Leu Glu Thr Phe Gly Ile Asn Val Trp Cys Ala
1               5                   10                  15

Ala Gly Lys Gly Thr Phe Gly Thr Asp Glu Leu Val
            20                  25

<210> SEQ ID NO 81
<211> LENGTH: 28
<212> TYPE: PRT
<213> ORGANISM: Geobacter uraniireducens

<400> SEQUENCE: 81

Val Trp Leu Leu Val Leu Glu Thr Phe Gly Ile Asn Val Trp Cys Ala
1               5                   10                  15

Ala Gly Lys Gly Thr Phe Gly Thr Asp Glu Leu Val
            20                  25

<210> SEQ ID NO 82
<211> LENGTH: 28
<212> TYPE: PRT
<213> ORGANISM: Geobacter bemidjiensis

<400> SEQUENCE: 82

Val Trp Leu Leu Val Leu Glu Thr Phe Gly Ile Asn Val Trp Cys Ala
1               5                   10                  15

Ala Gly Lys Gly Thr Phe Gly Thr Asp Glu Leu Val
            20                  25

<210> SEQ ID NO 83
<211> LENGTH: 28
<212> TYPE: PRT
<213> ORGANISM: Syntrophorhabdus aromaticivorans

<400> SEQUENCE: 83

Gly Trp Ile Leu Val Leu Asp Thr Leu Gly Ile Asn Val Trp Cys Ala
1               5                   10                  15

Ala Gly Lys Gly Thr Phe Gly Thr Asp Glu Leu Val
            20                  25

<210> SEQ ID NO 84
<211> LENGTH: 28
<212> TYPE: PRT
<213> ORGANISM: Desulfomonile tiedjei

<400> SEQUENCE: 84

Ala Trp Leu Leu Val Leu Asp Thr Gln Gly Ile Asn Val Trp Cys Ala
1               5                   10                  15

Ala Gly Lys Gly Thr Phe Gly Thr Asp Glu Leu Val
            20                  25

<210> SEQ ID NO 85
<211> LENGTH: 28
<212> TYPE: PRT
<213> ORGANISM: Syntrophus aciditrophicus

<400> SEQUENCE: 85

Ala Trp Ile Leu Val Leu Asp Thr Asn Gly Ile Asn Val Trp Cys Ala
1               5                   10                  15

Ala Gly Lys Gly Ala Phe Gly Thr Glu Glu Val Val
            20                  25
```

```
<210> SEQ ID NO 86
<211> LENGTH: 28
<212> TYPE: PRT
<213> ORGANISM: Unknown
<220> FEATURE:
<223> OTHER INFORMATION: Description of Unknown: Delta
      proteobacterium peptide

<400> SEQUENCE: 86

Ala Trp Ile Leu Val Leu Asp Thr Asp Gly Ile Asn Val Trp Cys Ala
1               5                   10                  15

Ala Gly Lys Gly Ser Phe Gly Thr Ala Asn Leu Val
            20                  25

<210> SEQ ID NO 87
<211> LENGTH: 28
<212> TYPE: PRT
<213> ORGANISM: Unknown
<220> FEATURE:
<223> OTHER INFORMATION: Description of Unknown: Delta
      proteobacterium peptide

<400> SEQUENCE: 87

Val Trp Ile Leu Val Leu Asp Thr Asn Gly Ile Asn Val Trp Cys Ala
1               5                   10                  15

Ala Gly Lys Gly Thr Phe Gly Thr Glu Glu Leu Val
            20                  25

<210> SEQ ID NO 88
<211> LENGTH: 28
<212> TYPE: PRT
<213> ORGANISM: Acetivibrio cellulolyticus

<400> SEQUENCE: 88

Ala Trp Ile Leu Val Leu Asp Thr Arg Gly Ile Asn Val Trp Cys Ala
1               5                   10                  15

Ala Gly Lys Gly Thr Phe Gly Thr Arg Glu Ile Val
            20                  25

<210> SEQ ID NO 89
<211> LENGTH: 28
<212> TYPE: PRT
<213> ORGANISM: Dehalobacter restrictus

<400> SEQUENCE: 89

Ala Trp Ile Leu Val Leu Asp Thr Lys Gly Ile Asn Val Trp Cys Ala
1               5                   10                  15

Ala Gly Lys Gly Thr Phe Gly Thr Ala Glu Leu Ser
            20                  25

<210> SEQ ID NO 90
<211> LENGTH: 28
<212> TYPE: PRT
<213> ORGANISM: Desulfitobacterium dehalogenans

<400> SEQUENCE: 90

Thr Trp Ile Leu Val Leu Asp Thr Lys Gly Ile Asn Val Trp Cys Ala
1               5                   10                  15

Ala Gly Lys Gly Thr Phe Gly Thr Thr Glu Leu Leu
            20                  25

<210> SEQ ID NO 91
<211> LENGTH: 28
<212> TYPE: PRT
```

<213> ORGANISM: Desulfitobacterium dichloroeliminans

<400> SEQUENCE: 91

Thr Trp Ile Leu Ala Leu Asp Thr Lys Gly Val Asn Val Trp Cys Ala
1               5                   10                  15

Ala Gly Lys Gly Thr Phe Gly Thr Thr Glu Leu Ile
            20                  25

<210> SEQ ID NO 92
<211> LENGTH: 28
<212> TYPE: PRT
<213> ORGANISM: Desulfitobacterium metallireducens

<400> SEQUENCE: 92

Val Trp Ile Leu Val Ile Asp Thr Lys Gly Val Asn Val Trp Cys Ala
1               5                   10                  15

Ala Gly Lys Gly Ala Phe Gly Thr Gln Glu Leu Leu
            20                  25

<210> SEQ ID NO 93
<211> LENGTH: 28
<212> TYPE: PRT
<213> ORGANISM: Desulfitobacterium sp.

<400> SEQUENCE: 93

Thr Trp Ile Leu Val Leu Asp Thr Lys Gly Ile Asn Val Trp Cys Ala
1               5                   10                  15

Ala Gly Lys Gly Thr Phe Gly Thr Thr Glu Leu Leu
            20                  25

<210> SEQ ID NO 94
<211> LENGTH: 28
<212> TYPE: PRT
<213> ORGANISM: Desulfosporosinus acidiphilus

<400> SEQUENCE: 94

Ala Tyr Ile Met Val Ile Asp Thr Lys Gly Ile Asn Val Trp Cys Ala
1               5                   10                  15

Ala Gly Lys Gly Thr Phe Gly Thr Glu Ile Ile
            20                  25

<210> SEQ ID NO 95
<211> LENGTH: 28
<212> TYPE: PRT
<213> ORGANISM: Desulfosporosinus orientis

<400> SEQUENCE: 95

Ala Trp Ile Leu Val Leu Asp Thr Lys Gly Val Asn Val Trp Cys Ala
1               5                   10                  15

Ala Gly Lys Gly Thr Phe Gly Thr Thr Glu Leu Ile
            20                  25

<210> SEQ ID NO 96
<211> LENGTH: 28
<212> TYPE: PRT
<213> ORGANISM: Desulfosporosinus sp.

<400> SEQUENCE: 96

Ala Trp Ile Leu Val Leu Asp Thr Lys Gly Ile Asn Val Trp Cys Ala
1               5                   10                  15

Ala Gly Lys Gly Thr Phe Gly Thr Gln Glu Leu Leu
            20                  25

<210> SEQ ID NO 97
<211> LENGTH: 28
<212> TYPE: PRT
<213> ORGANISM: Desulfosporosinus youngiae

<400> SEQUENCE: 97

Ala Trp Ile Leu Val Leu Asp Thr Lys Gly Ile Asn Val Trp Cys Ala
1               5                   10                  15

Ala Gly Lys Gly Thr Phe Gly Thr Gln Glu Leu Leu
            20                  25

<210> SEQ ID NO 98
<211> LENGTH: 28
<212> TYPE: PRT
<213> ORGANISM: Ethanoligenens harbinense

<400> SEQUENCE: 98

Leu Trp Ile Leu Val Leu Asp Thr Asn Gly Val Asn Val Trp Cys Ala
1               5                   10                  15

Ala Gly Lys Gly Thr Phe Gly Thr Asp Glu Leu Val
            20                  25

<210> SEQ ID NO 99
<211> LENGTH: 28
<212> TYPE: PRT
<213> ORGANISM: Syntrophobotulus glycolicus

<400> SEQUENCE: 99

Cys Trp Leu Leu Ile Leu Asp Thr Lys Gly Val Asn Val Trp Cys Ala
1               5                   10                  15

Ala Gly Lys Gly Thr Phe Gly Thr Asp Glu Leu Val
            20                  25

<210> SEQ ID NO 100
<211> LENGTH: 28
<212> TYPE: PRT
<213> ORGANISM: Dethiobacter alkaliphilus

<400> SEQUENCE: 100

Leu Trp Ile Ile Val Leu Asp Thr Arg Gly Ile Asn Val Trp Cys Ala
1               5                   10                  15

Ala Gly Lys Gly Thr Phe Gly Thr Ala Glu Leu Ile
            20                  25

<210> SEQ ID NO 101
<211> LENGTH: 28
<212> TYPE: PRT
<213> ORGANISM: Acetonema longum

<400> SEQUENCE: 101

Leu Trp Ile Leu Val Leu Asp Thr Lys Gly Ile Asn Val Trp Cys Ala
1               5                   10                  15

Ala Gly Lys Gly Thr Phe Gly Thr Asp Glu Leu Val
            20                  25

<210> SEQ ID NO 102
<211> LENGTH: 28
<212> TYPE: PRT
<213> ORGANISM: Methanofollis liminatans

<400> SEQUENCE: 102

Gly Tyr Ile Leu Val Leu Asp Thr Arg Gly Ile Asn Val Trp Cys Ala
1               5                   10                  15

Ala Gly Lys Gly Thr Phe Gly Thr Asp Glu Val Val
            20                  25

<210> SEQ ID NO 103
<211> LENGTH: 28
<212> TYPE: PRT
<213> ORGANISM: Methanoregula boonei

<400> SEQUENCE: 103

Ala Trp Ile Leu Val Leu Asp Thr Lys Gly Val Asn Val Trp Cys Ala
1               5                   10                  15

Ala Gly Lys Gly Thr Phe Gly Thr Gly Glu Leu Ile
            20                  25

<210> SEQ ID NO 104
<211> LENGTH: 28
<212> TYPE: PRT
<213> ORGANISM: Methanoregula formicicum

<400> SEQUENCE: 104

Ala Trp Ile Leu Val Leu Asp Thr Lys Gly Ile Asn Val Trp Cys Ala
1               5                   10                  15

Ala Gly Lys Gly Thr Phe Gly Thr Asp Glu Leu Val
            20                  25

<210> SEQ ID NO 105
<211> LENGTH: 28
<212> TYPE: PRT
<213> ORGANISM: Methanosphaerula palustris

<400> SEQUENCE: 105

Val Tyr Leu Leu Val Leu Asp Thr Tyr Gly Val Asn Val Trp Cys Ala
1               5                   10                  15

Ala Gly Lys Gly Thr Phe Gly Thr Asp Glu Leu Val
            20                  25

<210> SEQ ID NO 106
<211> LENGTH: 28
<212> TYPE: PRT
<213> ORGANISM: Methanospirillum hungatei

<400> SEQUENCE: 106

Ala Tyr Ile Leu Val Leu Asp Thr Lys Gly Ile Asn Val Trp Cys Ala
1               5                   10                  15

Ala Gly Lys Gly Thr Phe Gly Thr Asp Glu Leu Val
            20                  25

<210> SEQ ID NO 107
<211> LENGTH: 28
<212> TYPE: PRT
<213> ORGANISM: Methanolobus tindarius

<400> SEQUENCE: 107

Cys Tyr Ile Leu Val Ile Asp Thr Lys Gly Ile Asn Val Trp Cys Ala
1               5                   10                  15

Ala Gly Lys Gly Thr Phe Gly Thr Asp Glu Ile Val
            20                  25

<210> SEQ ID NO 108
<211> LENGTH: 28

```
<212> TYPE: PRT
<213> ORGANISM: Methanomethylovorans hollandica

<400> SEQUENCE: 108

Gly Tyr Ile Leu Val Leu Asp Thr Lys Gly Ile Asn Val Trp Cys Ala
1               5                   10                  15

Ala Gly Lys Gly Thr Phe Gly Thr Asp Glu Leu Val
            20                  25

<210> SEQ ID NO 109
<211> LENGTH: 28
<212> TYPE: PRT
<213> ORGANISM: Methanocella arvoryzae

<400> SEQUENCE: 109

Cys Tyr Ile Leu Val Leu Asn Thr Tyr Gly Ile Asn Val Trp Cys Ala
1               5                   10                  15

Ala Gly Lys Gly Thr Phe Gly Thr Asp Glu Leu Val
            20                  25

<210> SEQ ID NO 110
<211> LENGTH: 28
<212> TYPE: PRT
<213> ORGANISM: Methanocella paludicola

<400> SEQUENCE: 110

Cys Tyr Ile Leu Val Leu Asp Thr Lys Gly Ile Asn Val Trp Cys Ala
1               5                   10                  15

Ala Gly Lys Gly Thr Phe Gly Thr Asp Glu Leu Met
            20                  25

<210> SEQ ID NO 111
<211> LENGTH: 11
<212> TYPE: PRT
<213> ORGANISM: Desulfovibrio desulfuricans

<400> SEQUENCE: 111

Cys Val Gly Cys Gly Ser Cys Val Asp Val Cys
1               5                   10

<210> SEQ ID NO 112
<211> LENGTH: 11
<212> TYPE: PRT
<213> ORGANISM: Desulfovibrio aespoeensis

<400> SEQUENCE: 112

Cys Val Gly Cys Gly Met Cys Ala Thr Val Cys
1               5                   10

<210> SEQ ID NO 113
<211> LENGTH: 11
<212> TYPE: PRT
<213> ORGANISM: Desulfovibrio africanus

<400> SEQUENCE: 113

Cys Ala Gly Cys Gly Met Cys Thr Val Val Cys
1               5                   10

<210> SEQ ID NO 114
<211> LENGTH: 11
<212> TYPE: PRT
<213> ORGANISM: Desulfomicrobium baculatum

<400> SEQUENCE: 114
```

Cys Val Gly Cys Gly Ile Cys Ala Thr Val Cys
1               5                   10

<210> SEQ ID NO 115
<211> LENGTH: 11
<212> TYPE: PRT
<213> ORGANISM: Desulfonatronospira thiodismutans

<400> SEQUENCE: 115

Cys Met Gly Cys Gly Ser Cys Val Gln Val Cys
1               5                   10

<210> SEQ ID NO 116
<211> LENGTH: 11
<212> TYPE: PRT
<213> ORGANISM: Desulfonatronum lacustre

<400> SEQUENCE: 116

Cys Val Gly Cys Gly Leu Cys Val Ala Val Cys
1               5                   10

<210> SEQ ID NO 117
<211> LENGTH: 11
<212> TYPE: PRT
<213> ORGANISM: Desulfovibrio oxyclinae

<400> SEQUENCE: 117

Cys Val Gly Cys Gly Met Cys Leu Ala Val Cys
1               5                   10

<210> SEQ ID NO 118
<211> LENGTH: 11
<212> TYPE: PRT
<213> ORGANISM: Desulfobulbus propionicus

<400> SEQUENCE: 118

Cys Ile Gly Cys Gly Asn Cys Thr Val Val Cys
1               5                   10

<210> SEQ ID NO 119
<211> LENGTH: 11
<212> TYPE: PRT
<213> ORGANISM: Desulfobacterium sp.

<400> SEQUENCE: 119

Cys Ile Gly Cys Gly Arg Cys Leu Glu Val Cys
1               5                   10

<210> SEQ ID NO 120
<211> LENGTH: 11
<212> TYPE: PRT
<213> ORGANISM: Geobacter sulfurreducens

<400> SEQUENCE: 120

Cys Val Gly Cys Gly Met Cys Val Glu Val Cys
1               5                   10

<210> SEQ ID NO 121
<211> LENGTH: 11
<212> TYPE: PRT
<213> ORGANISM: Geobacter metallireducens

<400> SEQUENCE: 121

Cys Ile Gly Cys Gly Met Cys Val Ala Val Cys

<210> SEQ ID NO 122
<211> LENGTH: 11
<212> TYPE: PRT
<213> ORGANISM: Geobacter sulfurreducens

<400> SEQUENCE: 122

Cys Val Gly Cys Gly Met Cys Val Glu Val Cys
1               5                   10

<210> SEQ ID NO 123
<211> LENGTH: 11
<212> TYPE: PRT
<213> ORGANISM: Geobacter metallireducens

<400> SEQUENCE: 123

Cys Ile Gly Cys Gly Met Cys Val Ala Val Cys
1               5                   10

<210> SEQ ID NO 124
<211> LENGTH: 11
<212> TYPE: PRT
<213> ORGANISM: Geobacter sp.

<400> SEQUENCE: 124

Cys Ile Gly Cys Gly Arg Cys Leu Glu Val Cys
1               5                   10

<210> SEQ ID NO 125
<211> LENGTH: 11
<212> TYPE: PRT
<213> ORGANISM: Geobacter sp.

<400> SEQUENCE: 125

Cys Val Gly Cys Gly Arg Cys Thr Glu Val Cys
1               5                   10

<210> SEQ ID NO 126
<211> LENGTH: 11
<212> TYPE: PRT
<213> ORGANISM: Geobacter sp.

<400> SEQUENCE: 126

Cys Val Gly Cys Gly Arg Cys Ile Glu Val Cys
1               5                   10

<210> SEQ ID NO 127
<211> LENGTH: 11
<212> TYPE: PRT
<213> ORGANISM: Geobacter uraniireducens

<400> SEQUENCE: 127

Cys Ile Gly Cys Gly Arg Cys Val Glu Val Cys
1               5                   10

<210> SEQ ID NO 128
<211> LENGTH: 11
<212> TYPE: PRT
<213> ORGANISM: Geobacter bemidjiensis

<400> SEQUENCE: 128

Cys Val Gly Cys Gly Arg Cys Ile Glu Val Cys
1               5                   10

<210> SEQ ID NO 129
<211> LENGTH: 11
<212> TYPE: PRT
<213> ORGANISM: Syntrophorhabdus aromaticivorans

<400> SEQUENCE: 129

Cys Asn Gly Cys Gly Ile Cys Leu Thr Val Cys
1               5                   10

<210> SEQ ID NO 130
<211> LENGTH: 11
<212> TYPE: PRT
<213> ORGANISM: Desulfomonile tiedjei

<400> SEQUENCE: 130

Cys Ser Gly Cys Gly Met Cys Leu Gln Val Cys
1               5                   10

<210> SEQ ID NO 131
<211> LENGTH: 11
<212> TYPE: PRT
<213> ORGANISM: Syntrophus aciditrophicus

<400> SEQUENCE: 131

Cys Ile Gly Cys Gly Met Cys Leu Glu Val Cys
1               5                   10

<210> SEQ ID NO 132
<211> LENGTH: 11
<212> TYPE: PRT
<213> ORGANISM: Unknown
<220> FEATURE:
<223> OTHER INFORMATION: Description of Unknown: Delta
      proteobacterium peptide

<400> SEQUENCE: 132

Cys Val Gly Cys Gly Thr Cys Leu Glu Val Cys
1               5                   10

<210> SEQ ID NO 133
<211> LENGTH: 11
<212> TYPE: PRT
<213> ORGANISM: Unknown
<220> FEATURE:
<223> OTHER INFORMATION: Description of Unknown: Delta
      proteobacterium peptide

<400> SEQUENCE: 133

Cys Val Gly Cys Gly Met Cys Leu Met Val Cys
1               5                   10

<210> SEQ ID NO 134
<211> LENGTH: 11
<212> TYPE: PRT
<213> ORGANISM: Acetivibrio cellulolyticus

<400> SEQUENCE: 134

Cys Lys Gly Cys Gly Arg Cys Ala Glu Val Cys
1               5                   10

<210> SEQ ID NO 135
<211> LENGTH: 11
<212> TYPE: PRT
<213> ORGANISM: Dehalobacter restrictus

<400> SEQUENCE: 135

Cys Thr Gly Cys Gly Arg Cys Leu Glu Val Cys
1               5                   10

<210> SEQ ID NO 136
<211> LENGTH: 11
<212> TYPE: PRT
<213> ORGANISM: Desulfitobacterium dehalogenans

<400> SEQUENCE: 136

Cys Thr Gly Cys Gly Lys Cys Ile Glu Val Cys
1               5                   10

<210> SEQ ID NO 137
<211> LENGTH: 11
<212> TYPE: PRT
<213> ORGANISM: Desulfitobacterium dichloroeliminans

<400> SEQUENCE: 137

Cys Thr Gly Cys Gly Lys Cys Phe Glu Val Cys
1               5                   10

<210> SEQ ID NO 138
<211> LENGTH: 11
<212> TYPE: PRT
<213> ORGANISM: Desulfitobacterium metallireducens

<400> SEQUENCE: 138

Cys Ile Gly Cys Gly Arg Cys Leu Glu Val Cys
1               5                   10

<210> SEQ ID NO 139
<211> LENGTH: 11
<212> TYPE: PRT
<213> ORGANISM: Desulfitobacterium sp.

<400> SEQUENCE: 139

Cys Thr Gly Cys Gly Lys Cys Ile Glu Val Cys
1               5                   10

<210> SEQ ID NO 140
<211> LENGTH: 11
<212> TYPE: PRT
<213> ORGANISM: Desulfosporosinus acidiphilus

<400> SEQUENCE: 140

Cys Thr Gly Cys Gly Lys Cys Leu Glu Val Cys
1               5                   10

<210> SEQ ID NO 141
<211> LENGTH: 11
<212> TYPE: PRT
<213> ORGANISM: Desulfosporosinus orientis

<400> SEQUENCE: 141

Cys Thr Gly Cys Gly Lys Cys Leu Glu Val Cys
1               5                   10

<210> SEQ ID NO 142
<211> LENGTH: 11
<212> TYPE: PRT
<213> ORGANISM: Desulfosporosinus sp.

<400> SEQUENCE: 142

Cys Thr Gly Cys Gly Arg Cys Leu Glu Val Cys

```
1               5                   10

<210> SEQ ID NO 143
<211> LENGTH: 11
<212> TYPE: PRT
<213> ORGANISM: Desulfosporosinus youngiae

<400> SEQUENCE: 143

Cys Thr Gly Cys Gly Arg Cys Leu Glu Val Cys
1               5                   10

<210> SEQ ID NO 144
<211> LENGTH: 11
<212> TYPE: PRT
<213> ORGANISM: Ethanoligenens harbinense

<400> SEQUENCE: 144

Cys Thr Gly Cys Gly Met Cys Val Asn Val Cys
1               5                   10

<210> SEQ ID NO 145
<211> LENGTH: 11
<212> TYPE: PRT
<213> ORGANISM: Syntrophobotulus glycolicus

<400> SEQUENCE: 145

Cys Val Gly Cys Glu Arg Cys Thr Glu Val Cys
1               5                   10

<210> SEQ ID NO 146
<211> LENGTH: 11
<212> TYPE: PRT
<213> ORGANISM: Dethiobacter alkaliphilus

<400> SEQUENCE: 146

Cys Ser Gly Cys Arg Leu Cys Thr Glu Val Cys
1               5                   10

<210> SEQ ID NO 147
<211> LENGTH: 11
<212> TYPE: PRT
<213> ORGANISM: Acetonema longum

<400> SEQUENCE: 147

Cys Ile Gly Cys Gly Met Cys Leu Asn Val Cys
1               5                   10

<210> SEQ ID NO 148
<211> LENGTH: 11
<212> TYPE: PRT
<213> ORGANISM: Methanofollis liminatans

<400> SEQUENCE: 148

Cys Phe Asn Cys Arg Arg Cys Ile Glu Val Cys
1               5                   10

<210> SEQ ID NO 149
<211> LENGTH: 11
<212> TYPE: PRT
<213> ORGANISM: Methanoregula boonei

<400> SEQUENCE: 149

Cys Ile Asn Cys Arg Arg Cys Thr Glu Val Cys
1               5                   10
```

<210> SEQ ID NO 150
<211> LENGTH: 11
<212> TYPE: PRT
<213> ORGANISM: Methanoregula formicicum

<400> SEQUENCE: 150

Cys Ile Asn Cys Lys Arg Cys Met Gln Val Cys
1               5                   10

<210> SEQ ID NO 151
<211> LENGTH: 11
<212> TYPE: PRT
<213> ORGANISM: Methanosphaerula palustris

<400> SEQUENCE: 151

Cys Val Asn Cys Gly Ala Cys Ser Thr Val Cys
1               5                   10

<210> SEQ ID NO 152
<211> LENGTH: 11
<212> TYPE: PRT
<213> ORGANISM: Methanospirillum hungatei

<400> SEQUENCE: 152

Cys Ile Asn Cys Lys Arg Cys Thr Glu Val Cys
1               5                   10

<210> SEQ ID NO 153
<211> LENGTH: 11
<212> TYPE: PRT
<213> ORGANISM: Methanolobus tindarius

<400> SEQUENCE: 153

Cys Ile Asn Cys Leu Met Cys Thr Asn Val Cys
1               5                   10

<210> SEQ ID NO 154
<211> LENGTH: 11
<212> TYPE: PRT
<213> ORGANISM: Methanomethylovorans hollandica

<400> SEQUENCE: 154

Cys Ile Asn Cys Leu Arg Cys Thr His Val Cys
1               5                   10

<210> SEQ ID NO 155
<211> LENGTH: 11
<212> TYPE: PRT
<213> ORGANISM: Methanocella arvoryzae

<400> SEQUENCE: 155

Cys Val Gly Cys Gly Met Cys Trp Asn Val Cys
1               5                   10

<210> SEQ ID NO 156
<211> LENGTH: 11
<212> TYPE: PRT
<213> ORGANISM: Methanocella paludicola

<400> SEQUENCE: 156

Cys Thr Gly Cys Gly Met Cys Thr Lys Val Cys
1               5                   10

<210> SEQ ID NO 157

```
<210> SEQ ID NO 157
<211> LENGTH: 11
<212> TYPE: PRT
<213> ORGANISM: Desulfovibrio desulfuricans

<400> SEQUENCE: 157

Cys Met Glu Cys Gly Ala Cys Ala Arg Asn Cys
1               5                   10

<210> SEQ ID NO 158
<211> LENGTH: 11
<212> TYPE: PRT
<213> ORGANISM: Desulfovibrio aespoeensis

<400> SEQUENCE: 158

Cys Met Glu Cys Gly Ala Cys Ala Arg Asn Cys
1               5                   10

<210> SEQ ID NO 159
<211> LENGTH: 11
<212> TYPE: PRT
<213> ORGANISM: Desulfovibrio africanus

<400> SEQUENCE: 159

Cys Met Glu Cys Gly Ala Cys Ala Leu Asn Cys
1               5                   10

<210> SEQ ID NO 160
<211> LENGTH: 11
<212> TYPE: PRT
<213> ORGANISM: Desulfomicrobium baculatum

<400> SEQUENCE: 160

Cys Met Glu Cys Gly Ala Cys Ala Leu Asn Cys
1               5                   10

<210> SEQ ID NO 161
<211> LENGTH: 11
<212> TYPE: PRT
<213> ORGANISM: Desulfonatronospira thiodismutans

<400> SEQUENCE: 161

Cys Met Glu Cys Gly Ala Cys Ala Leu Asn Cys
1               5                   10

<210> SEQ ID NO 162
<211> LENGTH: 11
<212> TYPE: PRT
<213> ORGANISM: Desulfonatronum lacustre

<400> SEQUENCE: 162

Cys Met Glu Cys Gly Ala Cys Ala Leu Asn Cys
1               5                   10

<210> SEQ ID NO 163
<211> LENGTH: 11
<212> TYPE: PRT
<213> ORGANISM: Desulfovibrio oxyclinae

<400> SEQUENCE: 163

Cys Met Glu Cys Gly Ala Cys Ala Leu Asn Cys
1               5                   10

<210> SEQ ID NO 164
<211> LENGTH: 11
<212> TYPE: PRT
```

<213> ORGANISM: Desulfobulbus propionicus

<400> SEQUENCE: 164

Cys Met Glu Cys Gly Ala Cys Ala Arg Asn Cys
1               5                   10

<210> SEQ ID NO 165
<211> LENGTH: 11
<212> TYPE: PRT
<213> ORGANISM: Desulfobacterium sp.

<400> SEQUENCE: 165

Cys Met Glu Cys Gly Ala Cys Ala Ile Asn Cys
1               5                   10

<210> SEQ ID NO 166
<211> LENGTH: 11
<212> TYPE: PRT
<213> ORGANISM: Geobacter sulfurreducens

<400> SEQUENCE: 166

Cys Met Glu Cys Gly Ala Cys Ala Val Asn Cys
1               5                   10

<210> SEQ ID NO 167
<211> LENGTH: 11
<212> TYPE: PRT
<213> ORGANISM: Geobacter metallireducens

<400> SEQUENCE: 167

Cys Met Glu Cys Gly Ala Cys Ala Val Asn Cys
1               5                   10

<210> SEQ ID NO 168
<211> LENGTH: 11
<212> TYPE: PRT
<213> ORGANISM: Geobacter sulfurreducens

<400> SEQUENCE: 168

Cys Met Glu Cys Gly Ala Cys Ala Val Asn Cys
1               5                   10

<210> SEQ ID NO 169
<211> LENGTH: 11
<212> TYPE: PRT
<213> ORGANISM: Geobacter metallireducens

<400> SEQUENCE: 169

Cys Met Glu Cys Gly Ala Cys Ala Val Asn Cys
1               5                   10

<210> SEQ ID NO 170
<211> LENGTH: 11
<212> TYPE: PRT
<213> ORGANISM: Geobacter sp.

<400> SEQUENCE: 170

Cys Met Glu Cys Gly Ala Cys Gln Arg Asn Cys
1               5                   10

<210> SEQ ID NO 171
<211> LENGTH: 11
<212> TYPE: PRT
<213> ORGANISM: Geobacter sp.

```
<400> SEQUENCE: 171

Cys Met Glu Cys Gly Ala Cys Ala Leu Asn Cys
1               5                   10

<210> SEQ ID NO 172
<211> LENGTH: 11
<212> TYPE: PRT
<213> ORGANISM: Geobacter sp.

<400> SEQUENCE: 172

Cys Met Glu Cys Gly Ala Cys Ala Leu Asn Cys
1               5                   10

<210> SEQ ID NO 173
<211> LENGTH: 11
<212> TYPE: PRT
<213> ORGANISM: Geobacter uraniireducens

<400> SEQUENCE: 173

Cys Met Glu Cys Gly Ala Cys Ala Lys Asn Cys
1               5                   10

<210> SEQ ID NO 174
<211> LENGTH: 11
<212> TYPE: PRT
<213> ORGANISM: Geobacter bemidjiensis

<400> SEQUENCE: 174

Cys Met Glu Cys Gly Ala Cys Ala Leu Asn Cys
1               5                   10

<210> SEQ ID NO 175
<211> LENGTH: 11
<212> TYPE: PRT
<213> ORGANISM: Syntrophorhabdus aromaticivorans

<400> SEQUENCE: 175

Cys Ile Glu Cys Gly Ala Cys Gln Arg Asn Cys
1               5                   10

<210> SEQ ID NO 176
<211> LENGTH: 11
<212> TYPE: PRT
<213> ORGANISM: Desulfomonile tiedjei

<400> SEQUENCE: 176

Cys Met Glu Cys Gly Ala Cys Ala Lys Asn Cys
1               5                   10

<210> SEQ ID NO 177
<211> LENGTH: 11
<212> TYPE: PRT
<213> ORGANISM: Syntrophus aciditrophicus

<400> SEQUENCE: 177

Cys Ile Glu Cys Gly Ala Cys Ser Arg Asn Cys
1               5                   10

<210> SEQ ID NO 178
<211> LENGTH: 11
<212> TYPE: PRT
<213> ORGANISM: Unknown
<220> FEATURE:
<223> OTHER INFORMATION: Description of Unknown: Delta
      proteobacterium peptide
```

<400> SEQUENCE: 178

Cys Met Glu Cys Gly Ala Cys Met His Asn Cys
1               5                   10

<210> SEQ ID NO 179
<211> LENGTH: 11
<212> TYPE: PRT
<213> ORGANISM: Unknown
<220> FEATURE:
<223> OTHER INFORMATION: Description of Unknown: Delta
      proteobacterium peptide

<400> SEQUENCE: 179

Cys Met Glu Cys Gly Ala Cys Ala Arg Asn Cys
1               5                   10

<210> SEQ ID NO 180
<211> LENGTH: 11
<212> TYPE: PRT
<213> ORGANISM: Acetivibrio cellulolyticus

<400> SEQUENCE: 180

Cys Met Glu Cys Ser Ala Cys Ala Arg Asn Cys
1               5                   10

<210> SEQ ID NO 181
<211> LENGTH: 11
<212> TYPE: PRT
<213> ORGANISM: Dehalobacter restrictus

<400> SEQUENCE: 181

Cys Met Glu Cys Gly Ala Cys Ala Arg Asn Cys
1               5                   10

<210> SEQ ID NO 182
<211> LENGTH: 11
<212> TYPE: PRT
<213> ORGANISM: Desulfitobacterium dehalogenans

<400> SEQUENCE: 182

Cys Ile Glu Cys Gly Ala Cys Val Lys Asn Cys
1               5                   10

<210> SEQ ID NO 183
<211> LENGTH: 11
<212> TYPE: PRT
<213> ORGANISM: Desulfitobacterium dichloroeliminans

<400> SEQUENCE: 183

Cys Ile Glu Cys Gly Ala Cys Val Lys Asn Cys
1               5                   10

<210> SEQ ID NO 184
<211> LENGTH: 11
<212> TYPE: PRT
<213> ORGANISM: Desulfitobacterium metallireducens

<400> SEQUENCE: 184

Cys Met Glu Cys Gly Ala Cys Val Arg Asn Cys
1               5                   10

<210> SEQ ID NO 185
<211> LENGTH: 11
<212> TYPE: PRT

<213> ORGANISM: Desulfitobacterium sp.

<400> SEQUENCE: 185

Cys Ile Glu Cys Gly Ala Cys Val Lys Asn Cys
1               5                   10

<210> SEQ ID NO 186
<211> LENGTH: 11
<212> TYPE: PRT
<213> ORGANISM: Desulfosporosinus acidiphilus

<400> SEQUENCE: 186

Cys Ile Glu Cys Gly Ala Cys Val Lys Asn Cys
1               5                   10

<210> SEQ ID NO 187
<211> LENGTH: 11
<212> TYPE: PRT
<213> ORGANISM: Desulfosporosinus orientis

<400> SEQUENCE: 187

Cys Ile Glu Cys Gly Ala Cys Val Lys Asn Cys
1               5                   10

<210> SEQ ID NO 188
<211> LENGTH: 11
<212> TYPE: PRT
<213> ORGANISM: Desulfosporosinus sp.

<400> SEQUENCE: 188

Cys Met Glu Cys Gly Ala Cys Val Lys Asn Cys
1               5                   10

<210> SEQ ID NO 189
<211> LENGTH: 11
<212> TYPE: PRT
<213> ORGANISM: Desulfosporosinus youngiae

<400> SEQUENCE: 189

Cys Met Glu Cys Gly Ala Cys Val Lys Asn Cys
1               5                   10

<210> SEQ ID NO 190
<211> LENGTH: 11
<212> TYPE: PRT
<213> ORGANISM: Ethanoligenens harbinense

<400> SEQUENCE: 190

Cys Met Glu Cys Gly Ala Cys Ala Lys Asn Cys
1               5                   10

<210> SEQ ID NO 191
<211> LENGTH: 11
<212> TYPE: PRT
<213> ORGANISM: Syntrophobotulus glycolicus

<400> SEQUENCE: 191

Cys Met Glu Cys Gly Ala Cys Ala Met Asn Cys
1               5                   10

<210> SEQ ID NO 192
<211> LENGTH: 11
<212> TYPE: PRT
<213> ORGANISM: Dethiobacter alkaliphilus

```
<400> SEQUENCE: 192

Cys Met Glu Cys Gly Ala Cys Ala Arg Asn Cys
1               5                   10

<210> SEQ ID NO 193
<211> LENGTH: 11
<212> TYPE: PRT
<213> ORGANISM: Acetonema longum

<400> SEQUENCE: 193

Cys Met Glu Cys Gly Ala Cys Ala Gln Asn Cys
1               5                   10

<210> SEQ ID NO 194
<211> LENGTH: 11
<212> TYPE: PRT
<213> ORGANISM: Methanofollis liminatans

<400> SEQUENCE: 194

Cys Met Glu Cys Gly Ala Cys Ala Arg Asn Cys
1               5                   10

<210> SEQ ID NO 195
<211> LENGTH: 11
<212> TYPE: PRT
<213> ORGANISM: Methanoregula boonei

<400> SEQUENCE: 195

Cys Met Glu Cys Gly Ala Cys Ala Lys Asn Cys
1               5                   10

<210> SEQ ID NO 196
<211> LENGTH: 11
<212> TYPE: PRT
<213> ORGANISM: Methanoregula formicicum

<400> SEQUENCE: 196

Cys Met Glu Cys Gly Ala Cys Ala Lys Asn Cys
1               5                   10

<210> SEQ ID NO 197
<211> LENGTH: 11
<212> TYPE: PRT
<213> ORGANISM: Methanosphaerula palustris

<400> SEQUENCE: 197

Cys Met Glu Cys Gly Ala Cys Gln Val Asn Cys
1               5                   10

<210> SEQ ID NO 198
<211> LENGTH: 11
<212> TYPE: PRT
<213> ORGANISM: Methanospirillum hungatei

<400> SEQUENCE: 198

Cys Met Glu Cys Gly Ala Cys Ala Leu Asn Cys
1               5                   10

<210> SEQ ID NO 199
<211> LENGTH: 11
<212> TYPE: PRT
<213> ORGANISM: Methanolobus tindarius

<400> SEQUENCE: 199
```

Cys Met Glu Cys Gly Ala Cys Ala Gly Asn Cys
1               5                   10

<210> SEQ ID NO 200
<211> LENGTH: 11
<212> TYPE: PRT
<213> ORGANISM: Methanomethylovorans hollandica

<400> SEQUENCE: 200

Cys Met Glu Cys Gly Ala Cys Ala Arg Asn Cys
1               5                   10

<210> SEQ ID NO 201
<211> LENGTH: 11
<212> TYPE: PRT
<213> ORGANISM: Methanocella arvoryzae

<400> SEQUENCE: 201

Cys Met Glu Cys Gly Ala Cys Gln Leu Asn Cys
1               5                   10

<210> SEQ ID NO 202
<211> LENGTH: 11
<212> TYPE: PRT
<213> ORGANISM: Methanocella paludicola

<400> SEQUENCE: 202

Cys Met Glu Cys Gly Ala Cys Phe Leu Asn Cys
1               5                   10

<210> SEQ ID NO 203
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Cys Cys Gly
1

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Ile or Val
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (10)..(10)
<223> OTHER INFORMATION: Ala or Gly
<220> FEATURE:
<221> NAME/KEY: MOD_RES
<222> LOCATION: (13)..(13)
<223> OTHER INFORMATION: Gly, Asp, Lys or Gln
<220> FEATURE:

```
<221> NAME/KEY: MOD_RES
<222> LOCATION: (14)..(14)
<223> OTHER INFORMATION: Thr, Leu, Ser or Ala

<400> SEQUENCE: 204

Thr Xaa Gly Xaa Asn Xaa Trp Cys Ala Xaa Gly Lys Xaa Xaa Phe
1               5                   10                  15

<210> SEQ ID NO 205
<211> LENGTH: 166
<212> TYPE: PRT
<213> ORGANISM: Desulfovibrio desulfuricans

<400> SEQUENCE: 205

Met Asp Gly Phe Ala Arg Thr Ala Ala Gly Pro Val Pro Arg Val Arg
1               5                   10                  15

Thr Tyr Leu Arg Arg Asp Asp Arg Val Gly Asp Leu Arg Ala Arg Leu
            20                  25                  30

Gly Thr Asn Arg His Asp Phe Lys Val Val Pro Gly Leu Tyr Cys Val
            35                  40                  45

Gly Glu Pro Asp Arg Thr Ser Pro Val Leu Val Thr Ala Asn Tyr Lys
    50                  55                  60

Leu Thr Phe Asp Thr Leu Arg Glu Arg Leu Thr Ser Ile Asp Ala Trp
65                  70                  75                  80

Leu Leu Val Val Asp Thr Arg Gly Ile Asn Val Trp Cys Ala Ala Gly
                85                  90                  95

Lys Gly Leu Phe Thr Ala Ser Glu Val Ala Phe Ser Val Asn Ala Val
                100                 105                 110

Arg Leu His Gln Val Val Glu His Arg Glu Leu Ile Leu Pro Gln Leu
            115                 120                 125

Ala Ala Thr Gly Val Ala Ala Arg Glu Val Glu Arg Ile Cys Gly Phe
        130                 135                 140

Lys Val Leu Trp Gly Pro Ile Arg Ala Arg Asp Leu Pro Ala Phe Leu
145                 150                 155                 160

Arg Asn Gly Asn Lys Ala
                165
```